United States Patent
Chaves Fontes et al.

(10) Patent No.: US 10,634,686 B2
(45) Date of Patent: Apr. 28, 2020

(54) BIOMARKERS RELATED TO ORGAN FUNCTION

(71) Applicant: University of Pittsburgh—Of the Commonwealth System of Higher Education, Pittsburgh, PA (US)

(72) Inventors: Paulo Artur Chaves Fontes, Pittsburgh, PA (US); John A. Kellum, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/024,297

(22) PCT Filed: Sep. 23, 2014

(86) PCT No.: PCT/US2014/057049
§ 371 (c)(1),
(2) Date: Mar. 23, 2016

(87) PCT Pub. No.: WO2015/042602
PCT Pub. Date: Mar. 26, 2015

(65) Prior Publication Data
US 2016/0231330 A1    Aug. 11, 2016

Related U.S. Application Data

(60) Provisional application No. 61/881,333, filed on Sep. 23, 2013.

(51) Int. Cl.
*G01N 33/68* (2006.01)
*C12Q 1/6883* (2018.01)

(52) U.S. Cl.
CPC ....... *G01N 33/6863* (2013.01); *C12Q 1/6883* (2013.01); *G01N 33/6866* (2013.01); *G01N 33/6869* (2013.01); *C12Q 2600/158* (2013.01); *G01N 2333/525* (2013.01); *G01N 2333/545* (2013.01); *G01N 2333/5406* (2013.01); *G01N 2333/5412* (2013.01); *G01N 2333/5421* (2013.01); *G01N 2333/5428* (2013.01); *G01N 2333/5434* (2013.01); *G01N 2333/56* (2013.01); *G01N 2333/57* (2013.01); *G01N 2570/00* (2013.01); *G01N 2800/085* (2013.01); *G01N 2800/50* (2013.01); *G01N 2800/60* (2013.01)

(58) Field of Classification Search
CPC .............. C12Q 1/6883; C12Q 2600/15; G01N 2333/5406; G01N 2333/5412; G01N 2333/5421; G01N 2333/5428; G01N 2333/5434; G01N 2333/545; G01N 2333/56; G01N 2333/57; G01N 2570/00; G01N 2800/085; G01N 2800/50; G01N 2800/60; G01N 33/6863; G01N 33/6866; G01N 33/6869

See application file for complete search history.

(56) References Cited

U.S. PATENT DOCUMENTS

| | | | |
|---|---|---|---|
| 6,054,261 A * | 4/2000 | Masterson | A01N 1/02 435/1.2 |
| 7,824,848 B2 | 11/2010 | Owen et al. | |
| 2002/0102239 A1* | 8/2002 | Koopmans | C12N 5/0618 424/93.7 |
| 2009/0149335 A1* | 6/2009 | Mathew | C40B 30/04 506/7 |
| 2011/0076666 A1 | 3/2011 | Brassil | |
| 2011/0111976 A1* | 5/2011 | Fare | C12Q 1/6883 506/9 |
| 2012/0315618 A1 | 12/2012 | Kravitz et al. | |
| 2014/0141986 A1* | 5/2014 | Spetzler | C12Q 1/6886 506/9 |
| 2015/0230453 A1 | 8/2015 | Fontes et al. | |

FOREIGN PATENT DOCUMENTS

WO    WO-2011140241 A2 *  11/2011  ........... A01N 1/0226

OTHER PUBLICATIONS

Izamis et al. J. Healthcare Engineering (2012) 3(2): 279-298 (Year: 2012).*
Gringeri et al. Transplantation Proc. (2012) 44: 2026-2028 (Year: 2012).*
Dries et al. Am. J. Transplant. (Mar. 2013) 13: 1327-1335 (Year: 2013).*
Hotter et al. Inflammation (1996) 20(1): 23-31 (Year: 1996).*
Bon et al., "New strategies to optimize kidney recovery and preservation in transplantation," *Nature Review Nephrology*, vol. 8, No. 6, pp. 339-347, 2012.
Koomen et al., "Proteome analysis of isolated perfused organ effluent as a novel model for protein biomarker discovery," *Journal of Proteome Research*, vol. 5, No. 1, pp. 177-182, 2006.

* cited by examiner

*Primary Examiner* — Susan M Hanley

(74) *Attorney, Agent, or Firm* — Klarquist Sparkman, LLP

(57) ABSTRACT

Disclosed herein are methods of identifying biomarkers (such as genes (e.g., RNA or mRNA), proteins, and/or small molecules) that can be used to predict organ or tissue function or dysfunction. In some embodiments, the methods include ex vivo perfusion of the organ or tissue, collection of samples from the organ or tissue (for example, perfusate, fluids produced by the organ (such as bile or urine), or tissue biopsies) and measuring the level of one or more biomarkers in the sample. It is also disclosed herein that an analysis of biomarkers (such as genes (e.g., RNA or mRNA), proteins, and/or small molecules) present in a biological sample from an organ, tissue, or subject can be used to identify whether the organ, tissue, or subject is at risk for (or has) organ dysfunction or organ failure.

8 Claims, 46 Drawing Sheets

FIG. 7

Machine Perfusion-Necrospy

| Category | Genes Downregulated > 2 fold | # Molecules |
|---|---|---|
| Liver Necrosis | ADAR,BCL2,CASP3,CASP7,CASP9,CHUK,EGF | 25 |
| Liver Inflammation | C3,CD44,IFNGR1,IGF1R,IKBKB,IL12RB2,IL1R1 | 16 |
| Liver Damage | C3,CBLB,CD44,IFNGR1,IKBKB,IL4R,IL6ST,MAF | 15 |
| Liver Damage | IFNGR1,IKBKB,IL6ST,MAPK8,MAPK9,NFKB1,P | 10 |
| Liver Steatosis | C3,GHR,IL6ST,JAK2,MAPK8,PPARA,PTEN | 7 |
| Liver Degeneration | CHUK,IKBKB,MERTK,TBK1 | 4 |
| Liver Degradation | ADAR | 1 |
| Liver Edema | VEGFA | 1 |
| Liver Hemorrhaging | IKBKB,TBK1 | 2 |
| Liver Fibrosis | CD44 | 1 |
| Liver Cirrhosis | CD38 | 1 |

CONTROL: Cold Ischamea-Necrospy

| Category | # Molecules: Upregulated > 2 fold | # Molecules |
|---|---|---|
| Liver Fibrosis | FCGR2B,FGFR2 | 2 |
| Liver Damage | FCGR2B,IL2,SCARB1 | 3 |
| Liver Steatosis | FGFR2,GHR | 2 |
| Liver Cirrhosis | FBLN1 | 1 |
| Liver Damage | FCGR2B,IL2 | 2 |
| Liver Hypoplasia | TSC1 | 1 |
| Liver Inflammation | FCGR2B,IL2 | 2 |
| Liver Necrosis | ENDOG | 1 |

© 2000-2013 Ingenuity Systems, Inc. All rights reserved.

FIG. 8
Enrichment By Biological Process Networks Following Machine Perfusion
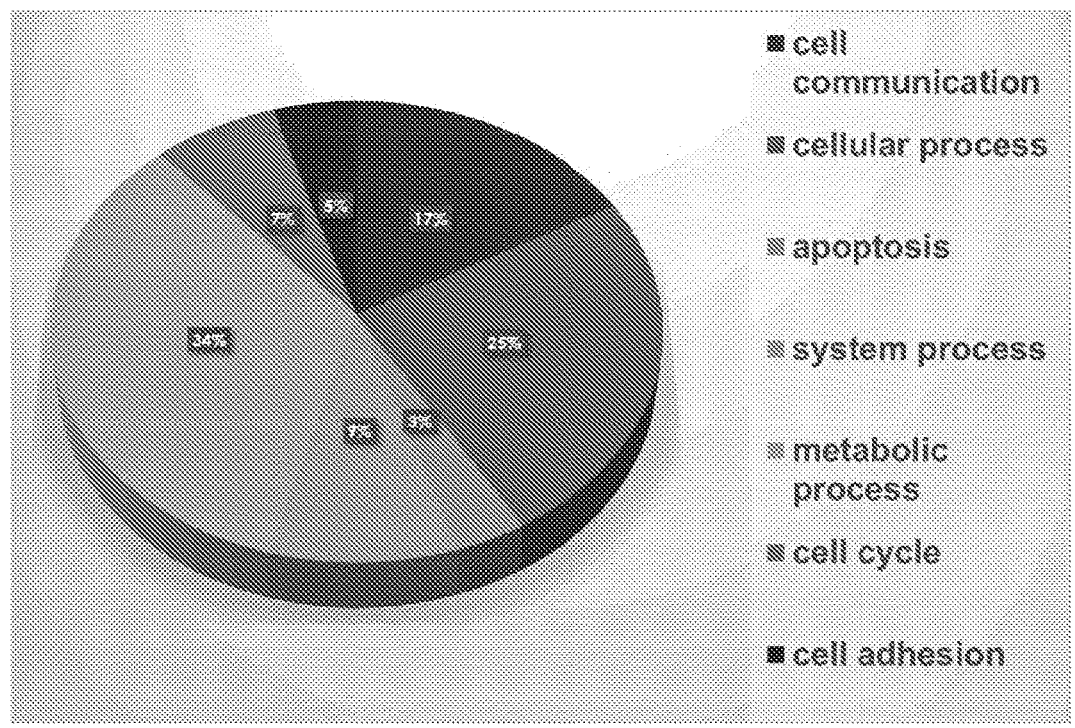
Metabolic Network Analysis        FIG. 9A
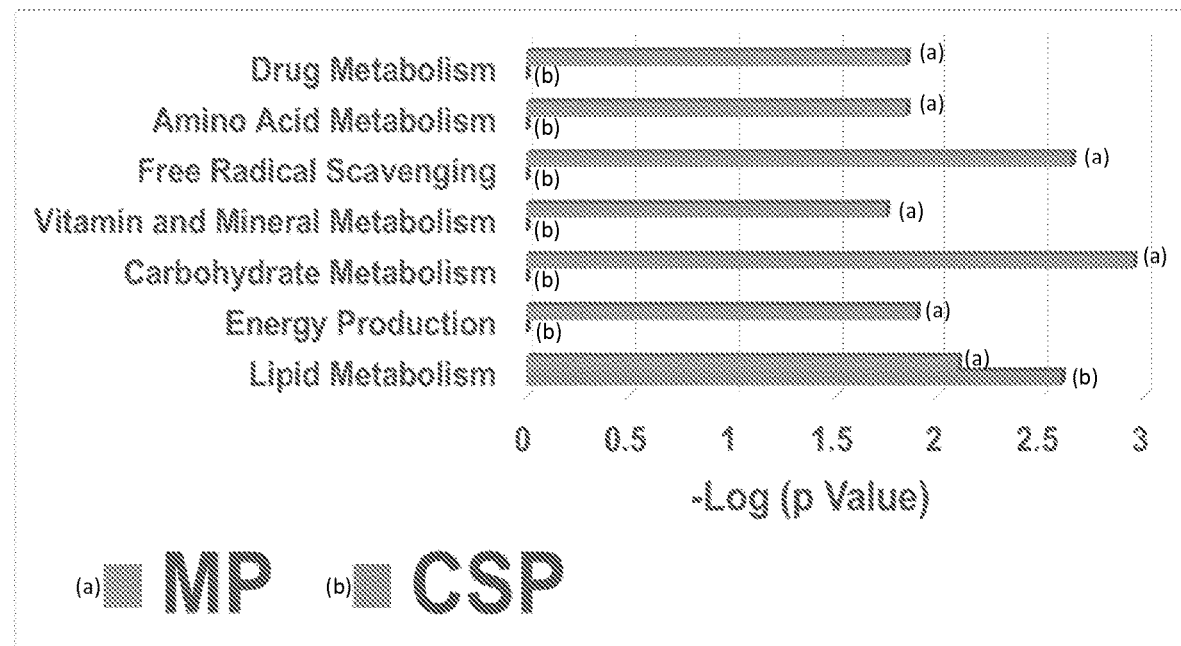

Biological Process Network Analysis

Signaling Pathway Comparison

FIG. 19A
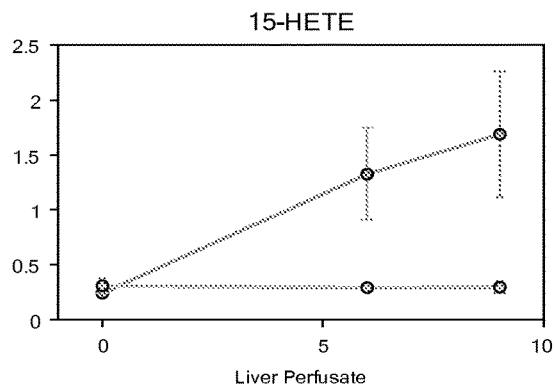
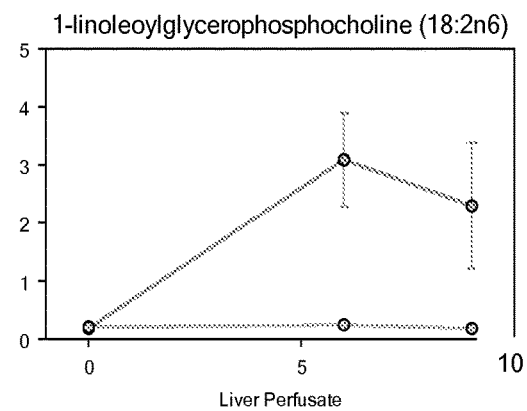
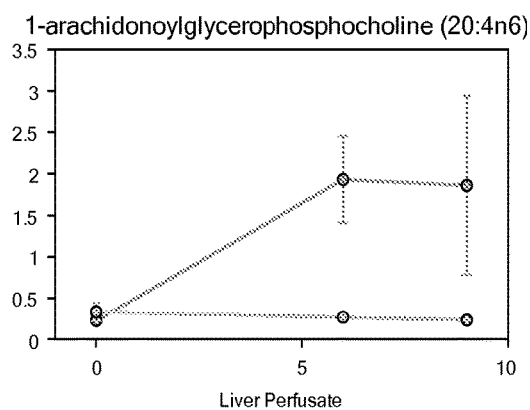
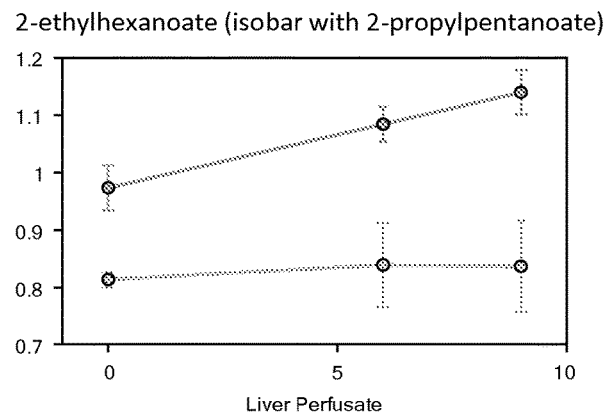
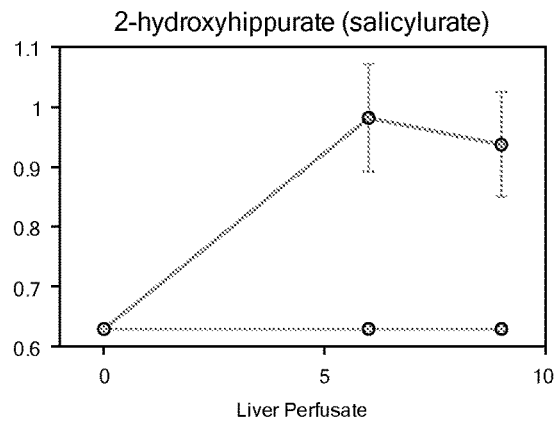
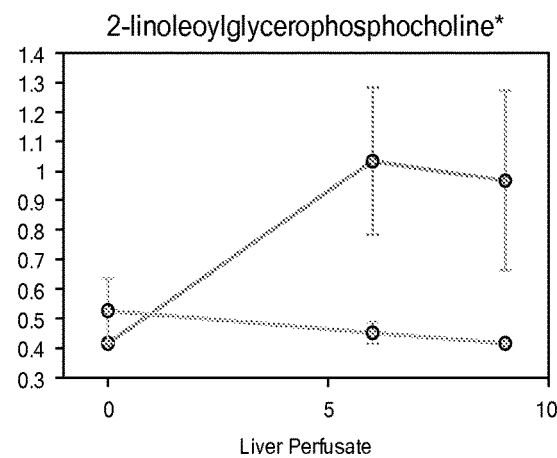

FIG. 19B
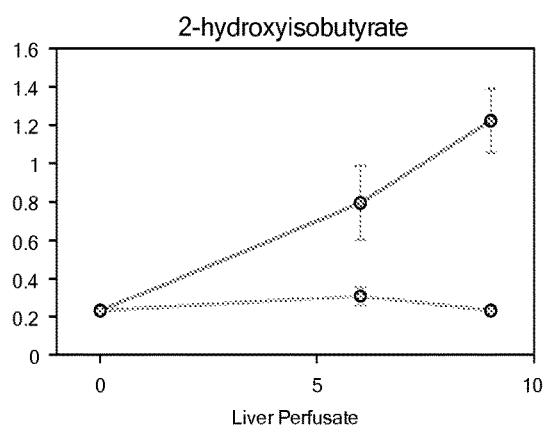
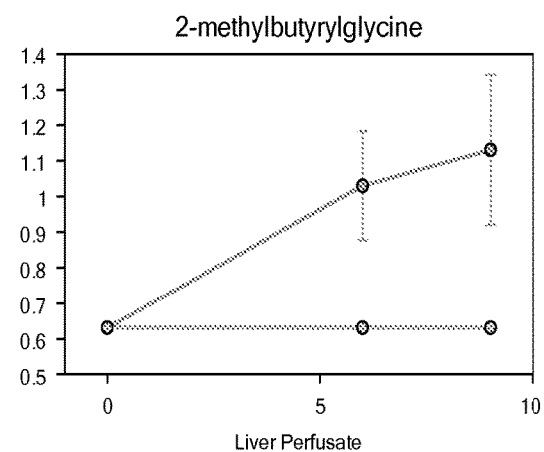
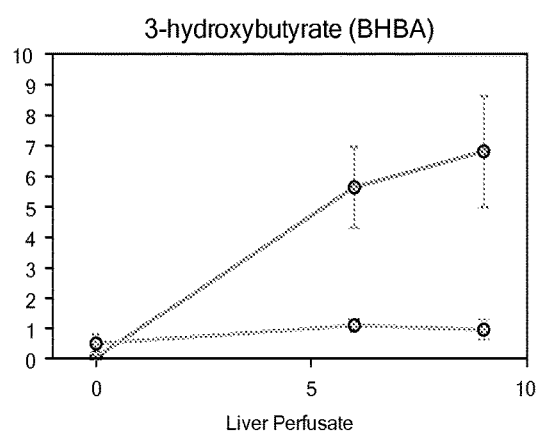
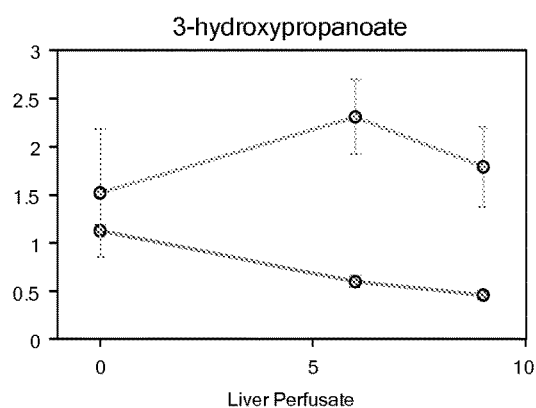
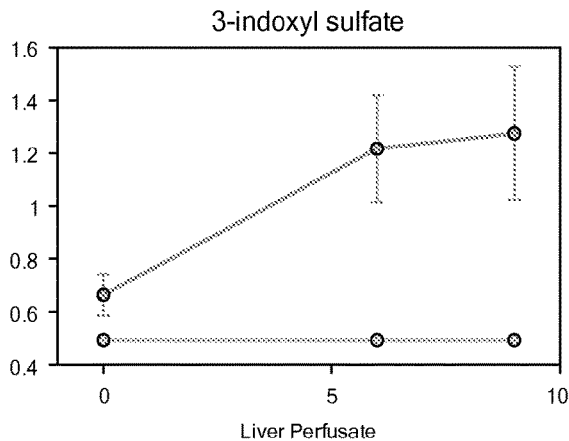
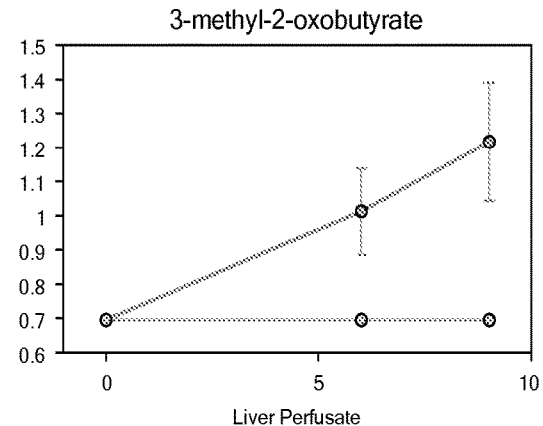

FIG. 19C
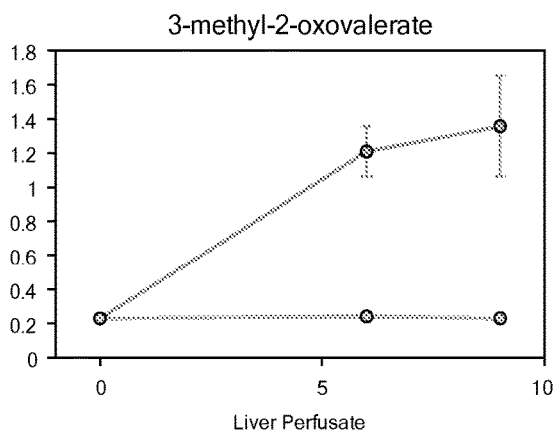
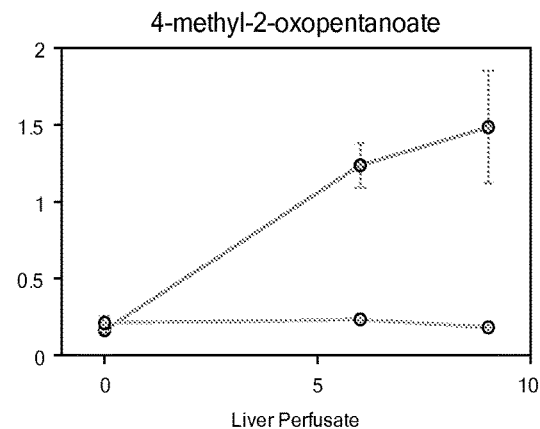
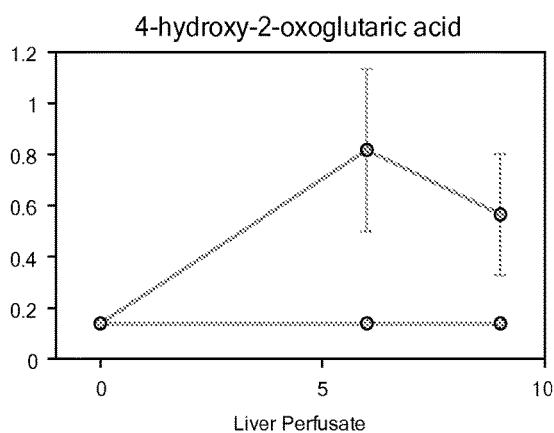
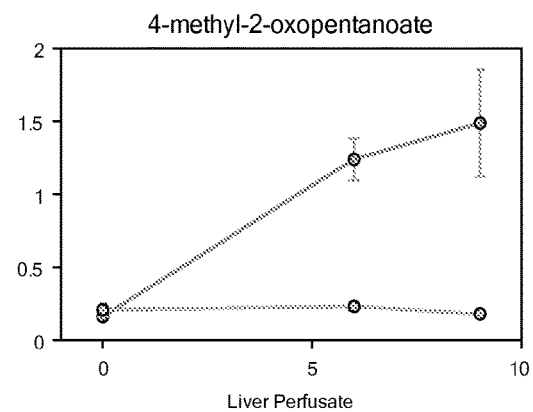
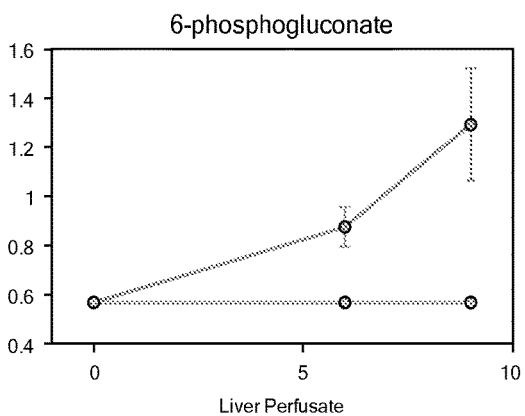
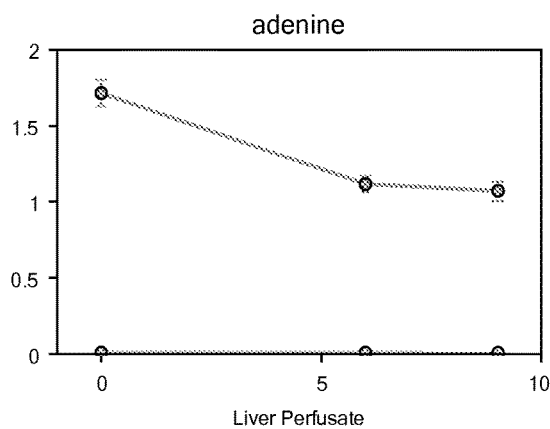

FIG. 19D
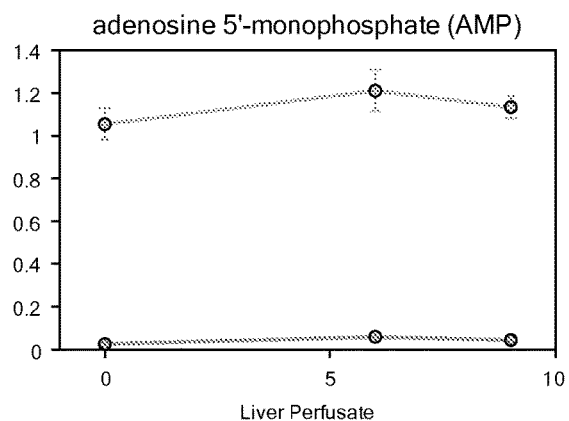
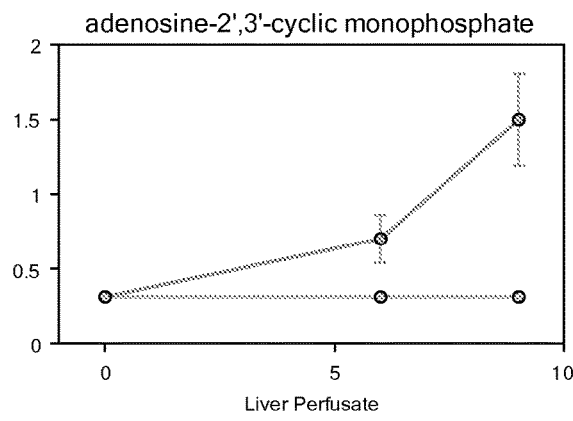
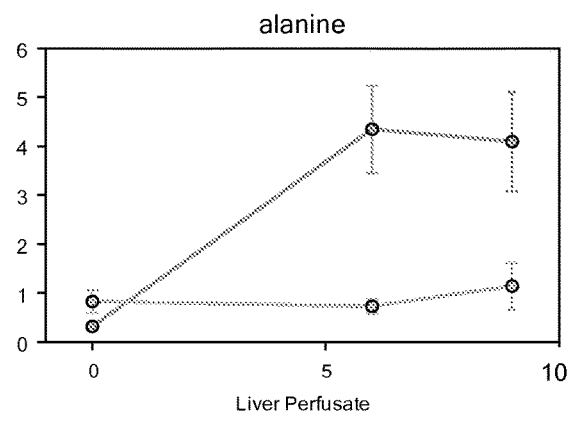
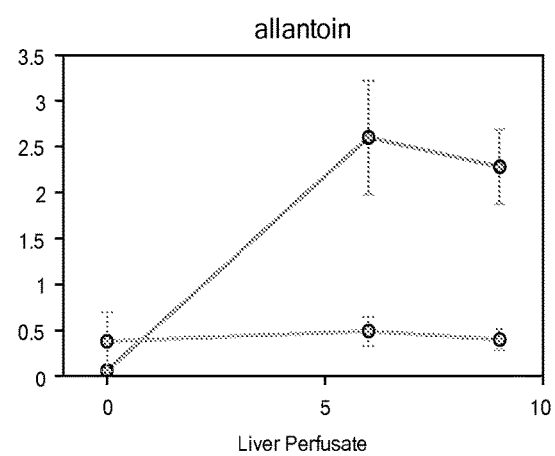
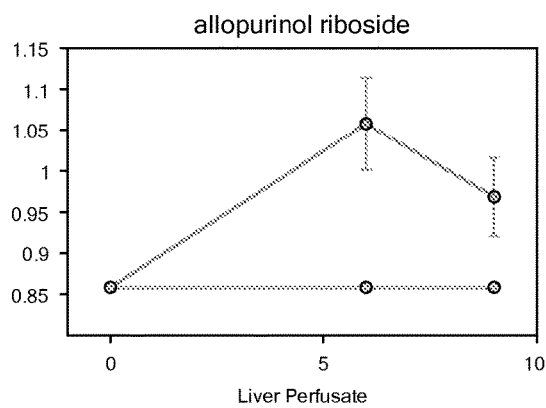
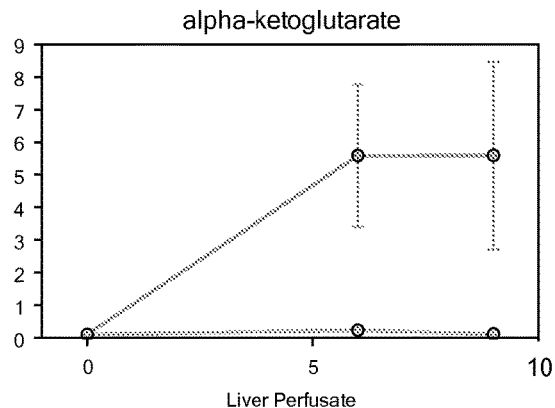

FIG. 19F
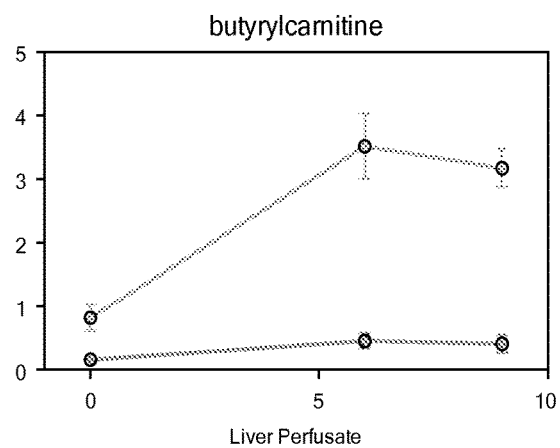
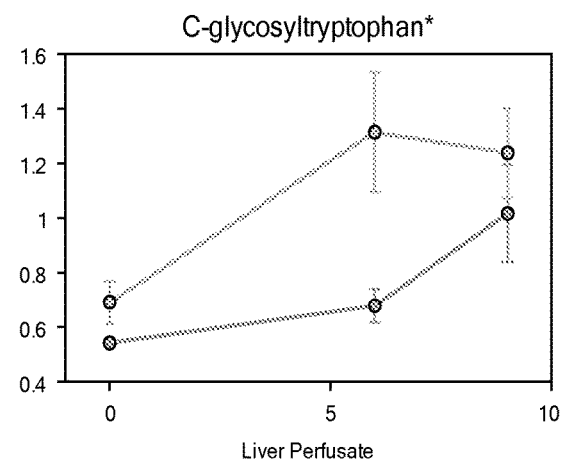
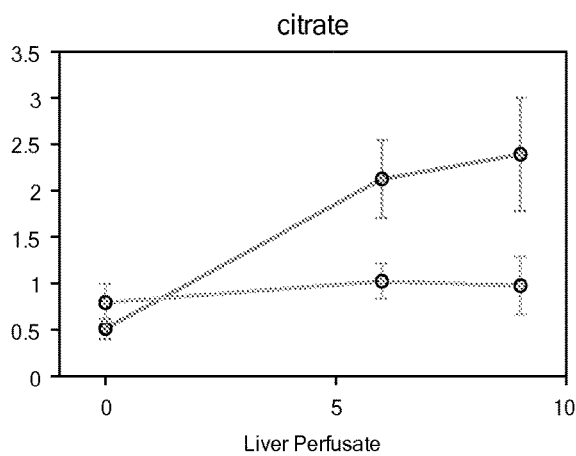
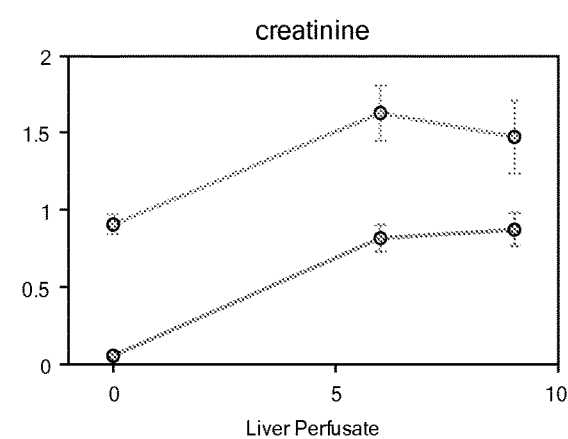
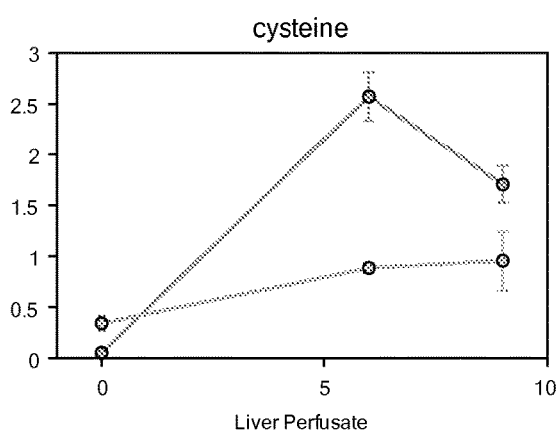
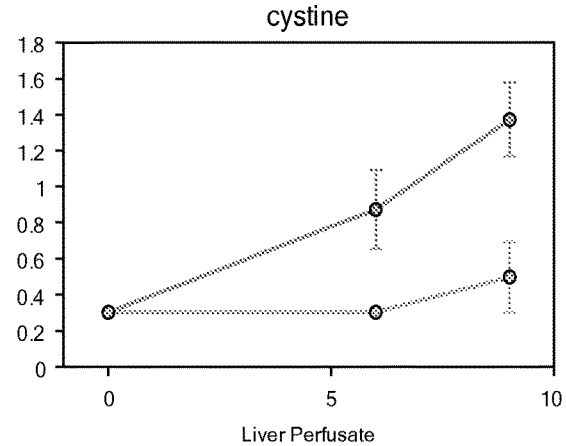

FIG. 19M
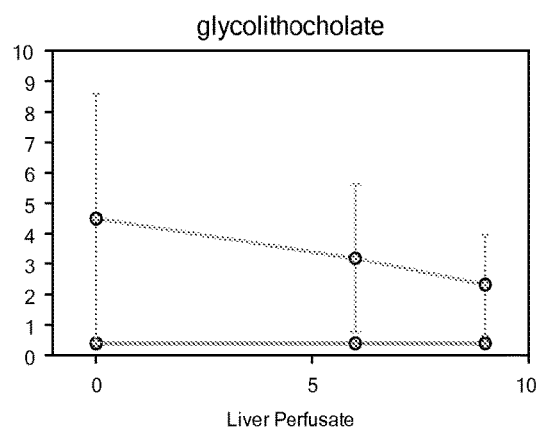
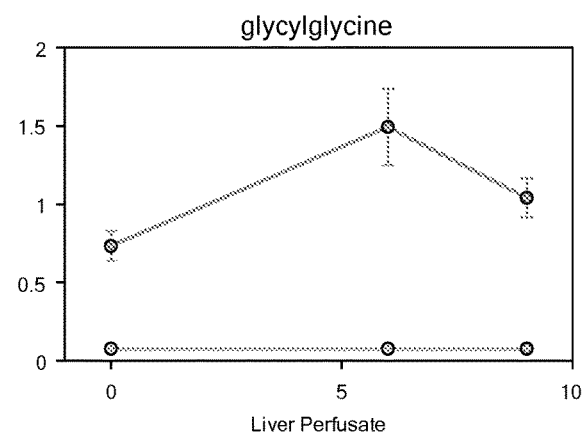
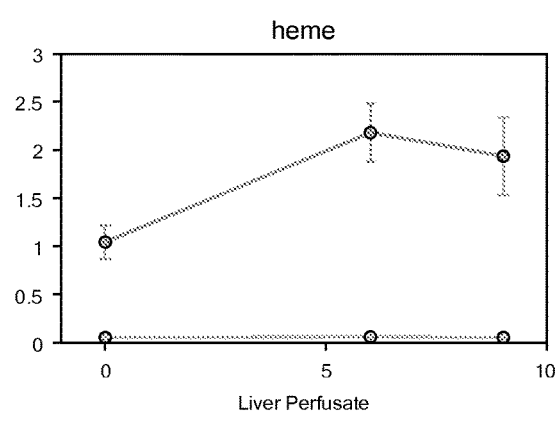
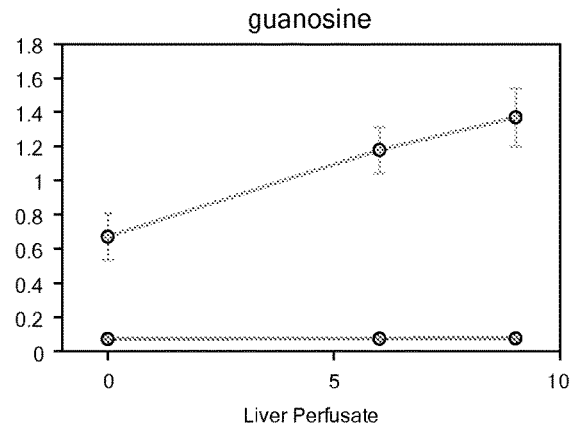
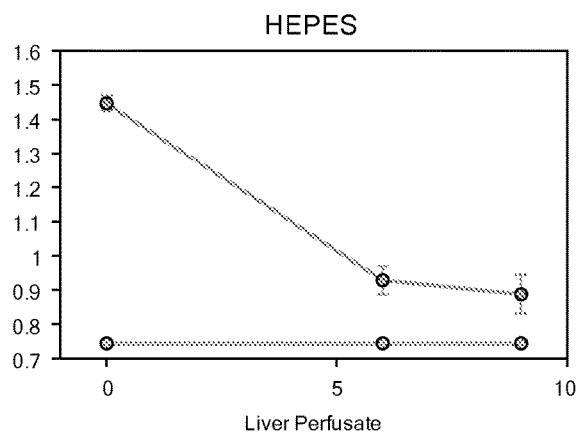
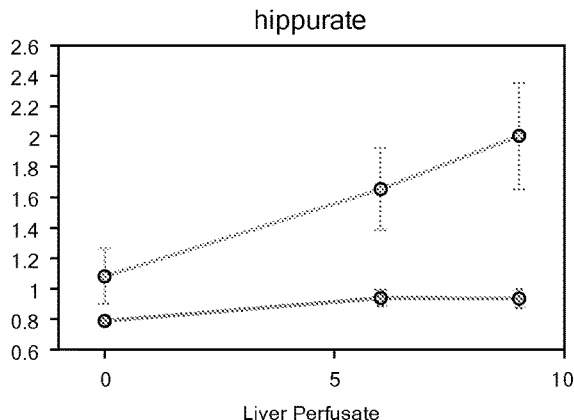

FIG. 19Q
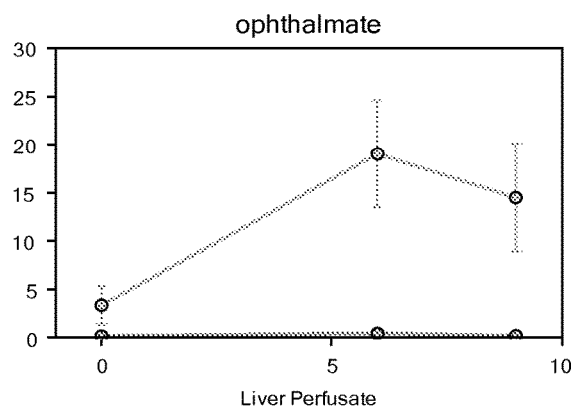
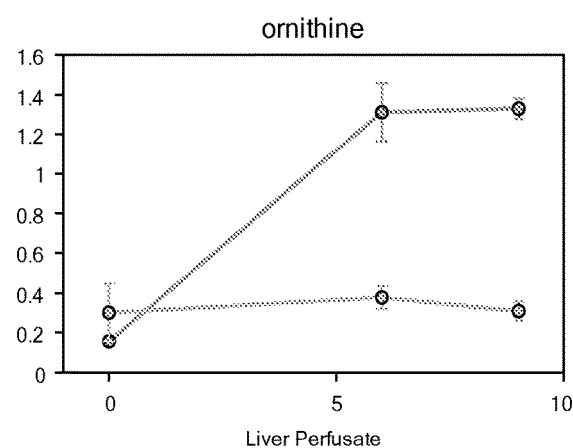
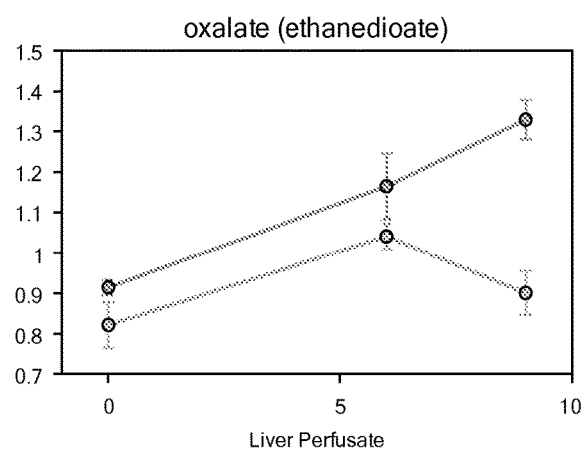
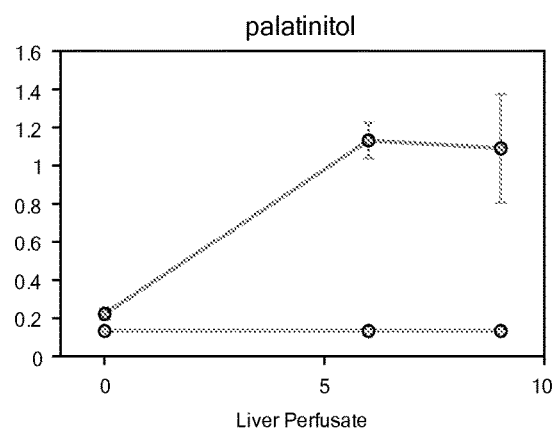
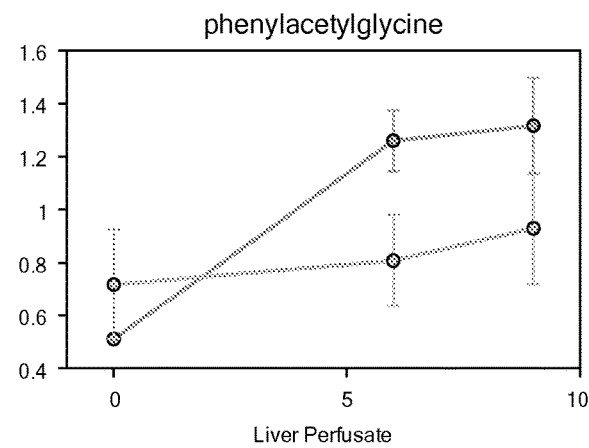
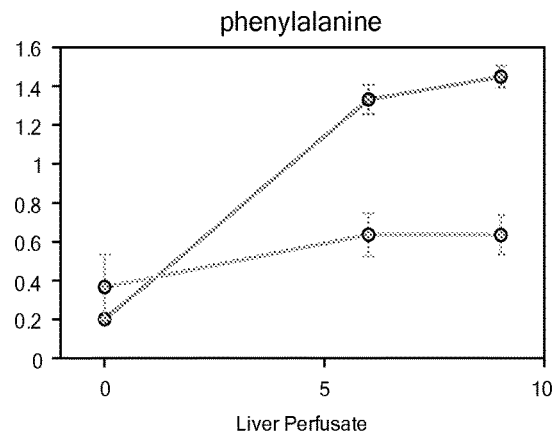

FIG. 19W
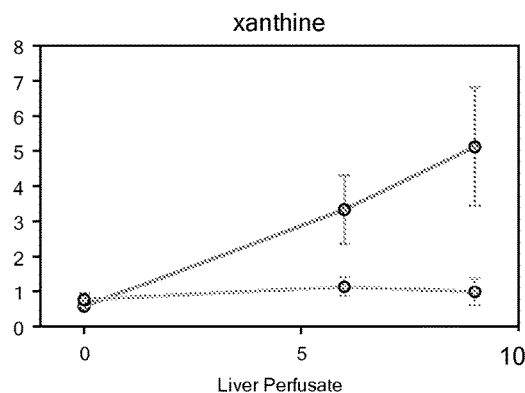
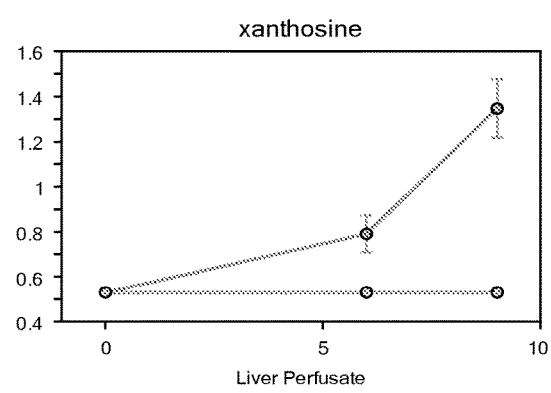
FIG. 20A
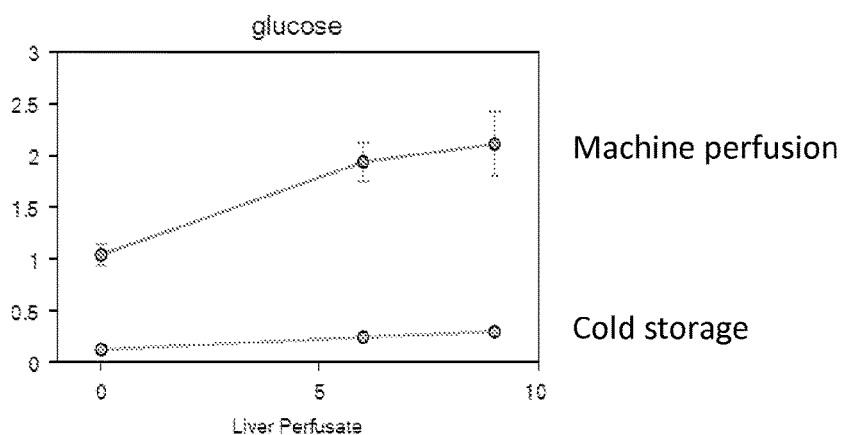
FIG. 20B
FIG. 20C
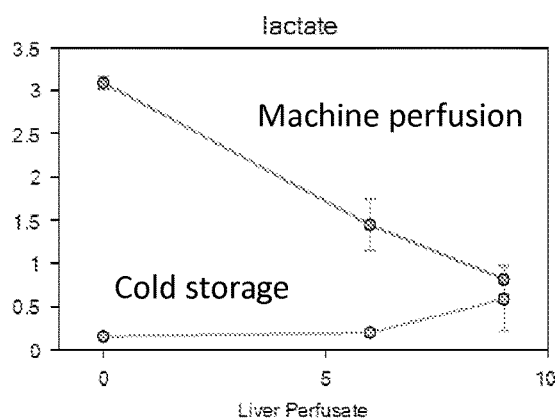
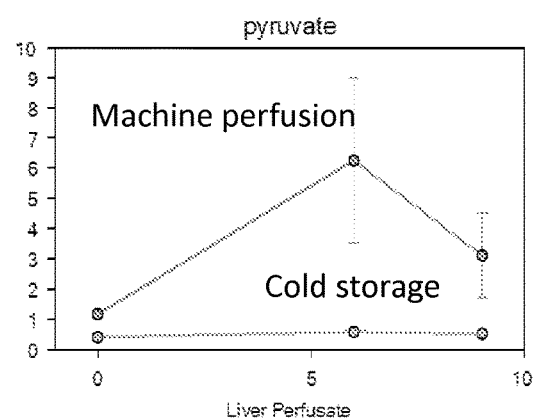

Dynamic Bayesian Networks (DBN)

US 10,634,686 B2

BIOMARKERS RELATED TO ORGAN FUNCTION

CROSS REFERENCE TO RELATED APPLICATION

This is the § 371 U.S. National Stage of International Application No. PCT/US2014/057049, filed Sep. 23, 2014, which was published in English under PCT Article 21(2), which in turn claims the benefit of U.S. Provisional Application No. 61/881,333, filed Sep. 23, 2013, which is incorporated by reference herein it its entirety.

FIELD

This disclosure relates to biomarkers related to organ or tissue function, particularly methods of identifying such biomarkers utilizing an ex vivo perfusion system and methods of predicting organ or tissue function by determining one or more biomarkers.

BACKGROUND

There are a large and increasing number of individuals in need of organ transplantation. Transplant candidates' waiting times have continued to grow around the world, imposing further morbidity and mortality for this population. Meanwhile, the discard rates of human organs have continued to increase in spite of the high mortality rate on the transplant waiting lists (18 patients/day) across the country. Even when an appropriate transplant organ is obtained, failure rates of transplanted organs range from 5-25%. Furthermore, organ dysfunction (such as liver or kidney dysfunction) is becoming increasingly common in the general population. Thus there is a need to identify biomarkers for organ dysfunction, for both organs for transplantation and in individuals who have or are at risk for organ dysfunction.

SUMMARY

Disclosed herein are methods of identifying biomarkers (such as nucleic acids (e.g., DNA, RNA or mRNA), proteins, and/or small molecules) that can be used to predict organ or tissue function or dysfunction. In some embodiments, the methods include ex vivo perfusion of the organ or tissue, collection of samples from the organ or tissue (for example, perfusate, fluids produced by the organ (such as bile or urine) or tissue biopsies) and measuring the level of one or more biomarkers in the sample. In some embodiments, the organ is perfused with a hemoglobin-based oxygen carrier (HBOC) solution. The organ function (or dysfunction) is analyzed and biomarkers associated with organ function or dysfunction are identified. In some examples, one or more biomarkers that increase or decrease in organs with good function (for example compared with a reference or control) are identified as predictors of organ function. In other examples, one or more biomarkers that increase or decrease in organs with poor function (for example, compared with a reference or control) are identified as predictors of organ dysfunction.

It is also disclosed herein that an analysis of biomarkers (such as nucleic acids (e.g., DNA, RNA or mRNA), proteins, and/or small molecules) present in a biological sample from an organ, tissue, or subject can be used to identify whether the organ, tissue, or subject is at risk for (or has) organ dysfunction or organ failure. In some embodiments, the methods utilize analyzing gene expression profiles, protein profiles, and/or small molecule profiles of metabolites. In other embodiments, the methods utilize analyzing the presence of one or more specific genes, proteins, and/or metabolites. These methods can be used, for example, to identify individuals at risk of (or having) organ dysfunction or failure or identify organs that are suitable or unsuitable for organ transplantation. In particular disclosed examples, the methods determine biomarkers associated with liver dysfunction (such as liver failure) and can be used to assist in the identification of persons with liver disease, to assess the severity of liver disease and the necessity of liver transplantation, and to help identify or rank donated livers in terms of their suitability for transplantation and/or likelihood of long-term organ survival following transplantation.

The foregoing and other features of the disclosure will become more apparent from the following detailed description, which proceeds with reference to the accompanying figures.

BRIEF DESCRIPTION OF THE DRAWINGS

FIG. 4A shows respiratory control ratio, FIG. 4B shows ATP production, and FIG. 4C shows reactive oxygen species generation ($H_2O_2$).

FIG. 7 shows pathway analysis (Ingenuity®) of genes with altered expression in the machine perfusion group (top) or cold ischemia group (bottom) at the fifth post-operative day (end-study necropsy) from microarray analysis of 20,000 genes. The machine perfusion group showed that genes associated with liver damage were significantly down-regulated, while the cold ischemia group showed significant up-regulation of genes associated with liver pathology.

FIG. 8 is a graphic representation of the transcriptomic analysis (microarray) of 20,000 genes obtained from pig liver samples showing the enrichment by biological process networks following 8 hours of machine perfusion (Ingenuity®).

FIG. 9A is a graphic representation of the transcriptomic analysis (microarray) of 20,000 genes obtained from pig liver samples showing the metabolic network analysis (Ingenuity®) following 8 hours of machine perfusion. Effective ex-vivo oxygenation enhanced significantly (p=0.01) the genes regulating drug, amino acid, free radical scavenging, vitamin, mineral and carbohydrate metabolism while enhancing energy production.

FIG. 17A shows valine, FIG. 17B shows leucine, and FIG. 17C shows isoleucine. The X-axis shows concentration in I/U. The Y-axis shows 3 time points (0=3 hours, 5=6 hours and 10=9 hours) when samples were obtained.

FIG. 18A shows alpha-ketoglutarate, FIG. 18B shows citrate. The X-axis shows concentration in I/U. The Y-axis shows 3 time points (0=3 hours, 5=6 hours and 10=9 hours) when samples were obtained.

FIGS. 20A-20E are a series of graphs showing compounds of the gluconeogenesis pathway in machine perfused livers and cold storage livers over the course of the experiment (hours). FIG. 20A shows glucose, FIG. 20B shows lactate, FIG. 20C shows pyruvate, FIG. 20D shows fructose 6-phosphate, and FIG. 20E shows glucose 6-phosphate. The X-axis shows concentration in I/U. The Y-axis shows 3 time points (0=3 hours, 5=6 hours and 10=9 hours) when samples were obtained.

DETAILED DESCRIPTION

Figure 1:
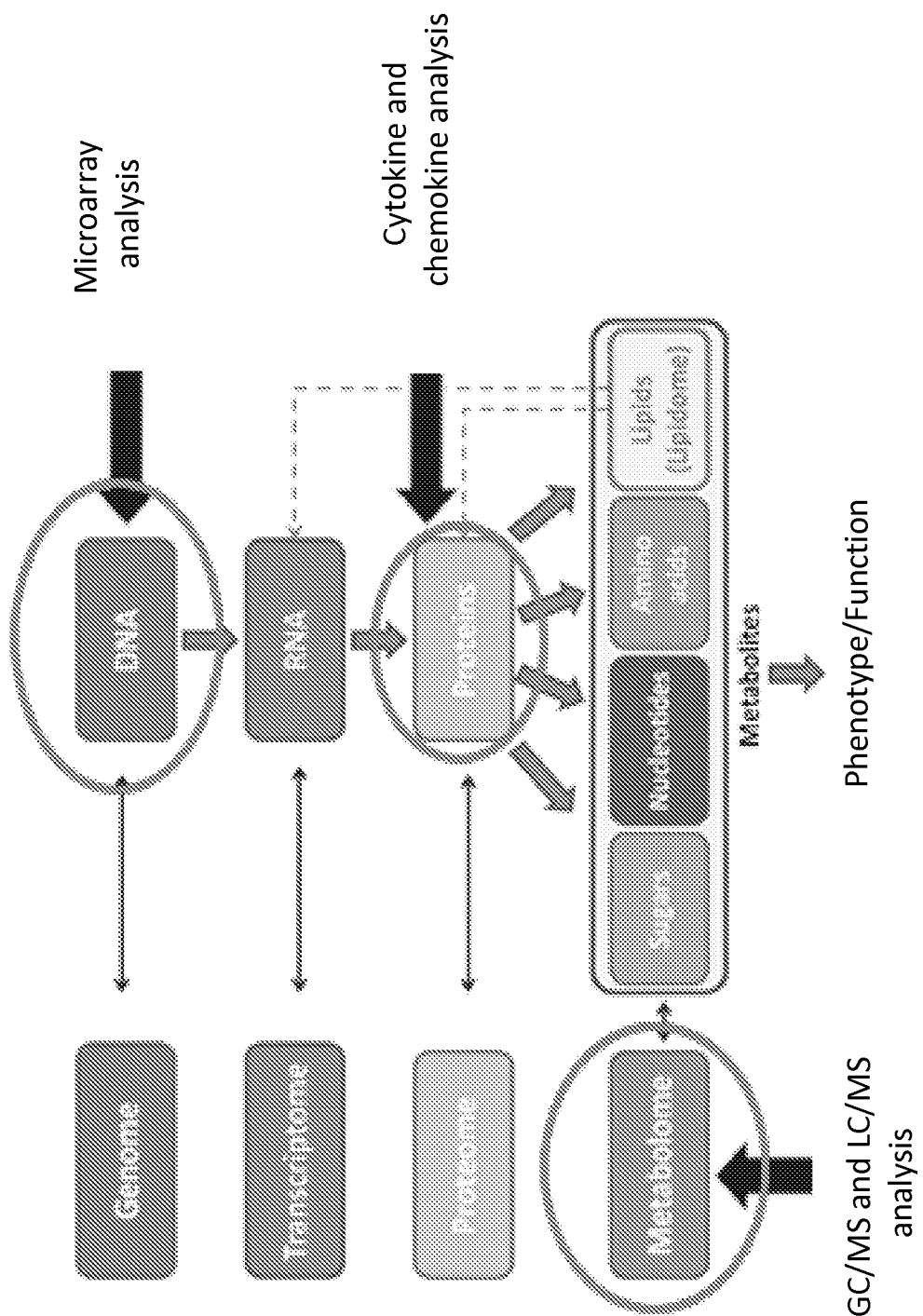
FIG. 1 is a schematic diagram showing an exemplary methodology for biomarker analysis in an ex vivo perfusion model.
Figure 2A:
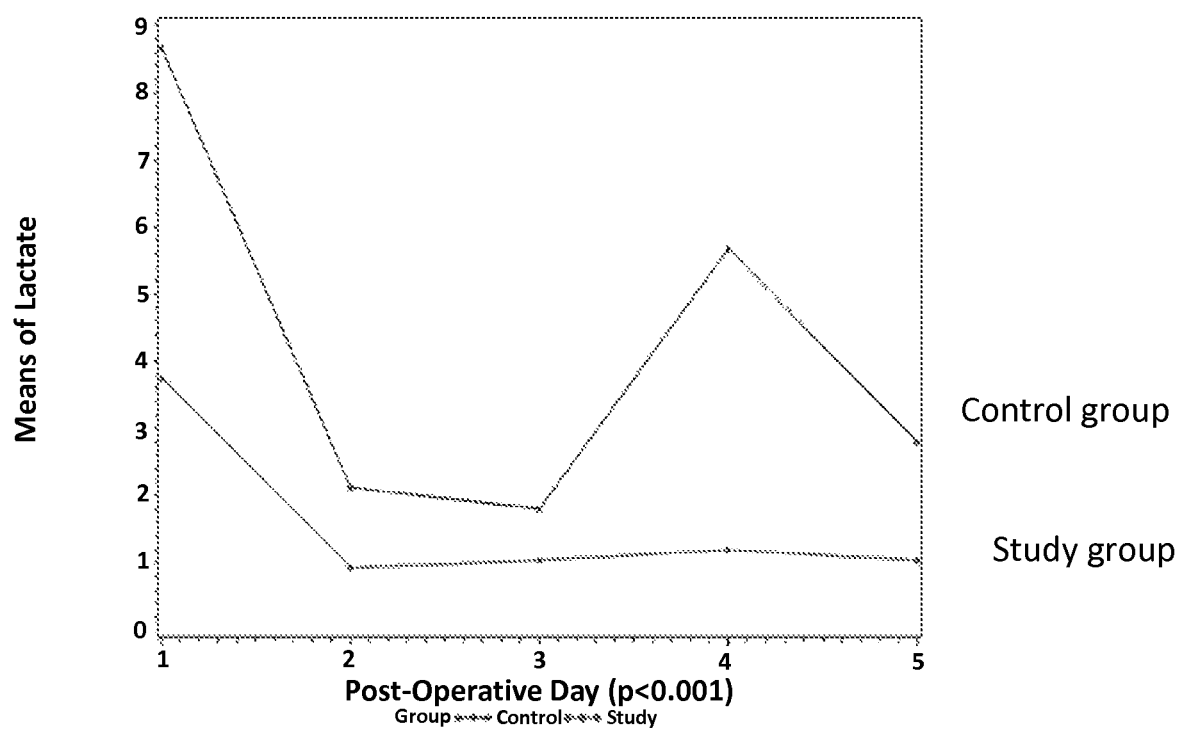
FIGS. 2A-2G are a series of graphs showing post-operative levels of lactate (FIG. 2A), albumin (FIG. 2B), AST (FIG. 2C), ALT (FIG. 2D), BUN (FIG. 2E), creatinine (FIG. 2F), and peripheral blood pH (FIG. 2G) in the control and study group animals.
Figure 2B:
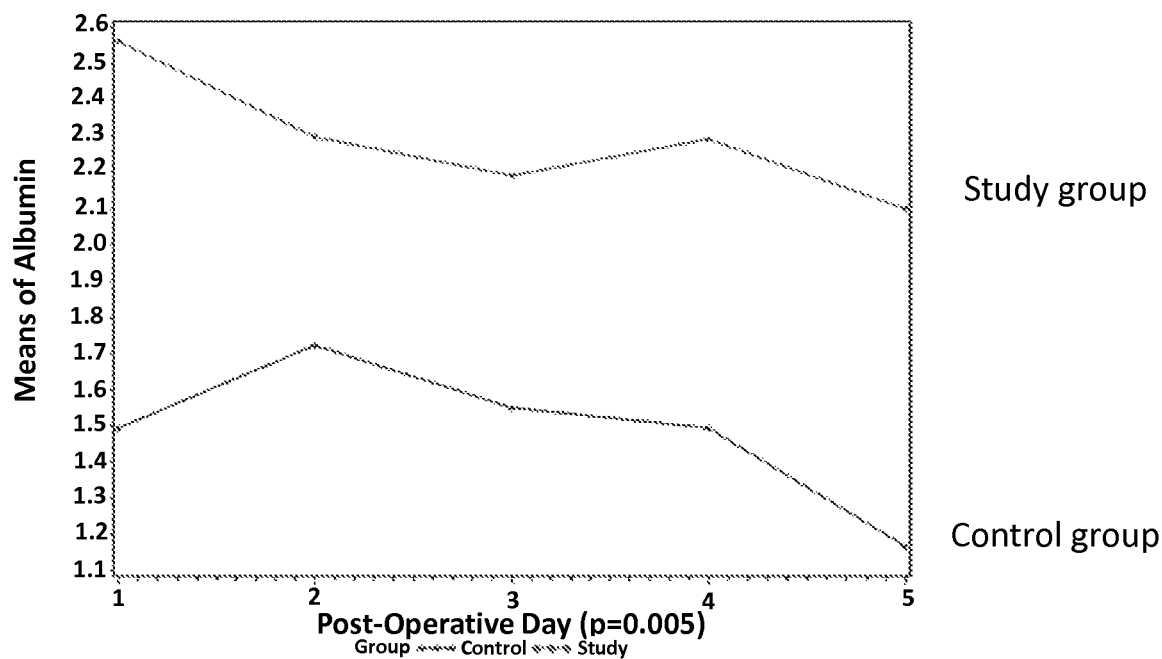
Figure 2C:
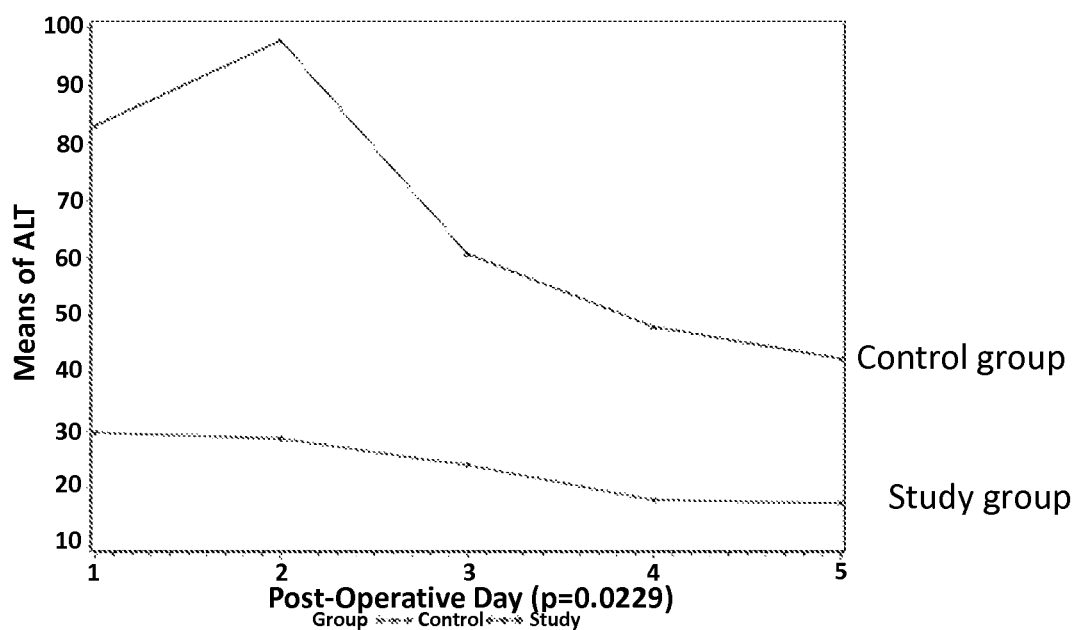
Figure 2D:
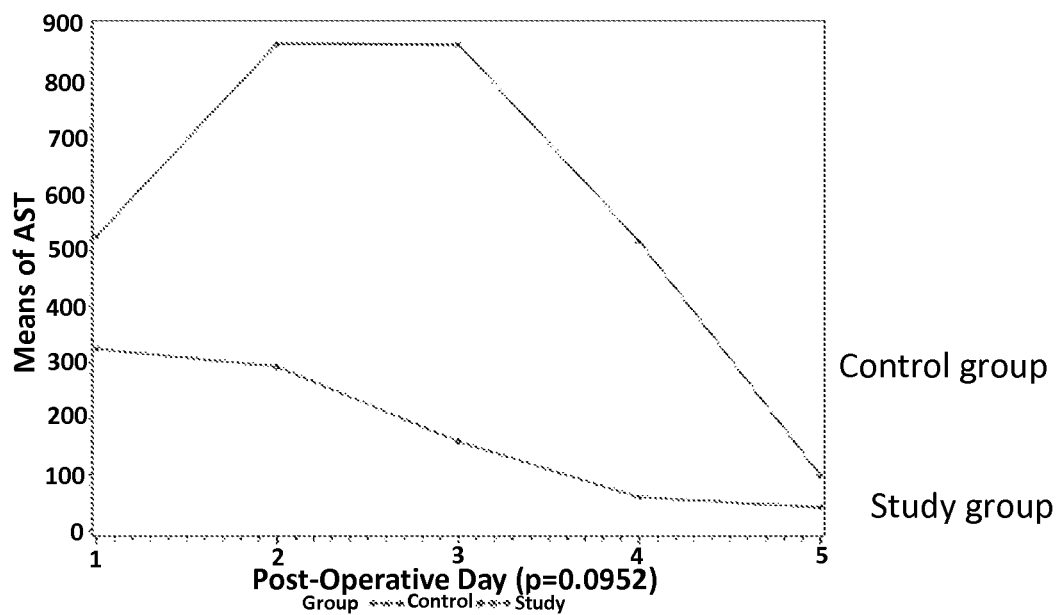
Figure 2E:
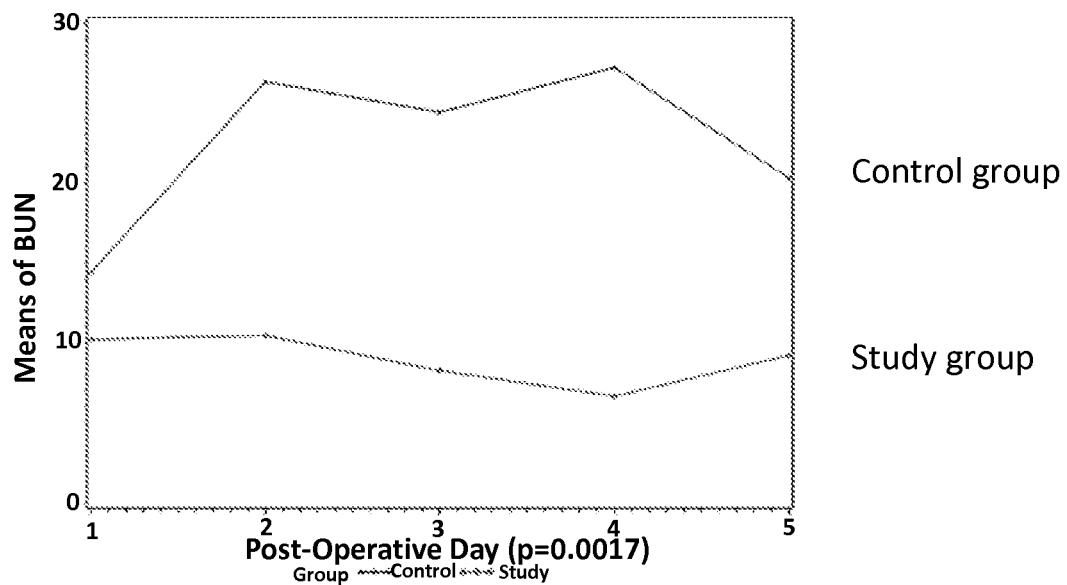
Figure 2F:
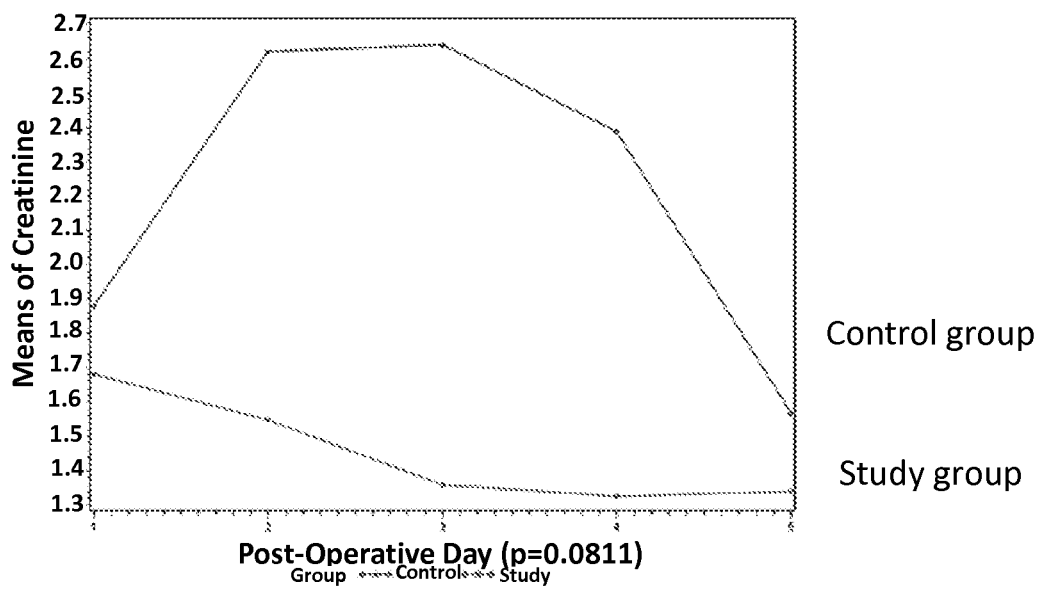
Figure 2G:
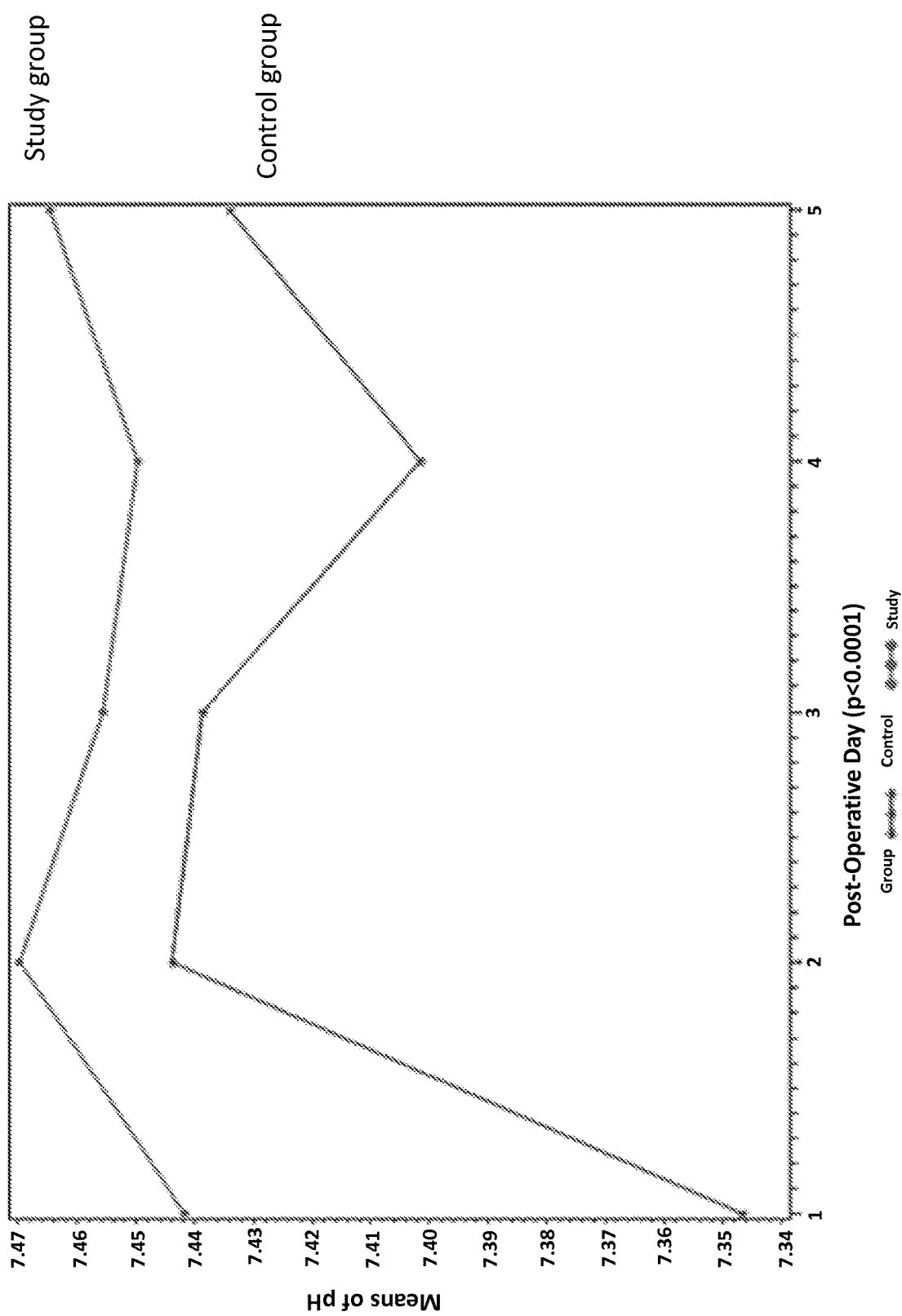

Disclosed herein is a new discovery platform for biomarkers related to organ or tissue function, particularly methods of identifying such biomarkers utilizing an ex vivo perfusion system where organs can be perfused outside of the body for several hours by a system combining machine perfusion with a cell free oxygen carrier solution at variable temperatures. This system providing effective oxygenation through ex vivo perfusion for several hours can be utilized to assess tissue and organ viability (for both acute and long term features) while determining the role of biochemical components (e.g., transcriptomics, cytokines, chemokines, damage-associated molecular pattern molecules (DAMPs), toll-like receptors (TLRs) and/or metabolomics) in predicting subsequent organ function.

This system can also map out biological features related to a previously known disease (diabetes, hypertension, steatosis, acute kidney injury, etc.) experienced by a subject, whose organs can be further studied post-mortem by this new ex vivo perfusion environment. This should create a new platform to define cardinal events for acute (e.g., initial markers involved in acute organ failure) and chronic diseases (e.g., initial cell signaling for the development of fibrosis) that are currently limited by the subject's survival. Finally, this technology represents a new model system, for testing new therapies and diagnostics for acute diseases of solid organs.

The current platforms utilized for the discovery of clinically-relevant biomarkers related to organ function and additional medical conditions are primarily based on biological samples (e.g., blood, urine, bile, saliva, etc.) obtained from live individuals. Biomarkers can be divided in pharmacodiagnostic, pharmacological, and disease related categories. These biochemicals are essential tools in preventive and personalized medicine, modern drug development, and in outcomes prediction for medical treatment and/or diseases.

Predictive biomarkers are the building blocks for personalized medicine when capable to enhance the evidence-based environment needed for subsequent diagnostic and therapeutic decisions. These new biomarkers should reflect the heterogeneity of human diseases while stratifying patients and biological pathways within their predictable outcomes. The early discovery and exploratory phases involving the inception of new biomarkers are rather lengthy and expensive, since the initial data collection relies primarily on live patients and their body fluids in a rather diverse geographic and clinical environment.

This disclosure describes a new platform for the development of biomarkers that is primarily centered on organs and tissues being perfused by machine perfusion technology in association with a recently developed cell-free oxygen carrier solution (discussed below). This ex vivo discovery platform for biomarkers can also be used to predict organ function prior to organ transplantation. Finally, developing new therapies for acute diseases has been challenging because existing model systems involving animals (even transgenic animals) and cell cultures often do not yield results that translate into humans. The platform disclosed herein offers a unique solution to this problem by using human organs and subjecting them to a variety of acute pathologies including infection, trauma and ischemia in order to study treatments and diagnostics.

In some embodiments, biomarkers can be identified for pharmacodiagnostic applications (e.g., treatment eligibility, treatment response prediction, drug safety, and/or assessing the efficacy of a given therapy), pharmacological applications (e.g., pharmacodynamics markers, pharmacokinetic markers, and/or outliners of intrinsic mechanisms of action), disease and medical conditions (e.g., screening for a given condition, early prognostic feature, early detection, monitoring tool to detect clinical evolution and recurrence of a given disease), and/or organ transplantation (e.g., predictive marker for organ function, predictive marker for ischemia-reperfusion injuries, predictive factor for immune compatibility, predictive of vascular integrity, and/or predictive of subsequent fibrosis development within the allograft).

I. Terms

In order to facilitate review of the various embodiments of this disclosure, the following explanations of specific terms are provided:

Biomarker: An organic biomolecule, such as a small molecule, amino acid, sugar, carbon (energy) source, carbohydrate, nucleic acid (such as DNA, RNA, or mRNA, referred to in some examples herein as "genes") or a polypeptide or protein, which is differentially present in a biological sample. In one example, the biomarker is present in a sample taken from an organ or tissue or a subject who is, or may be at risk for, or has, organ dysfunction. A biomarker can be differentially present in samples from a normal (e.g., healthy or functional) organ, tissue, or subject and samples from an organ, tissue, or subject having or at-risk for organ dysfunction, if it is present at an elevated level or a decreased level in the latter samples as compared to normal samples.

Hemoglobin-based oxygen carrier (HBOC): Molecules or compositions with oxygen carrying capabilities derived from the presence of hemoglobin. In some examples, HBOCs include isolated or purified hemoglobin (sometimes referred to as "acellular" HBOCs). Exemplary acellular HBOCs contain polymerized hemoglobin (for example, bovine or human hemoglobin), for example HBOC-201 (HEMOPURE, OPK Biotech, Cambridge, Mass.), HEMOLINK (Hemosol, Inc., Toronto, Canada), and POLYHEME (Northfield Laboratories, Evanston, Ill.) or encapsulated hemoglobin (such as liposome- or polymersome-encapsulated hemoglobin). In other examples, HBOCs include red blood cells.

Metabolome: All of the small molecules present in a given sample, tissue, organ, or subject. The metabolome includes both metabolites as well as products of catabolism. In one embodiment, the disclosure encompasses a small molecule profile of the entire (or substantially entire) metabolome of a sample. In other embodiments, the disclosure encompasses a profile of one or more molecules of the metabolome of a sample. Generally the metabolome or small molecule profile includes those molecules with a molecular weight of less than 2,000 Daltons Small molecules do not include large macromolecules, such as proteins (for example, proteins with molecular weights over 2,000, 3,000, 4,000, 5,000, 6,000, 7,000, 8,000, 9,000, or 10,000 Daltons), large nucleic acids (such as nucleic acids with molecular weights of over 2,000, 3,000, 4,000, 5,000, 6,000, 7,000, 8,000, 9,000, or 10,000 Daltons), or large polysaccharides (such as polysaccharides with a molecular weights of over 2,000, 3,000, 4,000, 5,000, 6,000, 7,000, 8,000, 9,000, or 10,000 Daltons). The molecules shown in FIG. 1-A-19W and Tables 8 and 9 are non-limiting examples of small molecules of the metabolome.

Organ: A part of the body, tissue, or portion thereof. In some examples, organs include those that can be transplanted or preserved ex vivo. Organs include, but are not limited to liver, kidney, heart, lung, pancreas, small intestine, and limb (such as arm or leg, or portion thereof), or extremity (such as hand, foot, finger, toe, or a portion thereof). As used herein, "organ" also includes other tissues, such as tissue grafts, such as composite tissue allografts.

Organ dysfunction: Organ dysfunction is a biological and dynamic condition where an organ does not perform its expected function (e.g., has impaired function). Organ dysfunction can migrate towards organ failure if remained untreated. Organ dysfunction can lead into the deregulation of the body homeostasis when metabolically active and filtering organs like liver and kidneys are affected. One example of kidney dysfunction is in drug toxicity leading into renal failure (e.g., excessive use of NSAIDS). In some examples, kidney dysfunction includes decreased glomerular filtration rate due to progressive vasospasm of afferent arterioles within the nephron. An example of liver dysfunction is in metabolic syndrome following morbid obesity. In some examples, liver dysfunction includes enhanced metabolic pathways to gluconeogenesis, followed by fat deposition within hepatocyte cytoplasm, leading to hepatic steatosis.

Perfusion: Circulation of a fluid (also referred to as a perfusion solution or perfusate) through an organ to supply the needs of the organ to retain its viability (for example, in an ex vivo system). In some examples, the perfusion solution includes an oxygen carrier (for example, a hemoglobin-based oxygen carrier). Machine perfusion refers to introduction and removal of a perfusion solution to an organ by a mechanical device. Such devices may include one or more chambers for holding an organ and a perfusion solution, one or more pumps for delivery of the perfusion solution to the organ, one or more means to regulate temperature of the perfusion solution, and one or more means to oxygenate the perfusion solution. In some examples, machine perfusion includes introduction of an oxygen carrying fluid into an organ and removal of oxygen depleted fluid from the organ by circulation of the oxygen carrying fluid through the organ.

Sample: A specimen containing genomic DNA, RNA (including mRNA), protein, small molecules or combinations thereof, obtained from an organ, tissue, or subject. In some examples, a sample is from an ex vivo tissue or organ, such as perfusate from an ex vivo perfused tissue or organ, fluids produced by an organ or tissue (such as bile, urine, or tissue exudate), or a biopsy from an organ or tissue. Additional examples include, but are not limited to, peripheral blood, bile, urine, saliva, tissue biopsy, fine needle aspirate, surgical specimen, and autopsy material from a subject.

Subject: Living multi-cellular vertebrate organisms, a category that includes human and non-human mammals, such as veterinary subjects.

II. Methods of Identifying Biomarkers of Organ or Tissue Function

Disclosed herein are methods of identifying biomarkers (such as genes (e.g., RNA or mRNA), proteins, and/or small molecules) that can be used to predict organ or tissue function or dysfunction. An advantage of the methods disclosed herein is that samples are obtained from ex vivo tissues or organs, which do not have interference from blood products or cells and does not implicate further allosensitization of the tissue or organ under perfusion. An additional advantage of the methods disclosed herein is that organs that are not suitable for transplantation and would otherwise be discarded can be utilized to identify biomarkers of organ dysfunction. In particular embodiments described herein, the organ is a liver; however, any perfusable organ or tissue (such as liver, kidney, lung, heart, pancreas, small intestine, limbs (for example, arm or leg), extremities (for example, hand, foot, finger, toe, or face)), or a portion thereof can be utilized in the disclosed methods.

In some embodiments, the methods include ex vivo perfusion of the organ or tissue, collection of samples from the organ or tissue (for example, perfusate, fluids produced by the organ (such as bile or urine), or tissue biopsies) and measuring the level of one or more biomarkers in the sample. In some embodiments, the organ is perfused with a hemoglobin-based oxygen carrier (HBOC) solution. The organ function (or dysfunction) is analyzed and biomarkers associated with organ function or dysfunction are identified. In some examples, one or more biomarkers that increase or decrease in organs with good function (for example compared with a reference or control) are identified as predictors of organ function. In other examples, one or more biomarkers that increase or decrease in organs with poor function (for example, compared with a reference or control) are identified as predictors of organ dysfunction.

In particular embodiments, the methods include determining presence and/or amount of one or more biomarkers, such as one or more biomarkers from a genome, transcriptome, proteome, and/or metabolome of a tissue, organ, or subject, for example as shown schematically in FIG. 1. The function (or dysfunction) of the tissue or organ or the health status of the subject from which the sample was obtained is determined or monitored. Biomarkers that increase or decrease in a tissue, organ, or subject with good function, health, or a positive outcome are identified as predictors of organ or tissue function. Biomarkers that increase or decrease in a tissue organ, or subject with poor or decreased function, health, or a poor outcome are identified as predictors of organ or tissue dysfunction.

In particular examples, the methods include obtaining samples from an ex vivo perfused organ or tissue. The samples include one or more of perfusate, fluid produced by the organ or tissue (such as bile, urine, or tissue exudate), or tissue biopsy samples. The organ or tissue can be machine perfused by any method known to one of ordinary skill in the art. In some examples, the machine perfusion is carried out with a perfusion solution that includes an oxygen carrier, such as a hemoglobin-based oxygen carrier (HBOC). In one particular example, the machine perfusion is carried out with a perfusion solution that includes a modified HBOC solution comprising a 1:3 mixture of HEMOPURE (OPK Biotech, Cambridge, Mass.) and Belzer machine perfusion solution (BMPS) (e.g., Muhlbacher et al., *Transplant. Proc.* 31:2069, 1999; Kwiatkowski et al., *Transplant. Proc.* 33:913, 2001; Stubenitsky et al., *Transplant. Int.* 68:1469, 1999). The modified HBOC solution is described in detail in U.S. Prov. Pat. Appl. No. 61/713,284, filed Oct. 12, 2012, and International Pat. Publ. No. WO 2014/059316, both of which are incorporated herein by reference in their entirety. The disclosed solutions utilize a low fraction of oxygen carrier (such as hemoglobin, for example acellular hemoglobin), for example compared to that found in blood. However, this amount surprisingly has been found to provide adequate oxygen delivery and carbon dioxide removal for organ preservation at subnormothermic temperatures, while maintaining low levels of methemoglobin production. In addition, a low fraction of hemoglobin (such as cross-linked hemoglobin) reduces potential adverse effects of the presence of exogenous hemoglobin in the perfusate, including vasoactivity, nephrotoxicity, interference with macrophage function, antigenicity, indirect complement activation, and neurotoxicity. In some embodiments, the disclosed solutions contain about 3-10 g/dL of acellular hemoglobin (such as cross-liked bovine hemoglobin, for example glutaraldehyde cross-linked bovine hemoglobin), such as about 3-9 g/dL, about 3-8 g/dL, about 3-7 g/dL, about 3-6 g/dL, about 3-5 g/dL, or about 3-4 g/dL. In some examples, the solution contains about 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, or 10 g/dL cross-linked hemoglobin. In particular embodiments, the solutions include about 3-4 g/dL cross-linked bovine hemoglobin. In one non-limiting example, the solution includes about 3.25 g/dL cross-linked bovine hemoglobin. As discussed above, the disclosed perfusion solutions have a pH of about 7.0-8.0 (such as about 7.2-7.9 or about 7.4-7.85) at room temperature, an osmolality of about 290-360 mOsm/kg (such as about 290-300 mOsm/kg), and a COP of about 18-75 mm Hg (such as about 35-65 mm Hg). In some embodiments, the solution has a pH (at room temperature) of about 7.0 to about 8.0, about 7.1 to about 7.9, about 7.2 to about 7.9, about 7.3 to about 7.8, about 7.4 to about 7.85, about 7.5 to about 7.75, about 7.6 to about 7.75, or about 7.6 to about 7.7. In particular non-limiting examples, the pH at room temperature is about 7.60, 7.61, 7.62, 7.63, 7.64, 7.65, 7.66, 7.67, 7.68, 7.69, or 7.70. In further embodiments, the osmolality of the solution is about 290-360 mOsm/kg, such as about 290-350, 290-330, 295-340, 300-310, 300-325, 310-350, 290-300, 290-299, 290-298, 290-297, 290-296, 295-300, 295-299, 295-298, 295-297, 295-296, 296-300, 296-299, or 298-300 mOsm/kg. In some examples, the osmolality of the solution is about 290, 290.5, 291, 291.5, 292, 292.5, 293, 293.5, 294, 294.5, 295, 295.5, 296, 296.5, 297, 297.5, 298, 298.5, 299, 299.5, or 300 mOsm/kg. In additional embodiments, the solution has a COP of about 18 to 75 mm Hg, for example about 20-70, 25-65, 30-70, 35-65, 35-60, 40-60, 40-50, 50-60, or 55-60 mm Hg. In some non-limiting examples, the COP of the solution is about 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 mm Hg. In some embodiments, the solution has a pH, osmolality, and COP selected from any one of the values provided herein. In one non-limiting example, the solution has a pH of about 7.6-7.7, an osmolality of about 295-297 mOsm/kg, and a COP of about 58-60 mm Hg, such as a pH of about 7.62, osmolality of about 296 mOsm/kg, and a COP of about 59 mm Hg. However, other machine perfusion solutions known to one of ordinary skill in the art can also be utilized.

In some examples, the methods can also include obtaining samples from an ex vivo organ or tissue that is not machine perfused, for example a tissue or organ that is treated by cold storage in a preservation solution. In one example, the cold storage preservation (CSP) solution is UW solution, which is the current standard of care for preservation of organs for transplantation. Organs preserved by CSP in UW solution frequently have poor function (dysfunction), as described in Example 1, below. In some examples, samples from CSP organs are controls for comparison with samples from machine perfused organs, which generally have better function and outcome (see Example 1, below).

The samples obtained from the tissue or organ are analyzed for presence and/or amount of one or more biomarkers. In some examples, the genome or transcriptome is analyzed to determine gene expression biomarkers, for example, samples are analyzed for presence and/or amount of one or more nucleic acids (such as DNA, RNA, mRNA, or miRNA). In particular examples, the nucleic acids analyzed are related to cell proliferation or cell differentiation.

In other examples, the samples are analyzed for presence and/or amount of one or more proteins or polypeptides, such as analysis of the proteome of the sample. In particular examples, the cytokine and/or chemokine profile of the sample is analyzed (for example, one or more of interferon-α, interferon-γ, interleukin-10, interleukin-12/23 (p40), interleukin-1b, interleukin-4, interleukin-6, interleukin-8, and/or tumor necrosis factor-α); however, any protein of interest can be analyzed. In additional examples, the proteins analyzed include hormones, clotting factors, paracrine factors, and/or growth factors. Exocrine secretions may also be analyzed, for example, exocrine secretions produced by the pancreas or the intestines. In one non-limiting example, hepatocyte growth factor is analyzed. In other examples, one or more of VEGF, TGF-β, ERK/MAPK, ErbB, FAK, HGF, p53, insulin receptor, PI3K/AKT, PDGF, FGF, EGF, and NF-κB are analyzed.

In particular examples, nucleic acid or protein biomarkers are analyzed in a tissue sample (such as a biopsy) from an organ, tissue, or subject. However, in some instances, nucleic acids or proteins can also be analyzed in perfusate from a machine perfused organ or tissue or in a fluid from an organ (such as bile or urine).

In further examples, the samples are analyzed for presence and/or amount of one or more small molecules, for example, analysis of the metabolome of the sample. In particular non-limiting examples, the small molecule profile is analyzed in perfusate from an ex vivo perfused organ, bile, or urine.

Methods of detecting presence and/or amount of nucleic acids, proteins, and small molecules are described in Section IV, below.

In some examples, the amount of the one or more biomarkers is compared with the amount of one or more biomarkers in a control or reference sample. In some examples, a "control" refers to a sample or standard used for comparison with an experimental sample, such as a sample or standard from one or more organs with known function or dysfunction. In some embodiments, the control is a sample obtained from a healthy organ. In some embodiments, the control is a historical control or standard reference value or range of values (such as a previously tested control sample, such as a group of samples that represent baseline or normal values, such as the level of one or more biomarkers in a healthy organ). In other embodiments, the control is a sample obtained from a dysfunctional organ. In some embodiments, the control is a historical control or standard reference value or range of values (such as a previously tested control sample, such as a group of samples that represent the level of one or more biomarkers in an organ with dysfunction).

One of skill in the art can identify healthy and/or dysfunctional organs. In some examples, organs (such as human organs) can be thoroughly examined for one or more metabolic features while under ex vivo machine perfusion in order to determine parameters of healthy or dysfunctional organs. The energy production pathways (e.g., glycolytic or glyconeogenic pathways) can by elucidated while outlining additional biological features on carbohydrate, lipid, amino acids, vitamin and minerals metabolism, as well as their free radical scavenging abilities. In one particular example, levels of lactate dehydrogenase, glutathione-S-transferase and aspartate transaminase are correlated with delay graft function of cadaveric kidney allografts (Bhangoo et al., *Nephrol Dial Transplant* 27:3305, 2012).

One of skill in the art can readily identify statistical methods and computer programs that can be used to identify an increase or a decrease (such as a statistically significant increase or decrease) in one or more biomarkers, including differences in molecule profiles. Methods of analysis that can be used include linear discriminant analysis and Random Forest analysis. Additional methods of analysis include Principal Component Analysis (PCA) and Dynamic Bayesian Networks (DBN). In some examples, these methods can be used to identify a principal component itself or variations as an increase or a decrease (such as a statistically significant increase or decrease) in one or more biomarkers. One of ordinary skill in the art can identify additional suitable methods of analysis to identify increases or decreases in biomarkers.

III. Methods of Predicting Organ Function or Dysfunction

Disclosed herein are methods for predicting organ function or dysfunction and methods of treating an organ or subject with predicted dysfunction. The methods include an analysis of biomarkers (such as genes (e.g., RNA or mRNA), proteins, and/or small molecules) present in a biological sample from an organ, tissue, or subject to identify whether the organ, tissue, or subject is at risk for (or has) organ dysfunction or organ failure. In some embodiments, the methods utilize analyzing gene expression profiles, protein profiles, and/or small molecule profiles of metabolites. In some examples a gene expression profile, protein profile, or small molecule profile includes 5 or more (such as 10, 15, 20, 25, 50, 100, 200, 500, 1000, or more) genes, proteins, or small molecule metabolites, respectively. In other embodiments, the methods utilize analyzing the presence of one or more (such as 2, 3, 4, 5, 10, 15, 20, 25, 30, 40, 50, 60, 70, 80, 90, 100, or more) specific genes, proteins, and/or metabolites. In particular embodiments, the profiles or particular biomarkers include one or more of the genes, proteins, and/or small molecules listed in any one of FIGS. 5-7, 10-23, 25, 26, and 28 and Tables 8 and 9, or any combination thereof. Exemplary methods of analyzing biomarkers from a sample are discussed in Section IV, below.

Figure 19E:
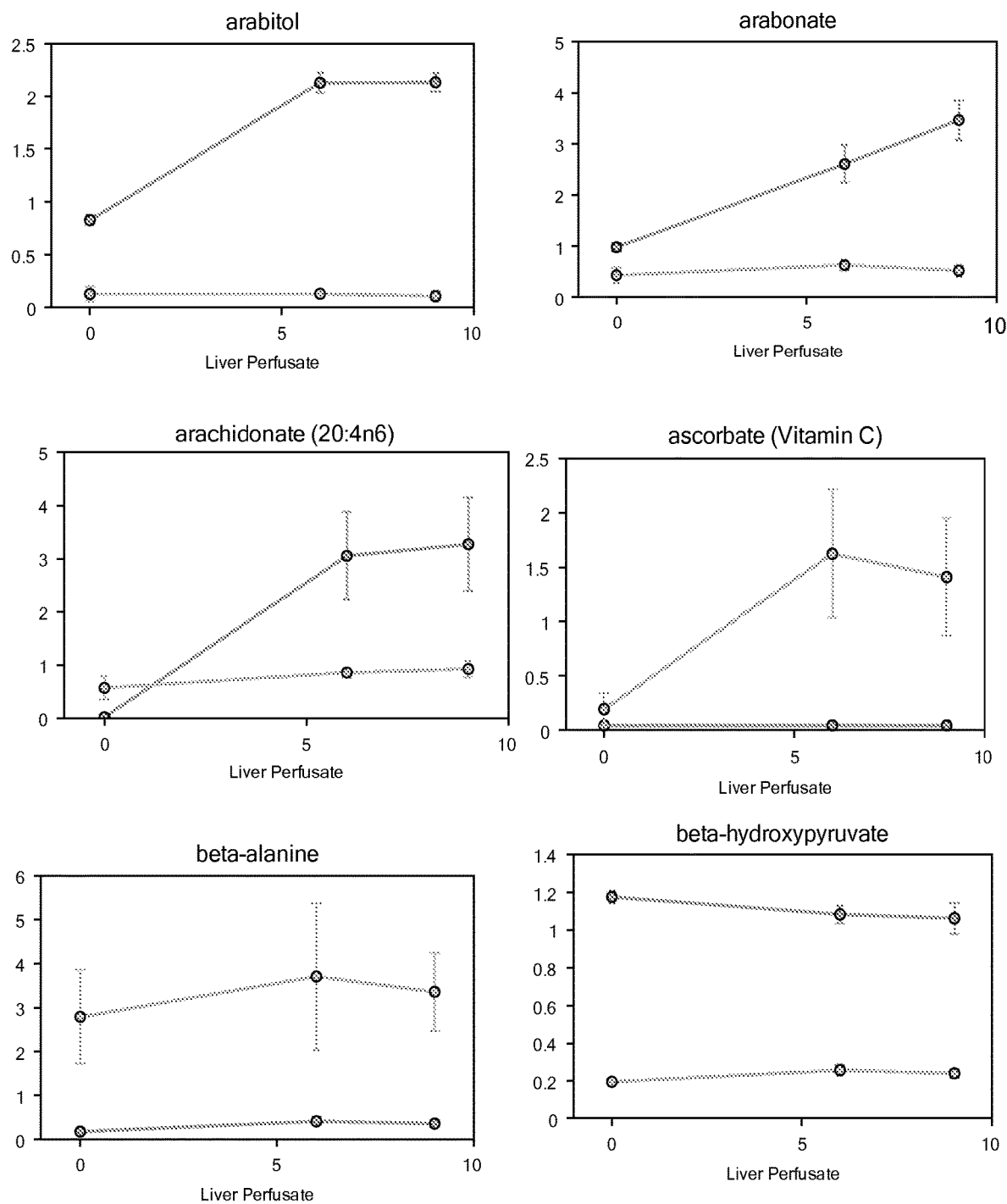
FIGS. 19A-19W are a series of panels of graphs showing different metabolites in machine perfused livers and cold ischemia livers over the course of the experiment (hours). The upper line in each plot is the machine perfused liver, except for 3-hydroxypropanoate, beta-alanine, butylcarnitine, C-glycosyltryptophan, creatinine, eiconsenoate (20:1n9 or 11), ethanolamine, galactose, GABA, gluconate, glutathione, oxidized (GSSG), glycerol 2-phosphate, glycerol 3-phosphate (G3P), glycerophosphorylcholine, glycohenodeoxycholate, glycocholate, glycohyodeoxycholic acid, glycolithocholate, guanosine, hippurate, hypotaurine, hypoxanthine, inosine, ketamine, ophthalmate, ribose 1-phosphate, ribose 5-phosphate, S-methylglutathione, spermine, sucrose, succinate, taurine, taurocholate, uridine, and verbascose, where the lower line is the machine perfused liver. The X-axis shows concentration in I/U. The Y-axis shows 3 time points (0=3 hours, 5=6 hours and 10=9 hours) when samples were obtained.
Figure 19G:
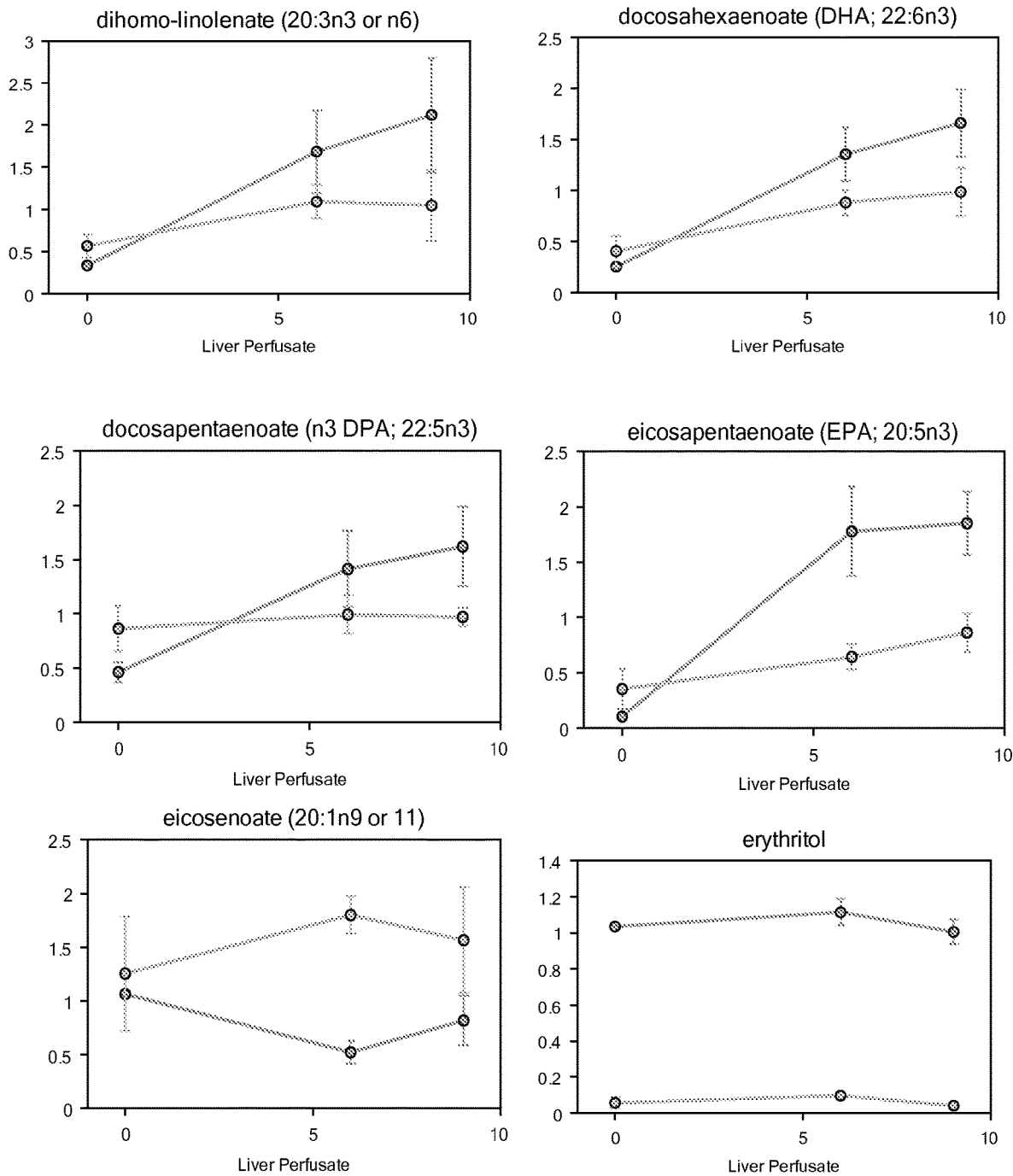
Figure 19H:
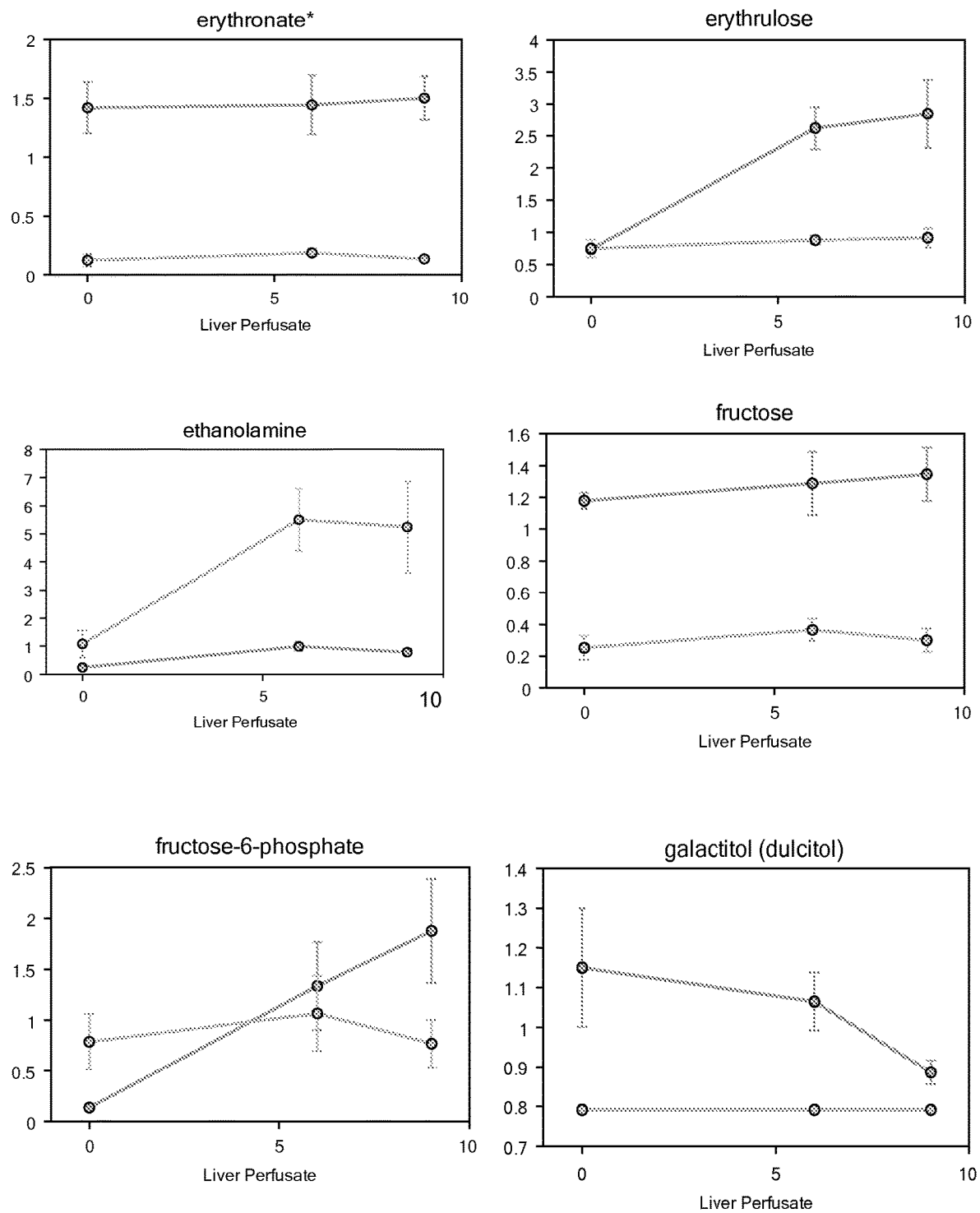
Figure 19I:
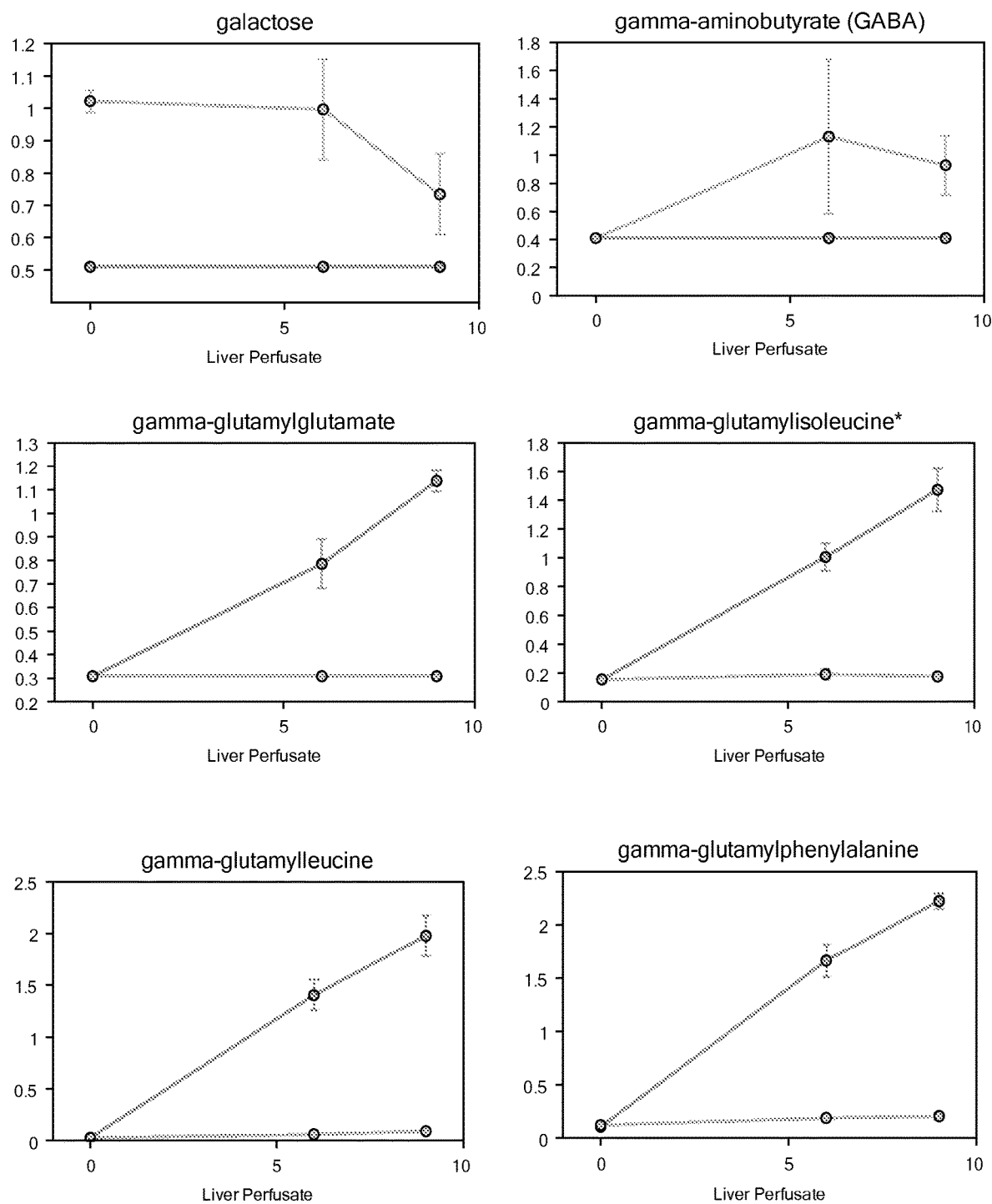
Figure 19J:
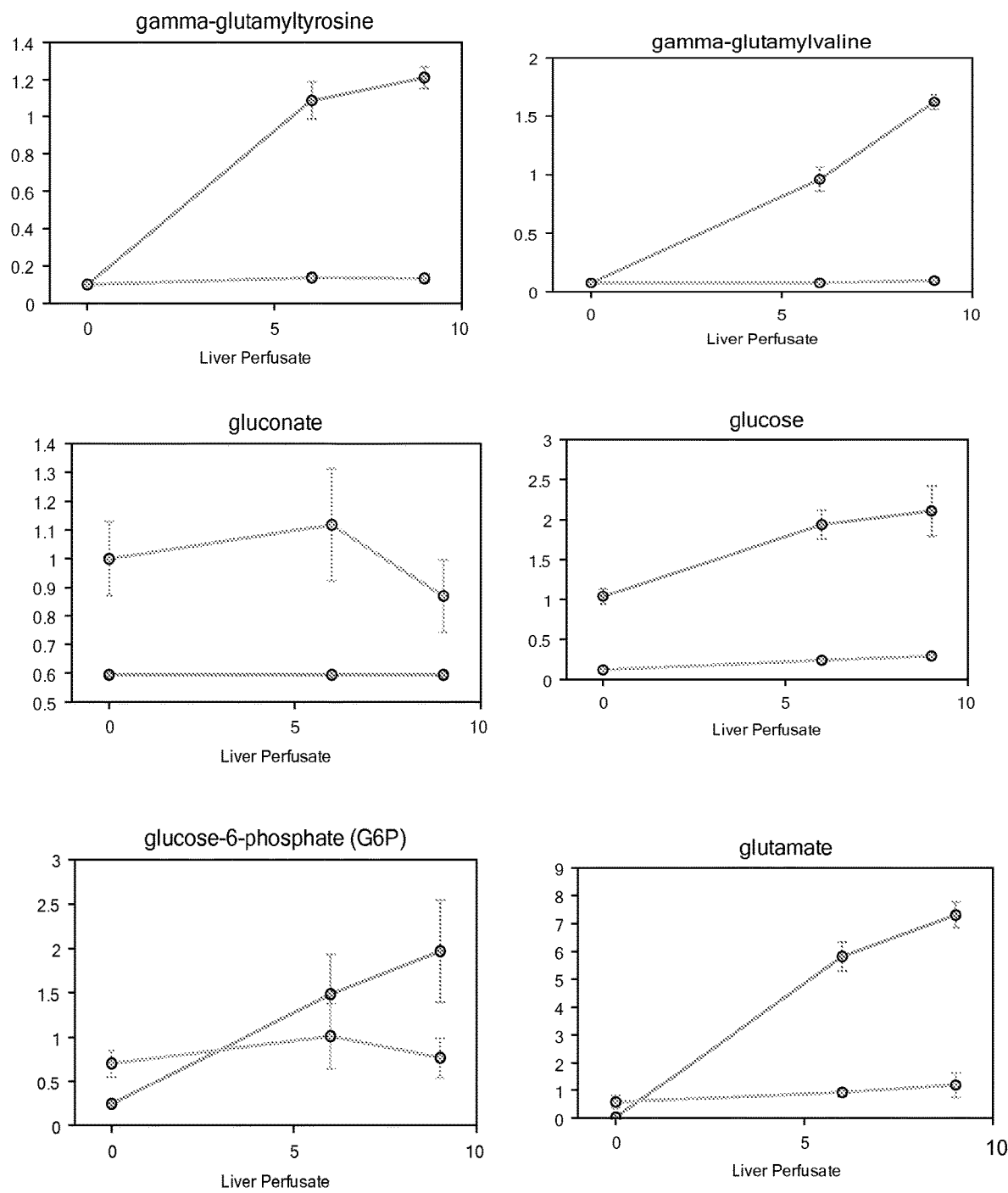
Figure 19K:
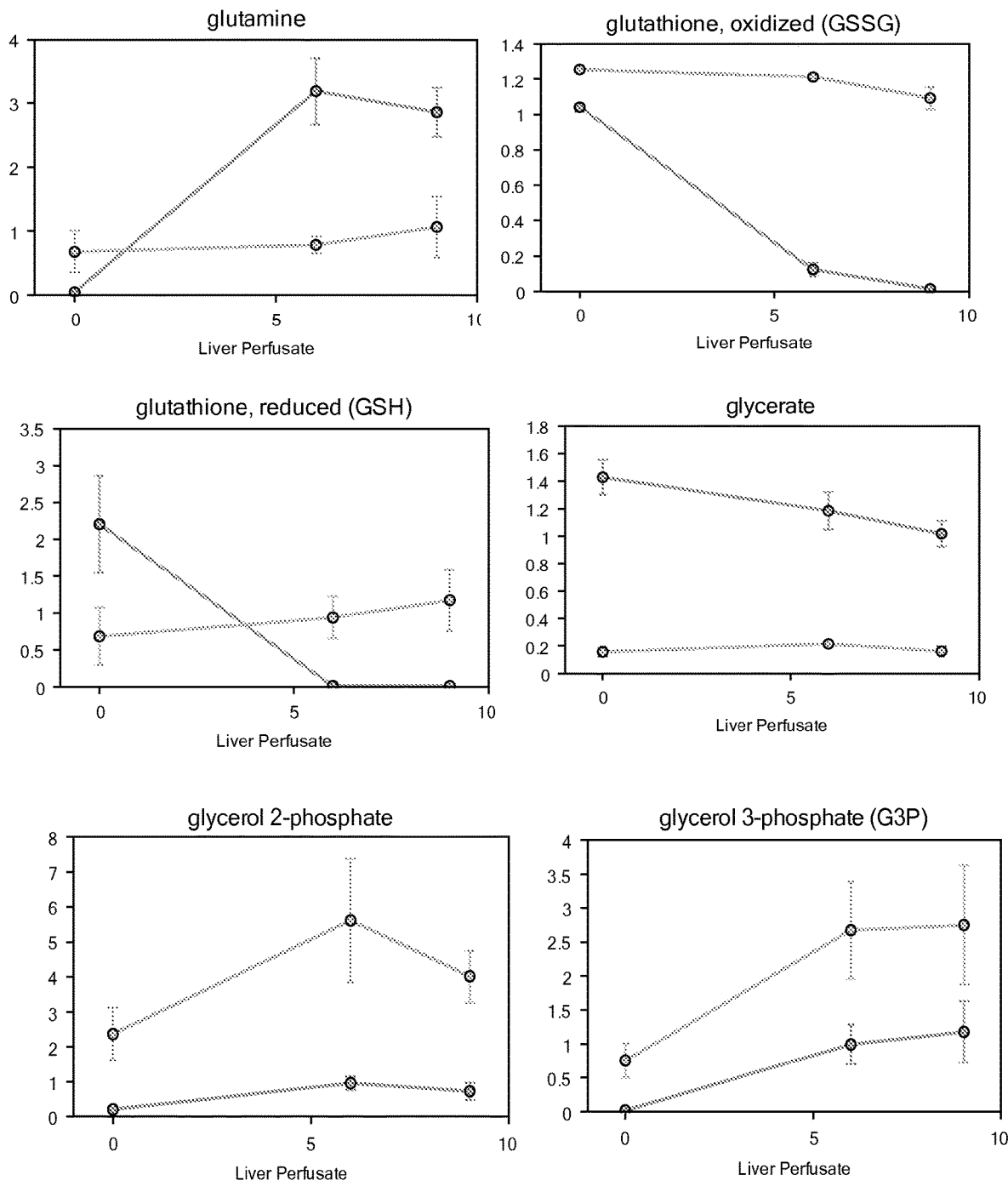
Figure 19L:
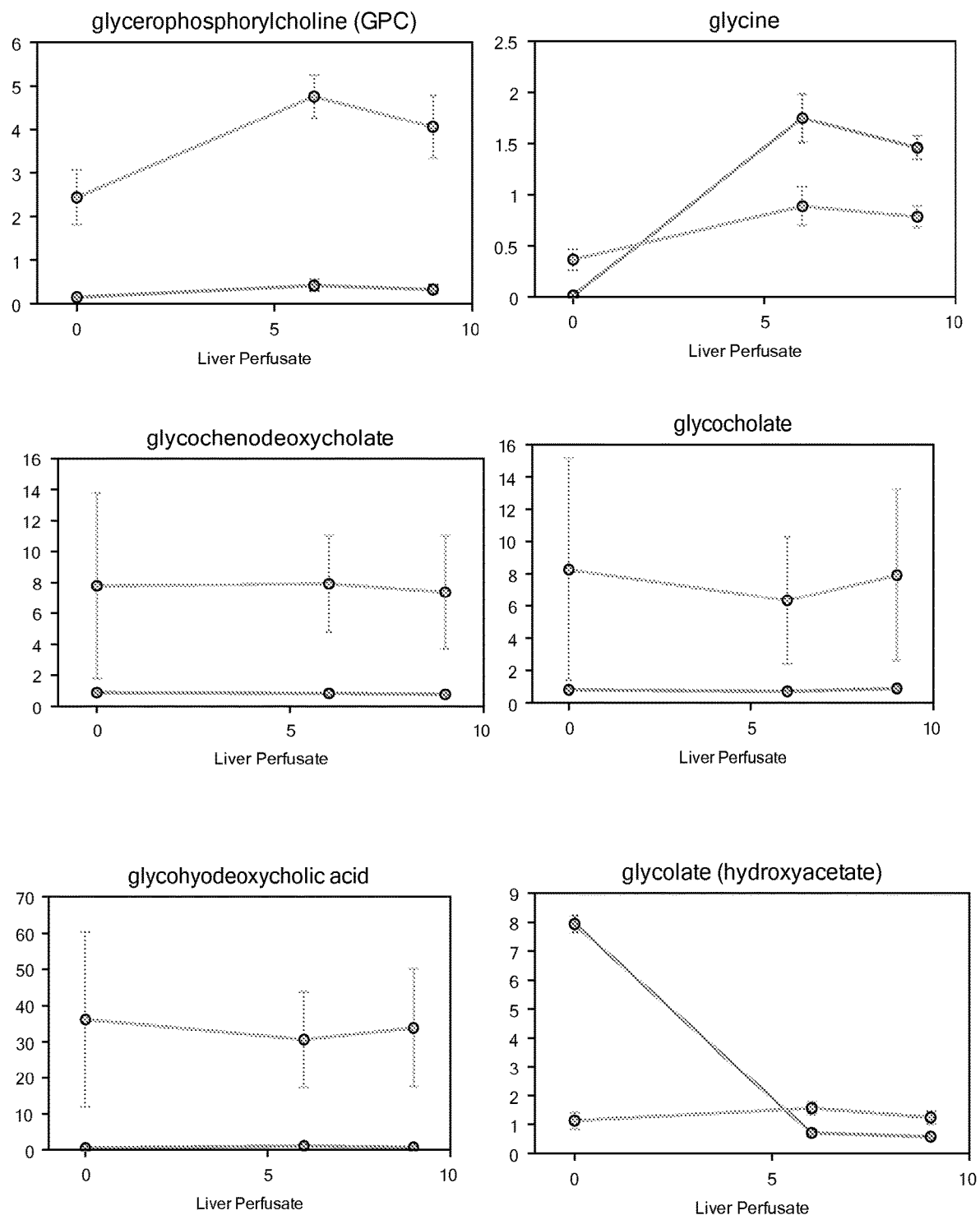
Figure 19N:
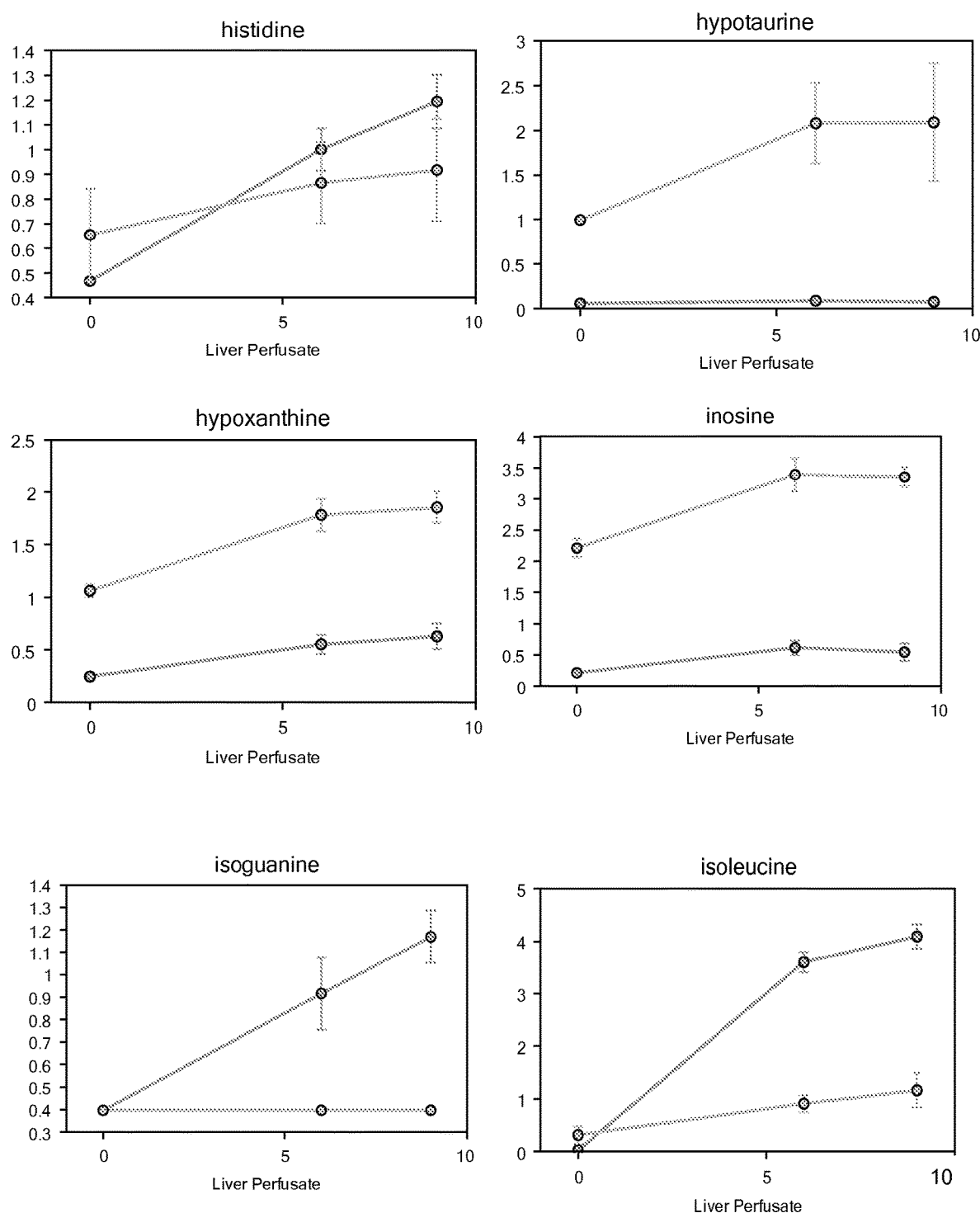
Figure 19O:
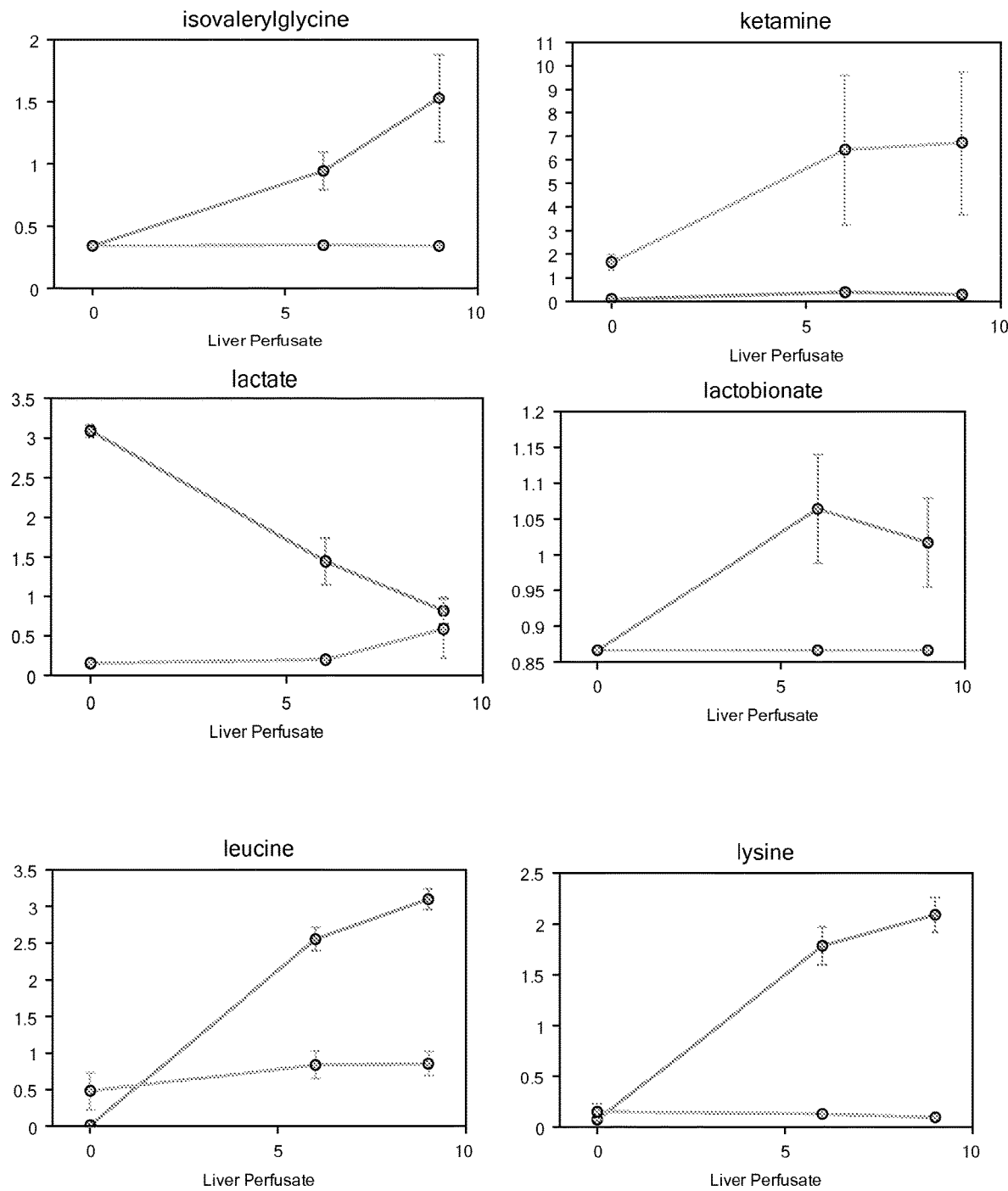
Figure 19P:
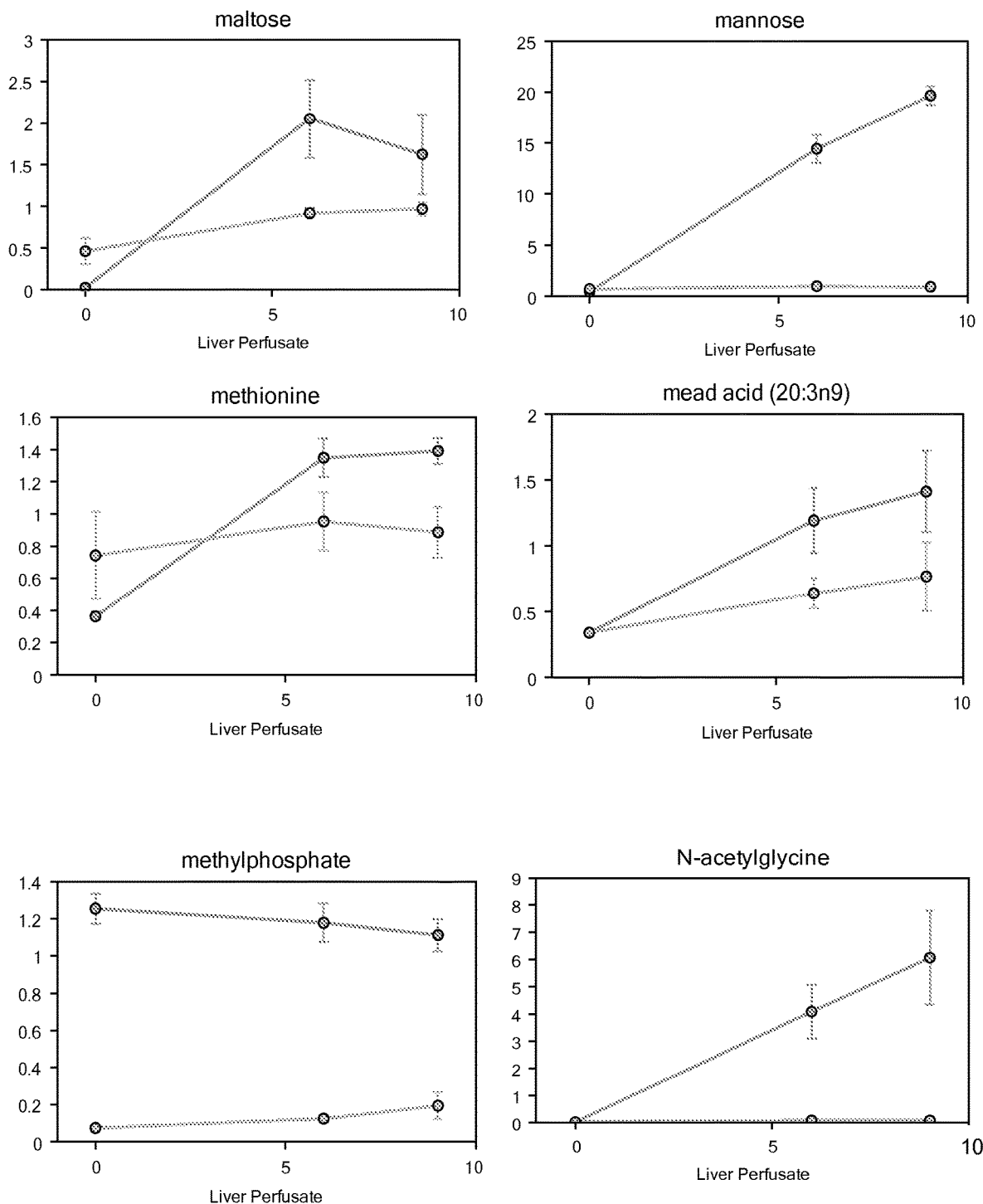
Figure 19R:
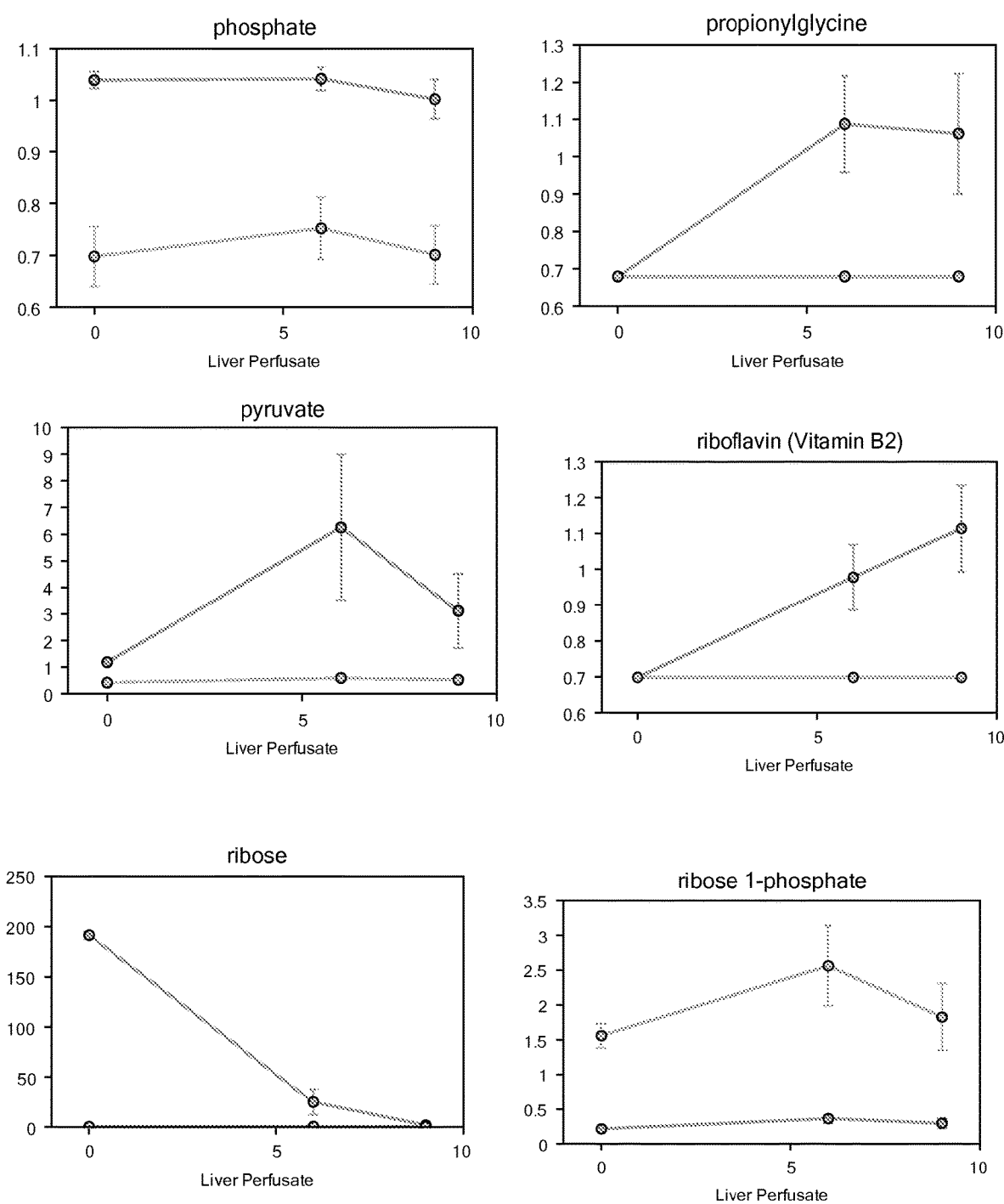
Figure 19S:
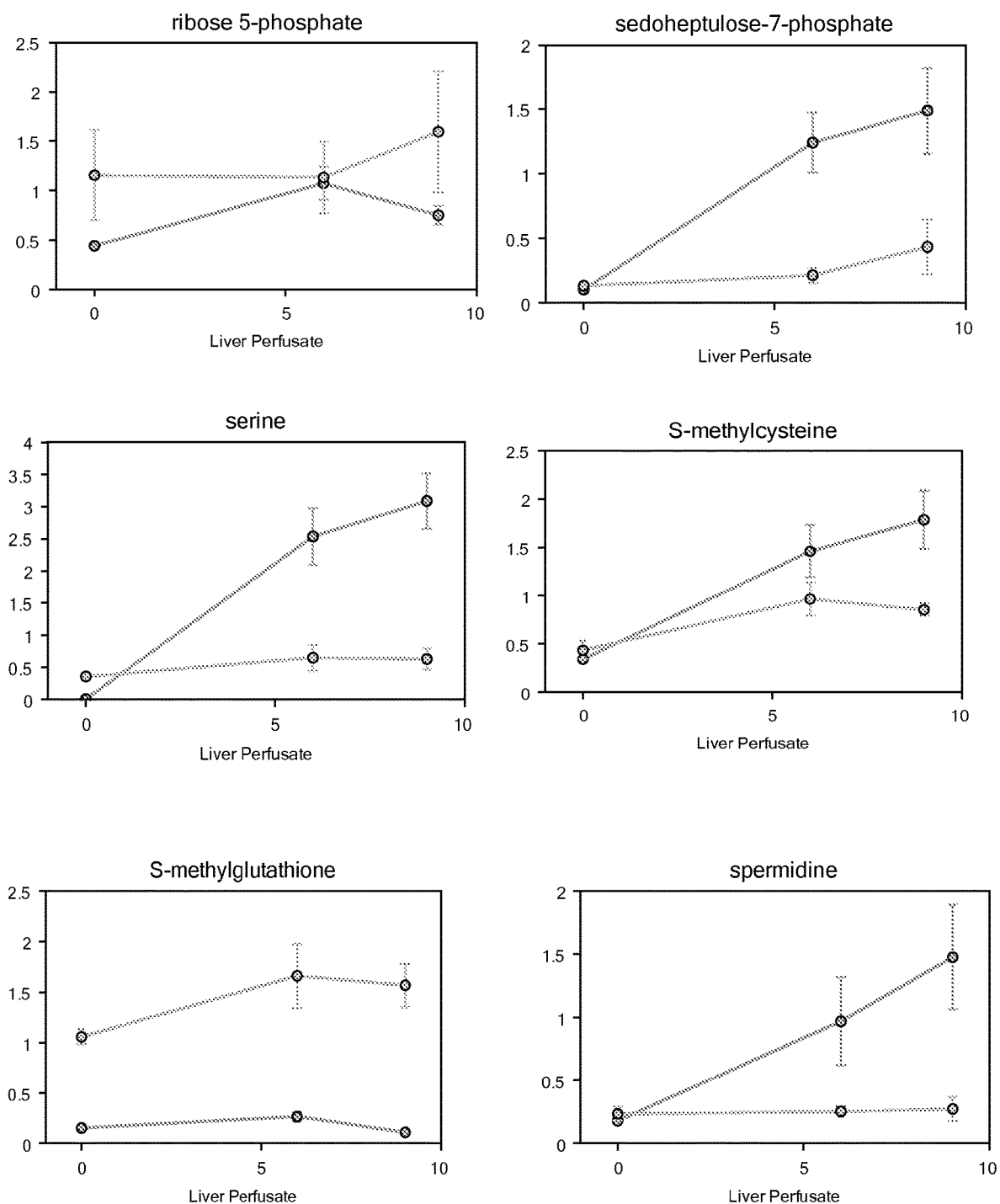
Figure 19T:
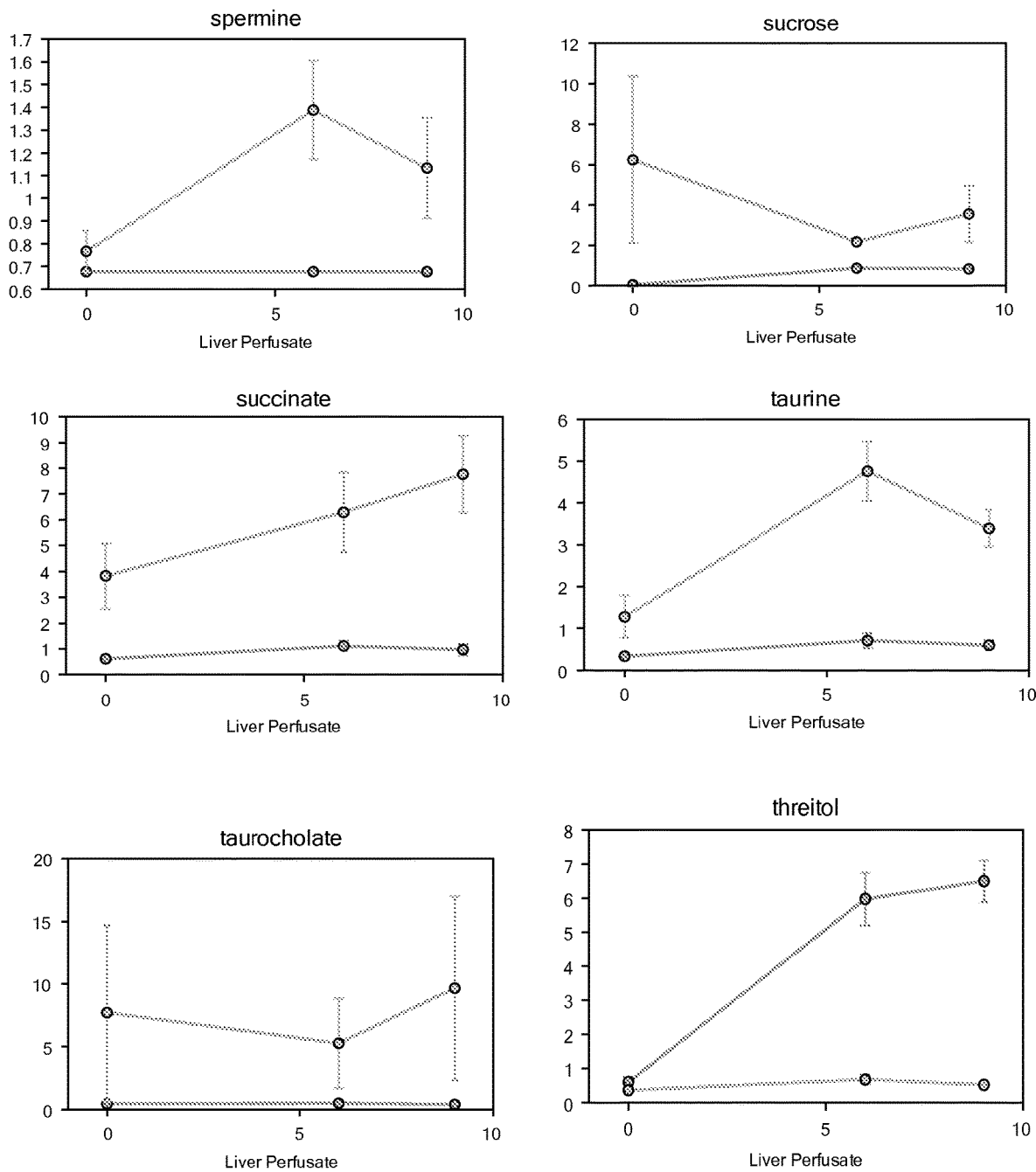
Figure 19U:
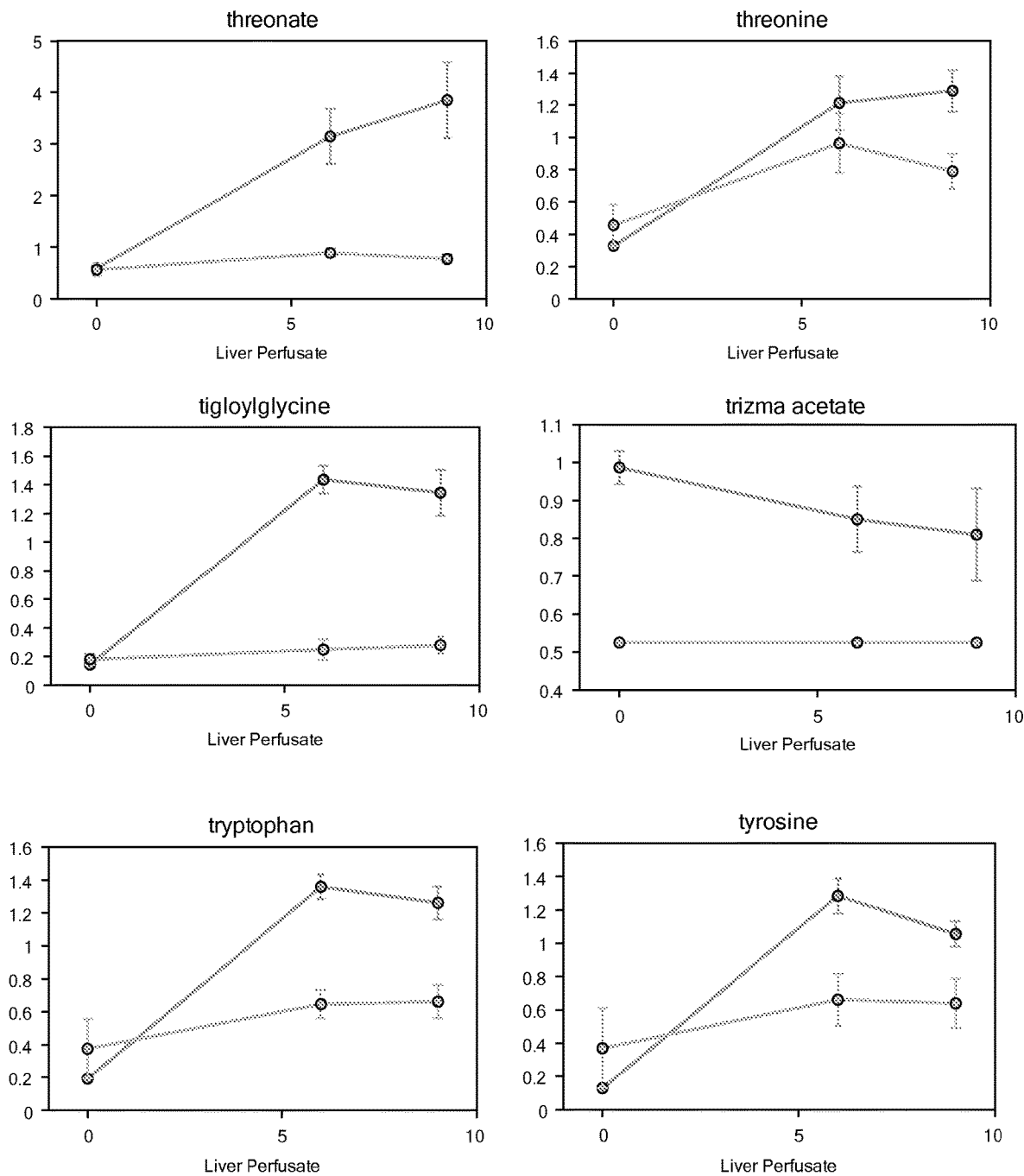
Figure 19V:
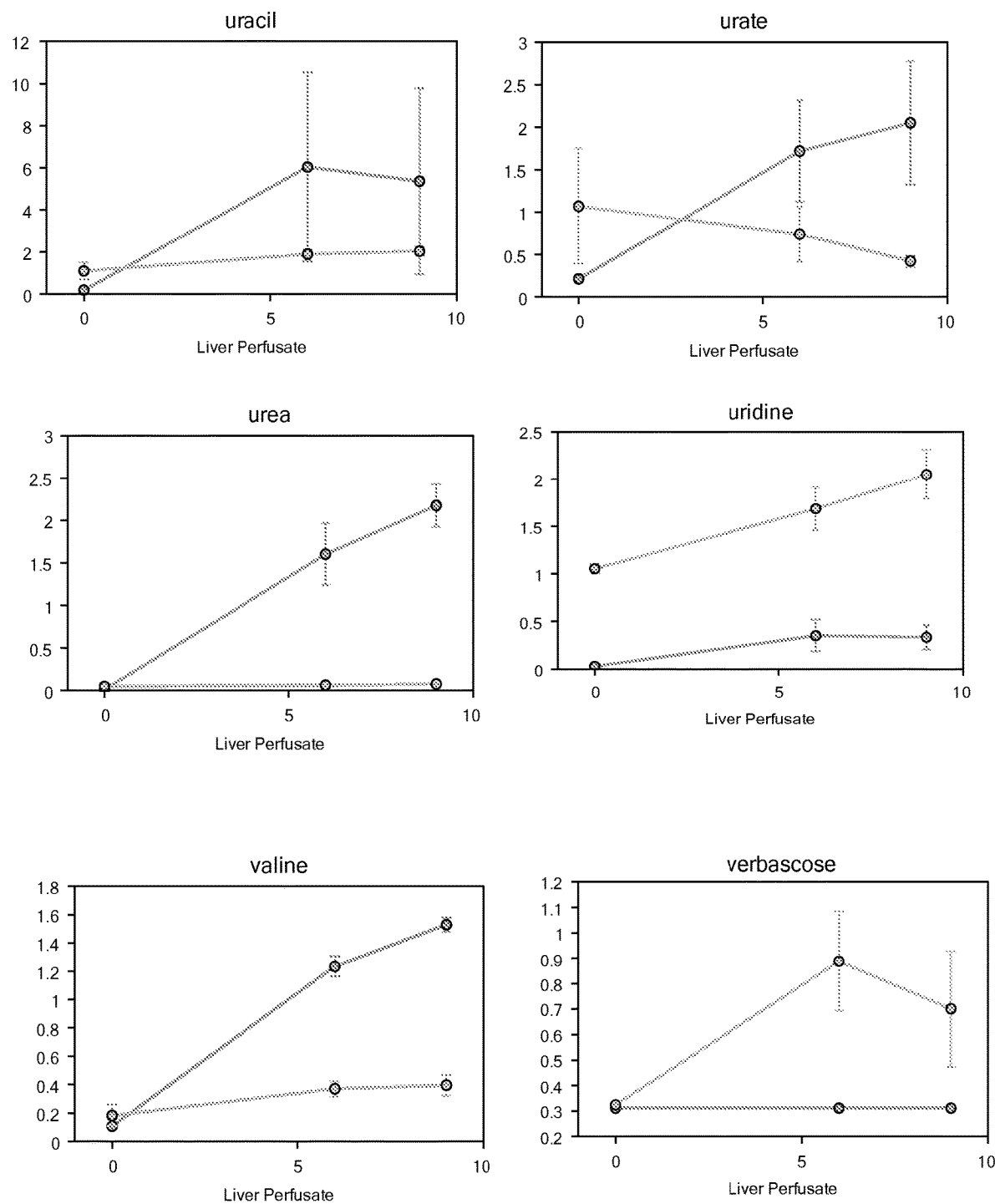

In some embodiments, the methods include determining the level of one or more (such as 2, 3, 4, 5, 5, 10, 15, 20, 25, 30, 40, 50, 60, 70, 80, 90, 100, 120, 130, or more) small molecules or metabolites in a sample, for example one or more of those listed in Tables 8 and 9 and FIGS. 19A-W, or any combination thereof. In particular examples, the methods include determining the level of one or more markers of glycolysis or gluconeogenesis (such as glucose, lactate, pyruvate, fructose 6-phosphate, and/or glucose 6-phosphate), branched chain amino acids (such as valine, lysine, and/or leucine) or metabolites or side-products of branched chain amino acid synthesis (such as alpha-ketoglutarate, glutamine, and/or glutamate), oxidative stress (such as ascorbate), or lipoxygenase activity (such as 12-HETE and/or 15-HETE) from a sample from an organ (such as a liver) or from a subject. In other examples, the methods include determining the level of one or more of ribose, ribulose, glycolate, oxidized homo-glutathione (GSSG), and/or ethanolamine from a sample from an organ (such as a liver) or from a subject. It is then assessed as to whether the level of the one or more biomarker differs from a control sample or a reference value. A change in the amount of one or more biomarkers in the sample, as compared to control or reference value indicates that the organ or subject is at risk for (or has) organ dysfunction. In some examples, a decrease in the levels of biomarkers of glycolysis, branched chain amino acids or branched chain amino acid synthesis, or lipoxygenase activity compared to a healthy control or reference indicates that the organ or subject is at risk for (or has) organ dysfunction (for example, liver dysfunction). In other examples, an increase in the levels of biomarkers of oxidative stress or lipoxygenase activity compared to a healthy control or reference value indicates that the organ or subject is at risk for (or has) organ dysfunction (for example, liver dysfunction).

In particular examples, a decrease in one or more of glucose, lactate, pyruvate, fructose 6-phosphate, glucose 6-phosphate, valine, isoleucine, leucine, alpha-ketoglutarate, glutamate, or 15-HETE as compared to a healthy control or reference value indicates that the organ or subject is at risk for (or has) organ dysfunction. In other particular examples, an increase in ascorbate or 12-HETE as compared to a healthy control or reference value indicates that the organ or subject is at risk for (or has) organ dysfunction. Additional small molecules associated with organ function (particularly liver function) are shown in FIG. 19A-19W. These molecules may be particularly suitable for identifying subjects at risk for (or having) liver dysfunction and/or determining the severity of the liver dysfunction and/or the necessity of imminent organ transplantation.

In other examples, the samples are analyzed for one or more of ribulose, ribose, oxidized homo-glutathione (GSSG), glycolate (hydroxyacetate), xylonate, and/or ethanolamine. For example, a decrease in ribulose, ribose, and/or glycolate and/or an increase in GSSG and/or ethanolamine compared to a control (for example a healthy organ) indicates that an organ has or is predicted to have poor function.

In other embodiments, the methods include determining the level of gene expression of one or more genes in the sample (such as 2, 3, 4, 5, 5, 10, 15, 20, 25, 30, 40, 50, 60, 70, 80, 90, 100, 120, 130, or more), for example, one or more of those genes listed in FIGS. 5-7 and 10, or any combination thereof. In some examples, the methods include determining the level of one or more genes associated with cell proliferation (such as Jun, NFκB, Gadd45β, and/or Gadd45α), general metabolic function and free-radical defenses (such as superoxide dismutase 1 and/or acyl coenzyme A synthetase), and/or differentiation (such as albumin, apolipoproteins, and/or cytochrome P450). These genes may be particularly suitable for identifying subjects at risk for (or having) liver dysfunction and/or determining the severity of the liver dysfunction and/or the necessity of imminent organ transplantation. One of ordinary skill in the art can identify genes associated with cell proliferation and/or differentiation in other tissues or organs.

In particular examples, a decrease in one or more of Jun, NFκB, apolipoprotein A-II, superoxide dismutase 1, acyl coenzyme A synthetase, thrombospondin 1, prothymosin, alpha, cytochrome c oxidase subunit II, and/or alpha-2-macroglobulin as compared to a healthy control or reference value indicates that the organ or subject is at risk for (or has) organ dysfunction. Additional genes associated with organ function (particularly liver function) are shown in FIGS. 5-7 and 10.

In other embodiments, the methods include determining the level of one or more proteins in the sample (such as 2, 3, 4, 5, 5, 10, 15, 20, 25, 30, 40, 50, 60, 70, 80, 90, 100, 120, 130, or more), for example, one or more proteins encoded by the genes shown in FIGS. 5-7 and 10, or any combination thereof. In other examples, the methods include determining the level of cytokines and/or chemokines (for example, one or more of interferon-$\alpha$, interferon-$\gamma$, interleukin-10, interleukin-12/23 (p40), interleukin-1b, interleukin-4, interleukin-6, interleukin-8, and/or tumor necrosis factor-$\alpha$). In particular examples, an increase in one or more of IFN-$\alpha$, TNF-$\alpha$, IFN-$\gamma$, IL-4, IL-1$\beta$, and/or IL-12/IL-23(p40) for example as compared to a healthy control or reference value indicates that the organ or subject is at risk for (or has) organ dysfunction. In other examples, one or more of VEGF, TGF-$\beta$, ERK/MAPK, ErbB, FAK, HGF, p53, insulin receptor, PI3K/AKT, PDGF, FGF, EGF, and NF-$\kappa$B are analyzed. For example, an increase in one or more of VEGF, TGF-$\beta$, ERK/MAPK, ErbB, FAK, HGF, p53, insulin receptor, PI3K/AKT, PDGF, FGF, EGF, and NF-$\kappa$B gene or protein expression (for example compared to a control, such as a dysfunctional organ) indicates good organ function. These proteins may be particularly suitable for identifying subjects at risk for (or having) liver dysfunction and/or determining the severity of liver dysfunction and/or the necessity of imminent organ transplantation.

In still further embodiments, organ function can be measured by production of a fluid, such as bile or urine. In some examples, a decrease in bile production by a liver indicates that the liver is at risk for, or has, dysfunction. In other examples, a decrease in urine production by a kidney indicates that the kidney is at risk for, or has, dysfunction. In further examples, organ function can be measured by the presence or amount of one or more components in a fluid, such as bile or urine. In some examples, production of hydrophilic bile (e.g., decreased levels of taurodeoxycholate) indicates that the liver is predicted to have, or has, good function, while production of hydrophobic bile (e.g., increased levels of glycocholenate sulfate) indicates that the liver is at risk for, or has, dysfunction. In other examples, an increase in hydrophobic bile salts (e.g., glycochenodeoxycholate) indicates that the liver is at risk for, or has, dysfunction, while production of hydrophilic bile salts (e.g., ursodoxycholic acid) indicates that the liver is predicted to have, or has, good function.

In some embodiments, the methods include selecting an organ for transplantation, for example, an organ that is predicted to have good function (or an organ that is not predicted to be at risk for or have dysfunction). In one example, an organ that is a candidate for transplantation is machine perfused and samples are collected. The samples are rapidly analyzed (for example in a few hours) and if the organ is predicted to be at risk for or have organ dysfunction, the organ is not utilized for transplantation. If the organ is predicted to have good function, the organ is utilized for transplantation into a transplant recipient.

In some embodiments, the methods include administering a treatment to a subject identified as being at risk for or having organ dysfunction. One of ordinary skill in the art, such as a clinician, can identify an appropriate treatment for the subject based on the organ, the age, body weight, general health, sex, diet, mode and time of administration, rate of excretion, drug combination, and severity of the condition of the subject undergoing therapy. In one example, liver dysfunction includes enhanced metabolic pathway to gluconeogenesis leading to steatosis, and therapies administered to a subject with liver dysfunction could include intervention in the metabolic pathway (e.g., diet and medication) to reverse the dysfunction. In another example, kidney dysfunction includes decreased glomerular filtration rate due to progressive vasospasm of the afferent arterioles within the nephron and therapies could include identification of vasogenic factors (vasospasm) and amelioration of this condition as precursor of progressive hypertension IV. Methods of Determining Presence or Amount of Biomarkers in a Sample A. Nucleic Acids In some embodiments, the methods disclosed herein include detecting presence and/or amount of one or more nucleic acids (such as DNA, RNA, mRNA, or miRNA) in a sample from a tissue, organ, organ perfusate, fluid, or subject. In some examples, nucleic acids are isolated from the sample. Methods of isolating nucleic acids are known to one of skill in the art. For instance, rapid nucleic acid preparation can be performed using a commercially available kit (such as kits and/or instruments from Qiagen (such as DNEasy®, RNEasy®, or miRNEasy® kits), Life Technologies (such as ChargeSwitch® gDNA, ChargeSwitch® RNA, or mirVana™ kits) Roche Applied Science (such as MagNA Pure kits and instruments), Thermo Scientific (KingFisher mL), bioMérieux (Nuclisens® NASBA Diagnostics), or Epicentre (Masterpure™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162:156-159, 1987). The sample can be used directly or can be processed, such as by adding solvents, preservatives, buffers, or other compounds or substances. In addition, the nucleic acids may be processed further to produce a nucleic acid suitable for various assays, for example, reverse transcribing mRNA to cDNA. One of skill in the art can identify additional reagents and methods that can be used for nucleic acid purification or preparation for use in the methods disclosed herein.

Methods for analyzing nucleic acids in a sample (for example, detecting amount and/or changes in gene expression) are known to one of skill in the art and include, but are not limited to, Southern blotting, Northern blotting, in situ hybridization, RNase protection, subtractive hybridization, differential display, antibody-based methods (such as use of antibodies that can recognize specific duplexes, including DNA duplexes, RNA duplexes, and DNA-RNA hybrid duplexes or DNA-protein duplexes), microarray-based methods, amplification-based methods, and sequencing-based methods. One of skill in the art can identify additional techniques that can be used to analyze gene expression, and it is to be understood that gene expression detection methods for use in the present disclosure include those developed in the future.

In some examples, gene expression (such as presence and/or amount of RNA, mRNA, and/or miRNA) is identified or confirmed using microarray techniques. Thus, expression of one or more genes (or an expression profile) can be measured using microarray technology. In this method, nucleic acids of interest (including for example, cDNAs and/or oligonucleotides) are plated, or arrayed, on a microchip substrate. The arrayed nucleic acids are then hybridized with isolated nucleic acids (such as cDNA or mRNA) prepared or isolated from the sample. Hybridization of the isolated nucleic acids with the arrayed nucleic acids is detected, for example, based on identification of a label associated with a nucleic acid that is detected at an addressable location non the array. Microarray analysis can be performed by commercially available equipment, following the manufacturer's protocols, such as are supplied with Affymetrix GeneChip® technology (Affymetrix, Santa Clara, Calif.), or Agilent's microarray technology (Agilent Technologies, Santa Clara, Calif.).

In further examples, nucleic acids are analyzed by amplification techniques including, polymerase chain reaction (PCR), quantitative real-time PCR, reverse transcription PCR (RT-PCR), quantitative RT-PCR (qRT-PCR), digital PCR, strand displacement amplification (see U.S. Pat. No. 5,744,311); transcription-free isothermal amplification (see U.S. Pat. No. 6,033,881); transcription-mediated amplification (TMA); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

In other examples, gene expression is detected using sequencing techniques. Representative methods for sequencing-based gene expression analysis include Serial Analysis of Gene Expression (SAGE; Velculescu et al., *Science* 270:484-487, 1995), 454 pyrosequencing (Tones et al., *Genome Res.* 18:172-177, 2008), RNA-seq (Wang et al., *Nat Rev. Genet.* 10:57-63. 2009), and gene expression analysis by massively parallel signature sequencing (MPSS; Brenner et al., Nat. Biotechnol. 18:630-634, 2000).

B. Proteins

In some embodiments, the methods disclosed herein include detecting presence and/or amount of one or more proteins or fragments thereof in a sample from a tissue, organ, organ perfusate, fluid, or subject. In some examples, the samples are used without processing. In other examples, the samples are processed prior to protein analysis, for example by adding one or more components (such as detergents, buffers, or salts), lysis (if cells are present), and/or fractionation.

Any standard immunoassay format (such as ELISA, Western blot, or radioimmunoassay) can be used to measure protein levels. Immunohistochemical techniques can also be utilized for protein detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

In some examples, protein (or fragments thereof) are detected in a sample using mass spectrometry methods, such as mass spectrometry (MS), tandem MS (MS/MS), matrix-assisted laser desorption/ionization-time of flight (MALDI-TOF) MS, or electrospray ionization (ESI)-MS. In some examples, the sample may be subjected to a separation technique, such as liquid chromatography or 2-dimensional electrophoresis prior to MS analysis. Semi-quantitative or quantitative MS methods are also available. (See, e.g., Gygi et al., *Nat. Biotechnol.* 17:994-999, 1999; Aebersold, *J. Inf. Dis.* 187:S315-S320, 2003.)

In other examples, proteins or fragments thereof are identified or confirmed using microarray techniques. In this method, protein of interest or fragments thereof are plated, or arrayed, on a microchip substrate. The arrayed proteins are then contacted with proteins prepared or isolated from the sample. Binding of the proteins from the sample with the arrayed proteins is detected, for example, based on contacting with a label and localization to an addressable location on the array. Microarray analysis can be performed by commercially available equipment, following the manufacturer's protocols, such as are supplied with ProtoArray® protein microarray (Life Technologies) or HuProt™ arrays (Cambridge Protein Arrays).

In other examples, a bead-based assay is used to measure proteins in the sample. Such assays typically include beads coated with a capture antibody for a specific analyte. The beads are incubated with proteins prepared or isolated from a sample and binding of a protein to a bead is detected, for example using flow cytometry. Bead-based assays can be multiplexed, for example by including beads with different fluorescence intensities, each coated with an antibody specific for a specific protein. The presence and identity of different proteins can thus be detected, based on the fluorescence of the particular bead bound by a protein. Bead-based assays are commercially available (such as the Luminex xMAP® technology or the BD Biosciences Cytometric Bead Array).

One of skill in the art can identify additional techniques that can be used to analyze proteins in a sample, and it is to be understood that protein detection methods for use in the present disclosure include those developed in the future.

C. Small Molecules/Metabolites

The small molecule profile of a sample can be obtained through, for example, a single technique or a combination of techniques for separating and/or identifying small molecules known in the art. Examples of separation and analytical techniques which can be used to separate and identify the compounds of the small molecule profiles include: HPLC, TLC, electrochemical analysis, mass spectroscopy (for example, GC/MS or LC/MS/MS), refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art. One of skill in the art can identify additional techniques that can be used to analyze small molecules, and it is to be understood that detection methods for use in the present disclosure include those developed in the future.

The methods can be used to detect electrically neutral as well as electrochemically active compounds. Detection and analytical techniques can be arranged in parallel to optimize the number of molecules identified. In some examples, analysis of the small molecule profile of a sample includes analysis by a commercial provider, such as Metabolon (Durham, N.C.). In particular non-limiting examples, the small molecule profile is analyzed in perfusate from an ex vivo perfused organ, bile, or urine.

The present disclosure is illustrated by the following non-limiting Examples.

Example 1

Experimental Model

This example describes the liver transplantation model used for sample collection for further analysis. The machine perfusion system and oxygen carrier perfusion solution are described in related U.S. Provisional Patent Application No. 61/713,284, filed Oct. 12, 2012, and International Pat. Publ. No. WO 2014/059316, both of which are incorporated herein by reference in their entirety.

Two groups of 6 swine underwent orthotopic liver transplantation after a period of 9 hours of preservation (cold ischemia time (CIT)=9 hours). Both groups had a 5 day follow up while receiving Tacrolimus (0.3 mg/kg) as their primary immunosuppressive therapy. All surviving animals underwent an end-study necropsy on the 5$^{th}$ post-operative day. This challenging swine model (CIT=9 hours) has been consistently demonstrated as having a 70-100% mortality in 5-7 days.

The control group had their liver allografts preserved with CSP (University of Wisconsin solution (UW) at 4° C. under anoxic conditions). The study group had their liver allografts preserved with machine perfusion (MP; Organ Assist, Groningen, Netherlands) and a newly developed hemoglobin-based oxygen carrier (HBOC) solution (HEMOPURE (OPK Biotech, Cambridge, Mass.) mixed with Belzer Machine Perfusion Solution (BMPS) at 1:3). The MP livers underwent continuous perfusion under dual pressure (continuous at the portal vein and pulsatile at the hepatic artery) at 21° C. (subnormothermic conditions) and with a $FiO_2$ of 60%. Both groups had their liver allografts biopsied at 3, 6 and 9 hours while under preservation. Additional biopsies were taken after organ reperfusion and 5 days after the initial procedure (end-study necropsy). The schedule for sample collection is shown in Table 1. All laboratory and clinical parameters were assessed. Repeated measurements were compared between study and control groups using a mixed model with fixed effect (animal group) analysis. Continuous data were compared using either t testing or the nonparametric Wilcoxon two-sample test when appropriate.

TABLE 1

Sample collection schedule

| | | Time frame | | | | |
|---|---|---|---|---|---|---|
| Group | Specimen | 0 | 3 | 6 | 9 | Post-reperfusion | Final |
| Control (CSP) | Liver biopsy | X | X | X | X | X | necropsy |
| | Perfusate | X | X | X | X | X | X |
| | Bile † | No | No | No | No | X | X |
| Study (MP) | Liver biopsy | X | X | X | X | X | necropsy |
| | Perfusate | X | X | X | X | X | X |
| | Bile | X | X | X | X | X | X |

† liver allografts do not make bile during CSP

The study group (MP) had 100% survival and the control group (CSP) had a 33% survival in the 5 day period (p<0.05). The MP group had none to mild signs of reperfusion syndrome (RS) after liver allograft implantation and the CSP group had moderate to severe signs of RS. The CSP group received a significantly higher (150%, p<0.05) amount on intravenous fluids and a higher amount of vasopressors after liver allograft reperfusion while experiencing major vasodilatation as a result of the moderate to severe RS.

The CSP had a higher index of ischemia/reperfusion (IR) tissue injuries revealed by serial histological analysis during liver allograft preservation. IR injuries were considered none to mild in the MP group and moderate to severe in the CSP group (blind analysis by a selected group of transplant pathologists). All the animals that expired in the CSP experienced progressive liver allograft dysfunction leading to irreversible liver failure. The surviving CSP animals were clinically ill (renal failure, coagulopathy, progressive lactic acidosis and decreased mental status) and more ill than the MP group, who had uneventful post-operative courses.

All liver allografts were able to make bile, produce glucose and clear lactate under an extended period of time (CIT=9 hours) while under MP. Gasometric analysis of the perfusate showed high ($pO_2$>400 mm Hg) levels of oxygenation on both arterial and venous ports, low levels of $CO_2$ ($pCO_2$<18 mm Hg) and sustained pH throughout the entire perfusion protocol. Serial liver biopsies (3, 6, 9 hours) showed normal cytoarchitecture features of the hepatic parenchyma during the ex vivo MP stage. Over 16 physiological parameters were compared over the five day post-operative period and all 16 showed one-directional effect (statistically significant or not) superior to the study group compared to control. Exemplary results are shown in FIGS. 2A-2G. MP had a statistically significant (p<0.05) beneficial effect in liver allograft preservation when compared to CSP. In assumption that the MP/HBOC does not affect animal physiology post-operatively, the probability of such results is 0.5 in power 16 or p<0.004.

Tissue samples were prospectively collected for histological analysis and scoring of ischemia/reperfusion (IR) injury as shown in Table 2.

TABLE 2

Tissue sample collection for IR analysis

| Times | Samples | Notes |
|---|---|---|
| T0 | donor baseline | Obtained prior to organ procurement |
| T1 | back table (after flush) | Obtained immediately after organ recovery |
| T2 | 3 h of preservation | Obtained in both groups (CSP and MP) |
| T3 | 6 h of preservation | Obtained in both groups (CSP and MP) |
| T4 | 9 h of preservation | Obtained in both groups (CSP and MP) |
| TRP | post reperfusion | Obtained after liver implantation |
| Necropsy | 5$^{th}$ post-operative day | Obtained at the end-study necropsy |

All tissue samples were processed immediately after collection. The samples were initially divided in 2 pieces, for fresh frozen sections initially and for subsequent sections in paraffin afterwards. All tissues were processed and stained (H&E and immunohistochemistry) at the Division of Transplant Pathology, Department of Pathology, UPMC. Tissue samples for the assessment of hepatocellular injury were collected before, during, and after preservation, post-reperfusion and at end study necropsy. All liver samples were fixed in 10% buffered formalin, embedded in paraffin, sectioned (5 μm) and stained with hematoxylin and eosin for histological analyses. The severity of liver IR injuries was blindly graded by transplant pathologists using initially the International Banff Criteria (*Hepatology* 3:658-663, 1997). A modified Suzuki's criteria (Suzuki et al., *Transplantation* 55:1265-1272, 1993) was subsequently applied to quantify the IR injuries and correlate the clinical with the histopathological findings. Complete histological features were assessed both in the portal tracts and the hepatic lobules. The scored number was further weighted (none=0, mild 1-25%=1; moderate 25-50%=2 and significant >50%=3); re-scored based on its contribution to the injury while grouped into four categories and subsequently expressed as mean±standard deviation. The IR scores between the two groups were compared chronologically during liver preservation and after transplantation.

Figure 3:
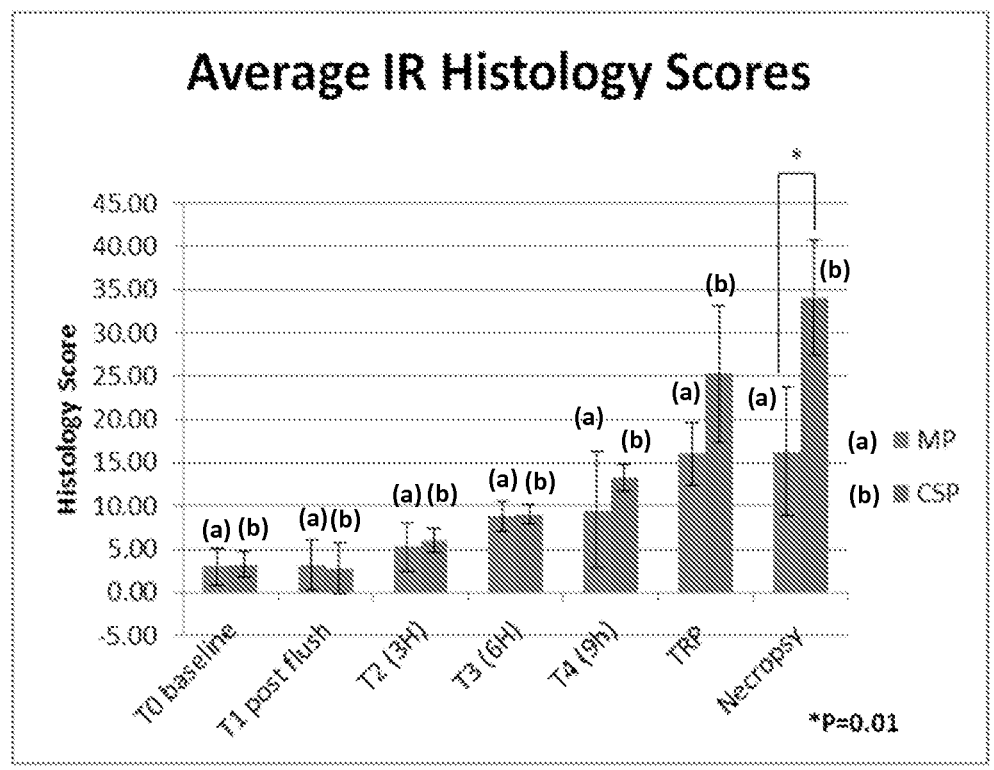
FIG. 3 is a graph showing histological analysis of ischemia-reperfusion (IR). IR scores (Suzuki modified) were determined by serial analysis of inflammatory changes within the portal tracts and the hepatic lobules. The graphic shows a longitudinal comparison of average IR scores for cold static preservation (CSP—(b)) and machine perfusion (MP—(a)). The IR scores at necropsy were significantly lower in the MP group (p=0.01), showing the benefits of effective ex-vivo oxygenation on liver tissue viability after transplantation.

The entire histological analysis was combined within a single graphic displaying all the scores for all the samples (FIG. 3). An IR score was calculated for each time point (mean±SD) and compared longitudinally with all values obtained from the different time points. The control group (CSP) histological analysis (H&E) revealed the presence of moderate to severe IR injuries throughout the entire experiment. There was no improvement of the IR injuries after liver implantation and 67% of the animals expired within hours and/or days from liver allograft failure due to the severity of the IR injuries. The surviving animals (33%) revealed significant (p=0.01) allograft damage at the time of the elective end-study necropsy.

The study group (MP) presented none to mild IR injuries during preservation and after liver allograft implantation (TRP—reperfusion samples). The IR scores showed a progressive resolution of this transient inflammatory process over the next 5 days and the animals had 100% survival with good liver allograft function. There was a significant (p<0.05) difference between the two groups when comparing the tissue samples analyzed after the end-study necropsy. The magnitude of the IR injuries seen at the control group (CSP) were significantly higher and led to irreversible liver allograft failure and death (only 33% survival, p<0.05).

Mitochondrial Isolation and Respiration:

Fresh tissue samples (liver biopsies from the allografts) were obtained from both groups and sent to a mitochondrial functional analysis in an oxygraph chamber. Liver mitochondria were isolated by differential centrifugation in a buffer (250 mM sucrose, 10 mM Tris, 1 mM EGTA, pH 7.4) at 4° C., as previously described. To measure respiration of isolated mitochondria, 1 mg/ml of protein was suspended in respiration buffer (120 mM KCl, 25 mM sucrose, 10 mM HEPES, 1 mM EGTA, 1 mM $KH_2PO_4$, 5 mM $MgCl_2$) in a stirred, sealed chamber fit with a Clark-type oxygen electrode (Instech Laboratories) connected to a data recording device (DATAQ Systems).

Figure 4A:
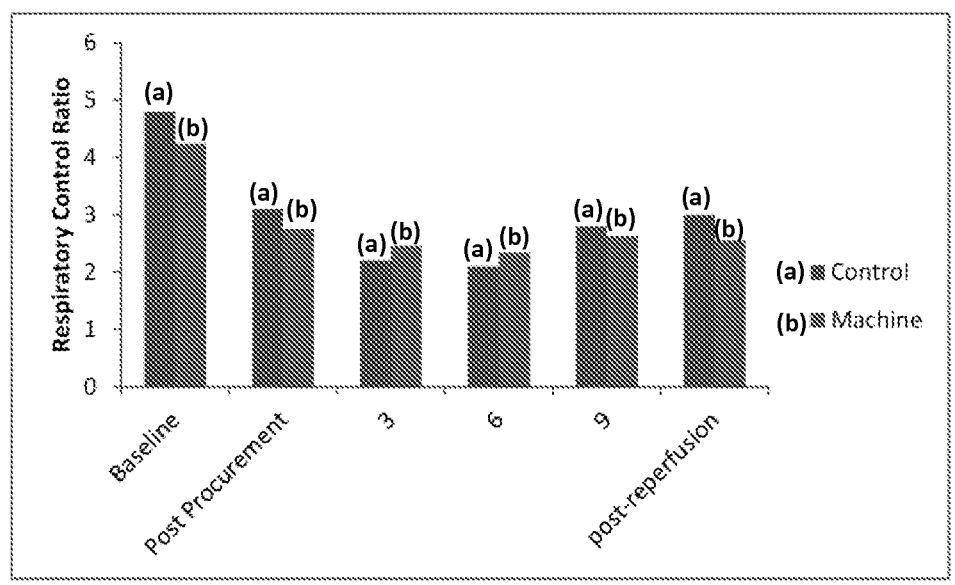
FIGS. 4A-4C are a series of graphs showing mitochondrial function in control and study groups.
Figure 4B:
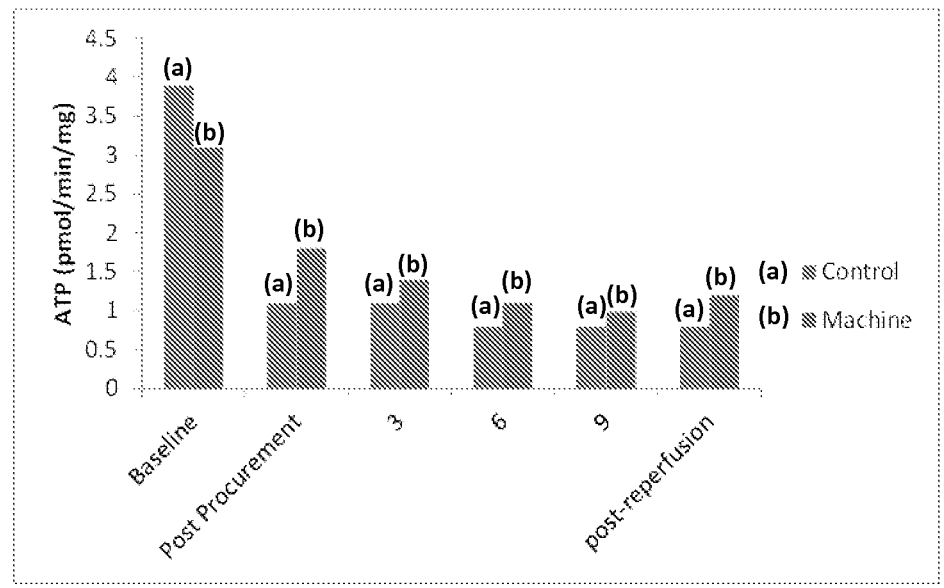
Figure 4C:
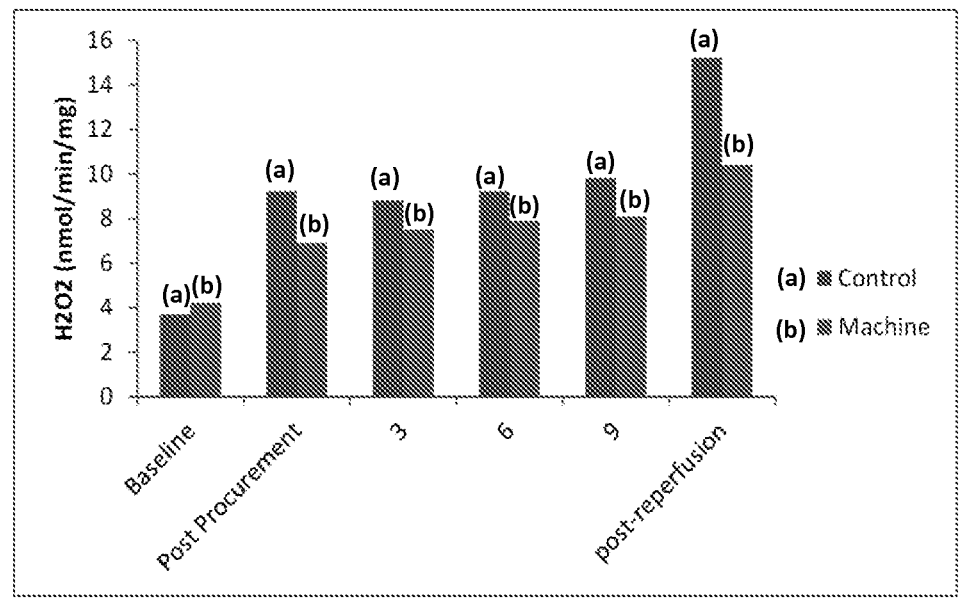

Mitochondrial function was sustained throughout the entire MP protocol with pulsatile pressures (MAP=20 mmHg) at 21° C. The oxygen delivery was estimated to be around 0.013 $mlO_2$/g/min and the oxygen consumption was estimated around 0.0016 $mlO_2$/g/min. Both the respiratory control ratio (RCR) (FIG. 4A) and ATP assays (FIG. 4B) showed uninterrupted and efficient mitochondrial function within the hepatic parenchyma while under machine perfusion at 21° C. The ROS production after liver allograft reperfusion was 2 fold higher in the CSP group (FIG. 4C).

Example 2

Microarray Analysis

This example describes microarray analysis of hepatic gene expression in the control and study transplantation groups.

Methods

Microarray Analysis:

Microarray analysis was performed using Affymetrix GeneChip® Porcine Genome Array (Affymetrix, Santa Clara, Calif., USA). Liver tissue samples from both groups (control=CSP and study=MP) were obtained before and after liver preservation and at the time of the end-study necropsy. Total RNA (10 μg) or mRNA (0.2 μg) was first reverse transcribed in the first-strand cDNA synthesis reaction. Following RNase H-mediated second-strand cDNA synthesis, the double-stranded cDNA was purified and served as a template in the subsequent in vitro transcription (IVT) reaction. The IVT reaction was carried out in the presence of T7 RNA Polymerase and a biotinylated nucleotide analog/ribonucleotide mix for complementary RNA (cRNA) amplification and biotin labeling. The biotinylated cRNA targets were fragmented in 1× fragmentation buffer solution provided with the GeneChip sample cleanup module (Affymetrix) at 94° C. for 35 min. A total of 10 μg of fragmented biotin-labeled cRNA per replicate in hybridization mixture then was hybridized to Porcine Genome Array from Affymetrix GeneChips™ and incubated overnight at 45° C. in Affymetrix GeneChip Hybridization Oven 640, all according to the manufacturer's instructions.

The mixture was removed 16 hours after hybridization in several cycles; the chips were washed with non-stringent buffer and stained with streptavidin-phycoerythrin antibody solution (Affymetrix) on an automated Affymetrix GeneChip Fluidic Station 450 station. The data were collected using an Affymetrix GeneChip scanner 3000. Microarray images quantified using Affymetrix GeneChip Operating Software.

Microarray Data Analysis:

Normalization and pre-processing of data were performed using dChip software. Expression intensities were log transformed, and genes with less than 80% present calls, expression level lower than 7, or SD smaller than 0.5 were filtered out. Individual expression points of the top 100 genes that were found to be differentially regulated were fitted by statistics and the clustering pattern plotted in Microsoft Excel. The threshold line corresponds to a p value of 0.05 as calculated by the Fischer's test.

The CEL data generated by the microarray were converted using GCOS 1.4 software (Affymetrix). The data generated by the Affymetrix platform contain all information required by MIAME protocols to allow the data to be submitted as needed. Details of compliance met by the CGOS 1.4 software and all other programs used to convert CEL files to Excel microarray data are provided at ncbi.nlm.nih.gov/geo/info/MIAME.html.

Gene Ontology Analysis:

The web tools DAVID (Bioinformatics enrichment tools: paths toward the comprehensive functional analysis of large gene lists) were used to identify enriched functionally related gene groups following machine perfusion.

Pathway Analysis:

Genes whose expression value was >2 or ≤2-fold compared to the control group were analyzed for identification of key canonical pathways associated with liver growth and pathology using Ingenuity Software®. The pathways that were found to be most significantly up-regulated were plotted. The biological processes that were found to be significantly affected were displayed along the y-axis. The x-axis displays the –log of p-value and was calculated by Fisher's exact test right-tailed.

Results

Hepatic gene expression was analyzed before and after preservation and at necropsy. There was a striking increase in proliferation-associated genes (Jun, Fos, ATP synthase F0 subunit 8, Apolipoprotein A-II, Metallothionein isoform, Acyl coenzyme A synthetase, Syndecan 2, Collagen Alpha 2, Prothymosin alpha) in the MP group. Many hepatocyte-differentiation genes were also upregulated, including albumin, apolipoproteins, and several cytochrome P450 (CYP) members.

Figure 5:
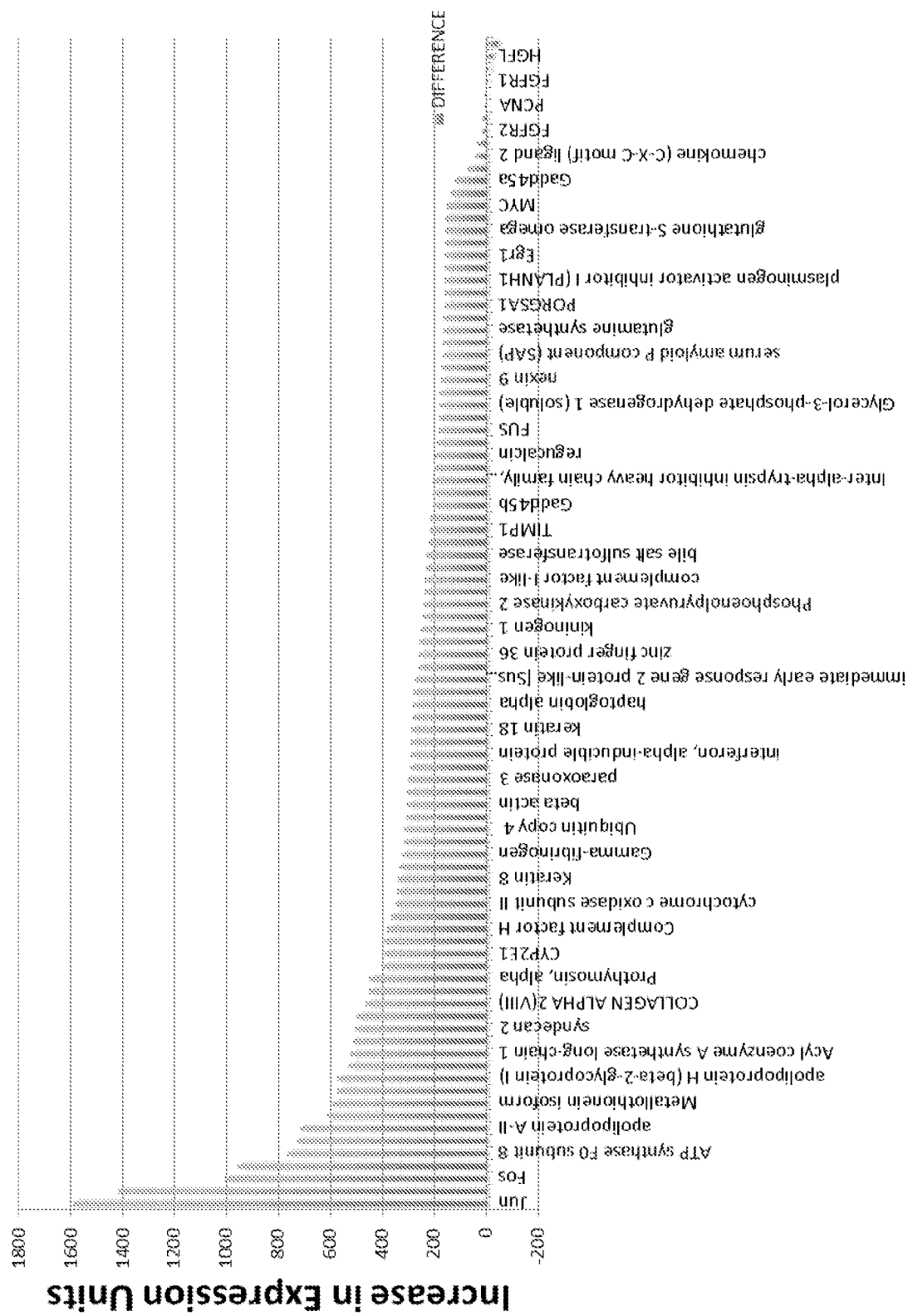
FIG. 5 is a graphic representation of the transcriptomic analysis (microarray) of 20,000 genes obtained from pig liver samples after machine perfusion showing the top 100 genes with increased expression after 8 hours sustained ex vivo oxygenation before liver allograft implantation.
Figure 6:
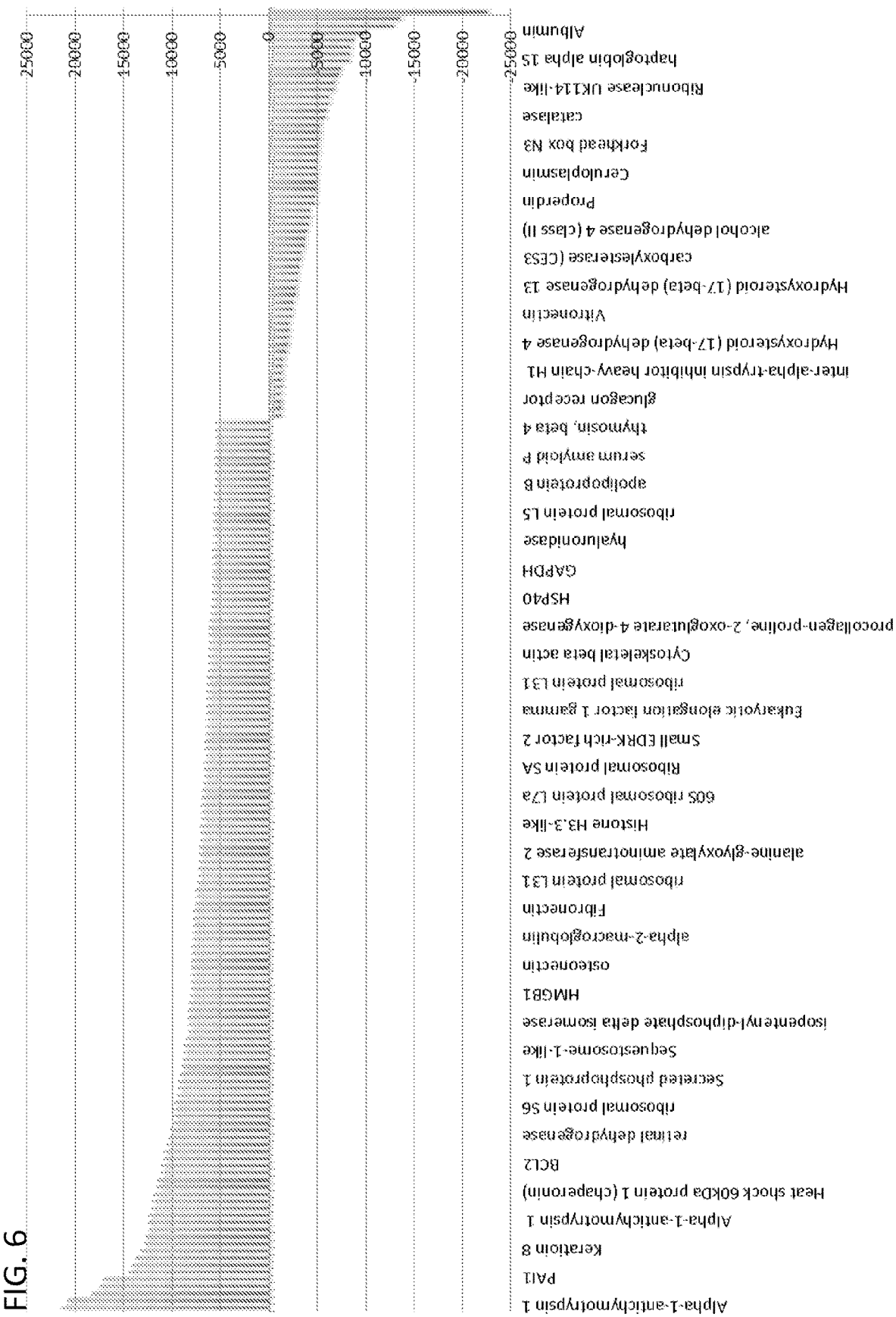
FIG. 6 is a graphic representation of the transcriptomic analysis (microarray) of 20,000 genes obtained from pig liver samples showing the genes with the greatest differences in gene expression immediately following liver allograft reperfusion compared to the fifth post-operative day (end-study necropsy).

The top 100 most affected genes in the MP group showed over-expression associated with general metabolic, anti-inflammatory, and regenerative functions, as well as protective mechanisms against free radicals (FIG. 5). MP also resulted in increased expression of several genes associated with entry of hepatocytes into the G1 cell cycle phase (FIG. 6). Genes associated with hepatocyte differentiation were also upregulated (FIG. 7).

Figure 9B:
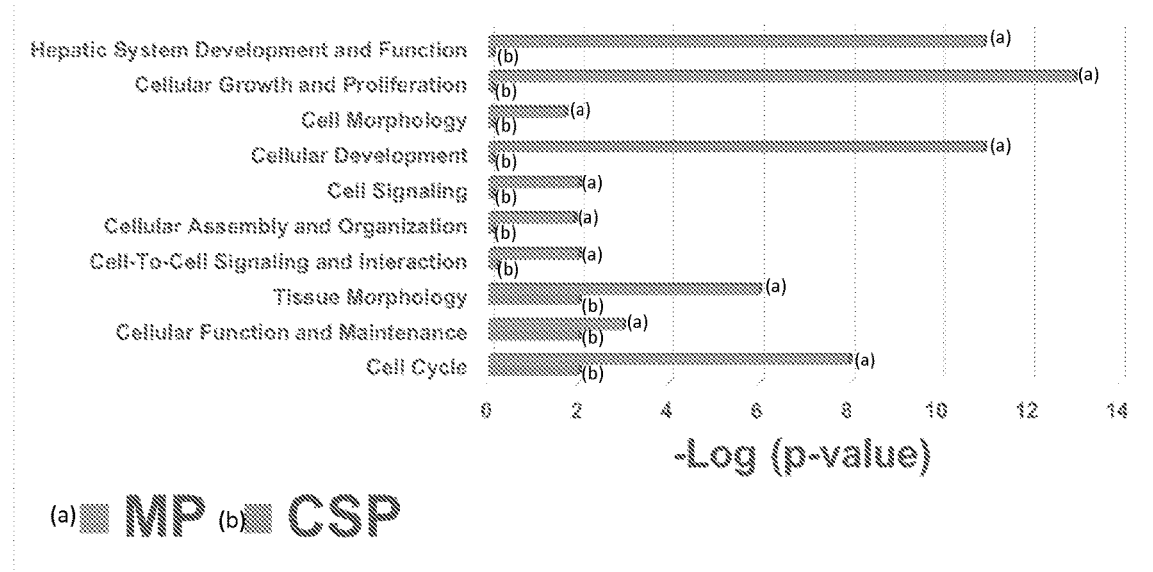
FIG. 9B is a graphic representation of the transcriptomic analysis (microarray) of 20,000 genes obtained from pig liver samples showing the metabolic network analysis (Ingenuity®) following 8 hours of machine perfusion. Effective ex-vivo oxygenation enhanced significantly (p=0.01) the genes regulating biological processes involved in hepatic system development and function, cellular growth and proliferation, cellular morphology, cellular development, cellular signaling, cellular assembly and organization, cell-to-cell signaling and interaction, tissue morphology and cellular function and maintenance. Increased expression of several genes associated with entry of hepatocytes into G1 phase was observed.
Figure 10:
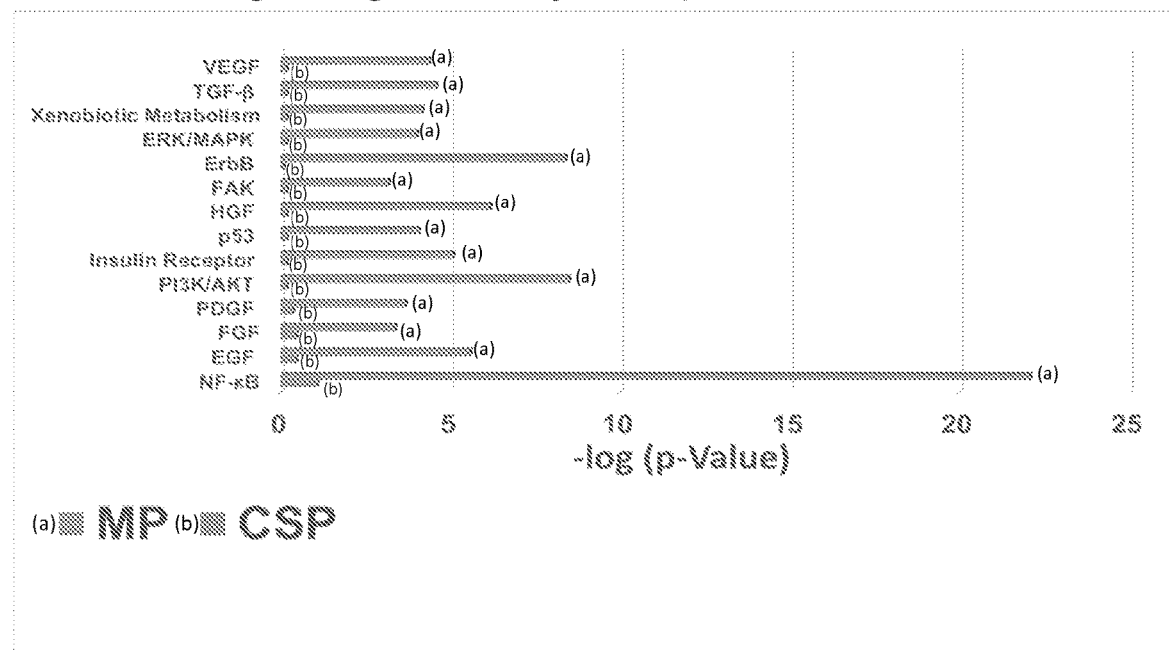
FIG. 10 is a graphic representation of the transcriptomic analysis (microarray) of 20,000 genes obtained from pig liver samples showing the metabolic network analysis (Ingenuity®) following 8 hours of machine perfusion. Effective ex-vivo oxygenation enhanced significantly (p=0.01) the genes expression of signaling pathways that are critical for liver growth. NF-κB can inhibit the TNF-α induced apoptotic pathway and increase the expression of survival gene products.
Figure 11:
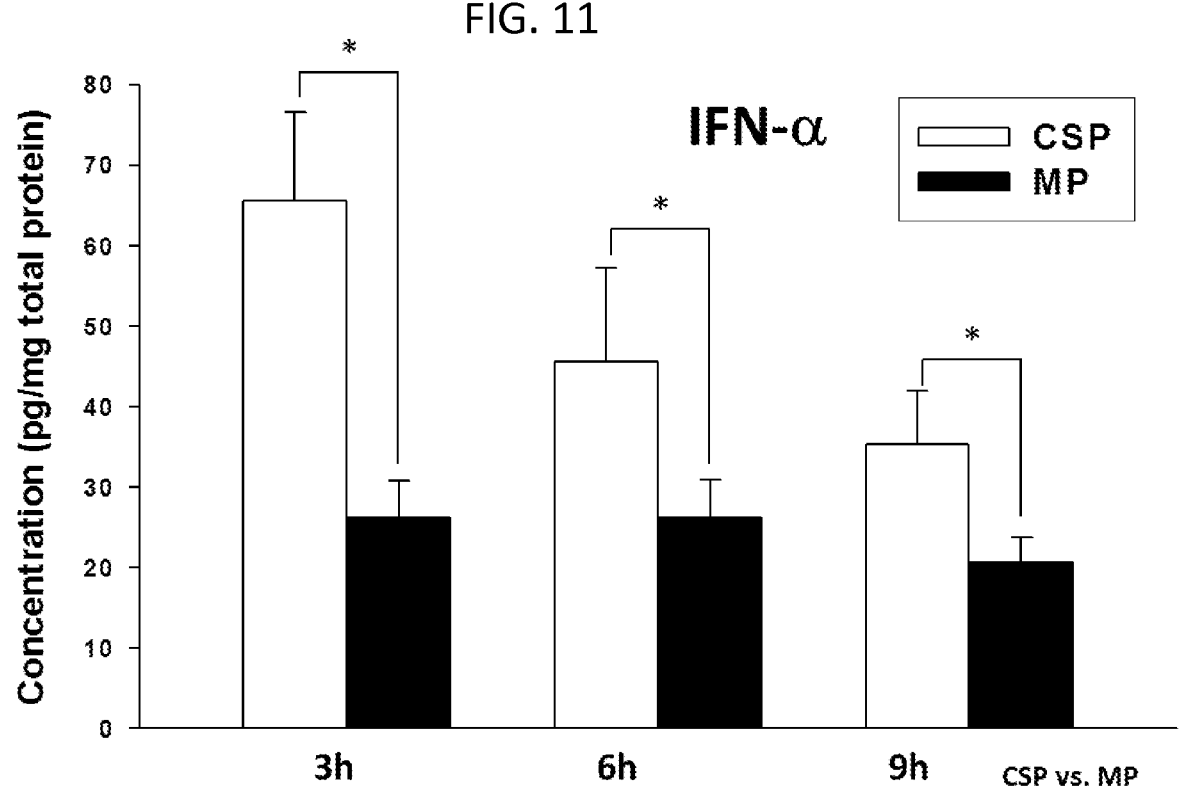
FIG. 11 is a graph showing interferon-α levels in control (cold ischemia) and experimental (machine perfusion) samples. Overall two-way ANOVA p=0.001.
Figure 12:
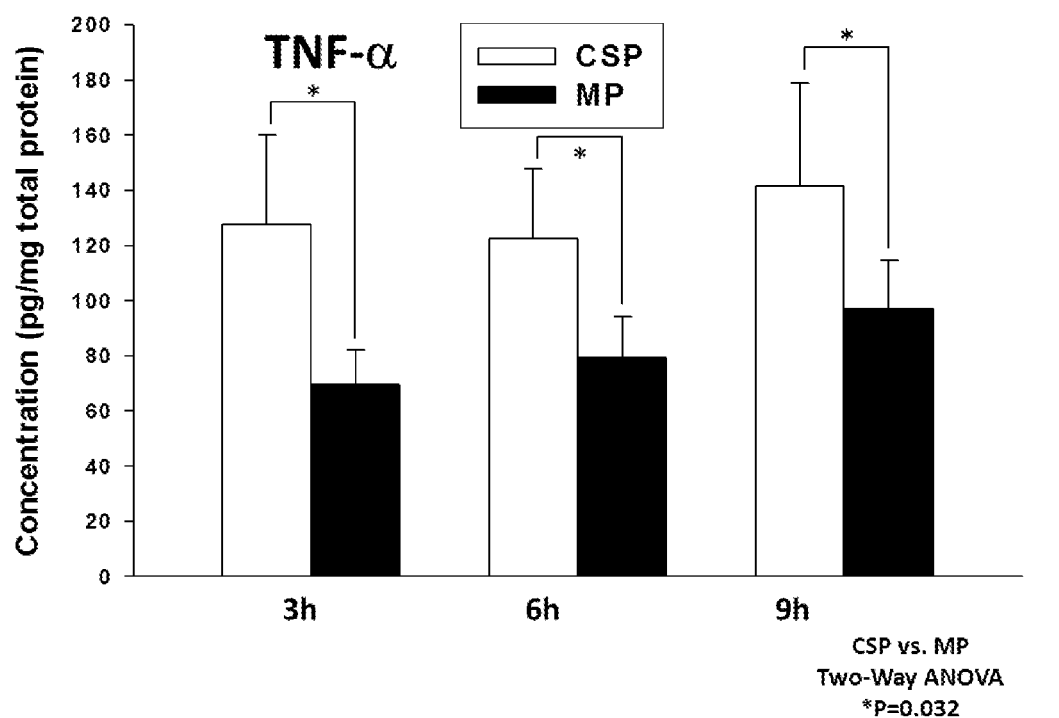
FIG. 12 is a graph showing tumor necrosis factor-α levels in control (cold ischemia) and experimental (machine perfusion) samples. Overall two-way ANOVA p=0.032.
Figure 13:
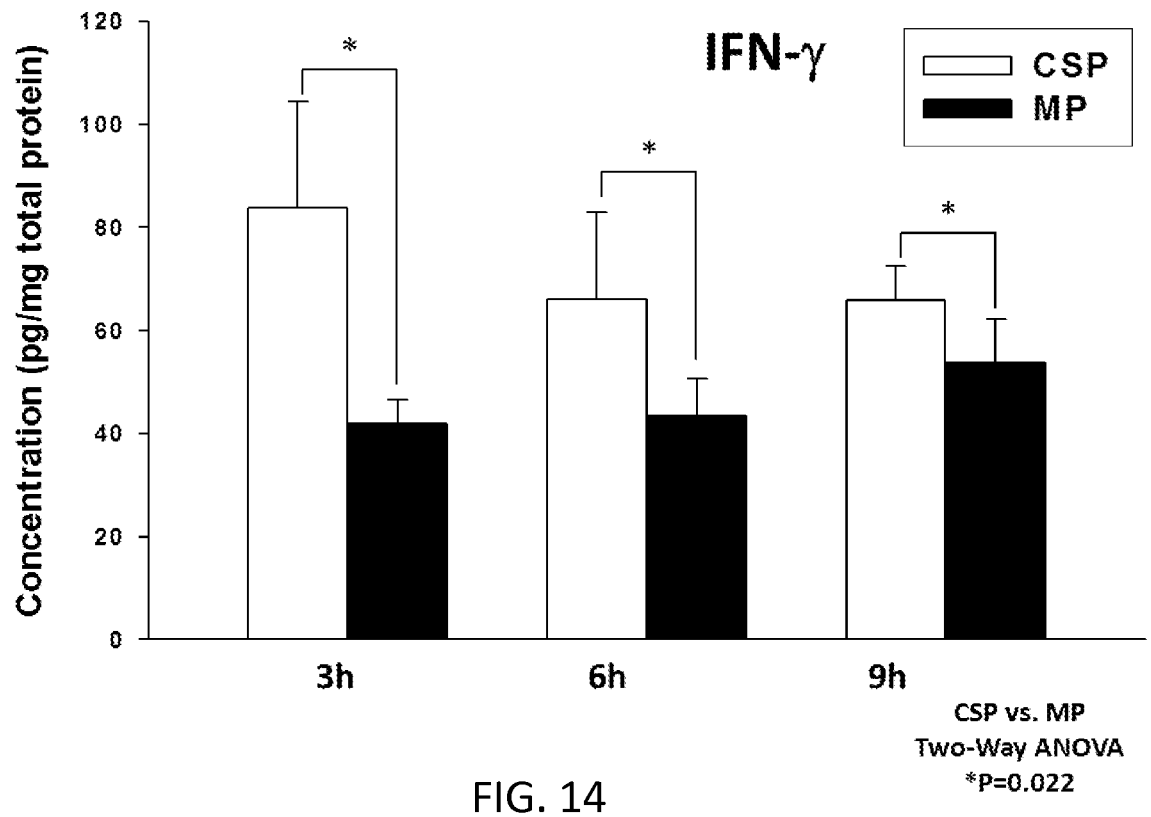
FIG. 13 is a graph showing interferon-γ levels in control (cold ischemia) and experimental (machine perfusion) samples. Overall two-way ANOVA p=0.022.
Figure 14:
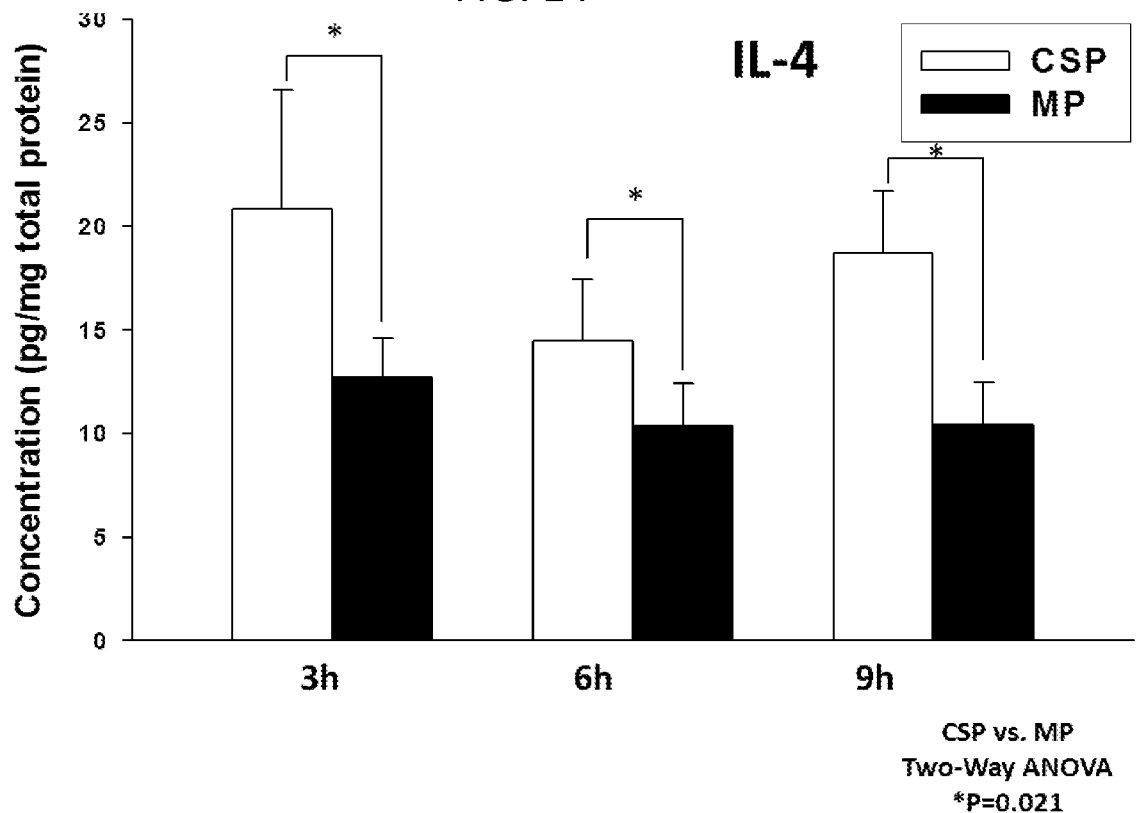
FIG. 14 is a graph showing interleukin-4 levels in control (cold ischemia) and experimental (machine perfusion) samples. Overall two-way ANOVA p=0.021.
Figure 15:
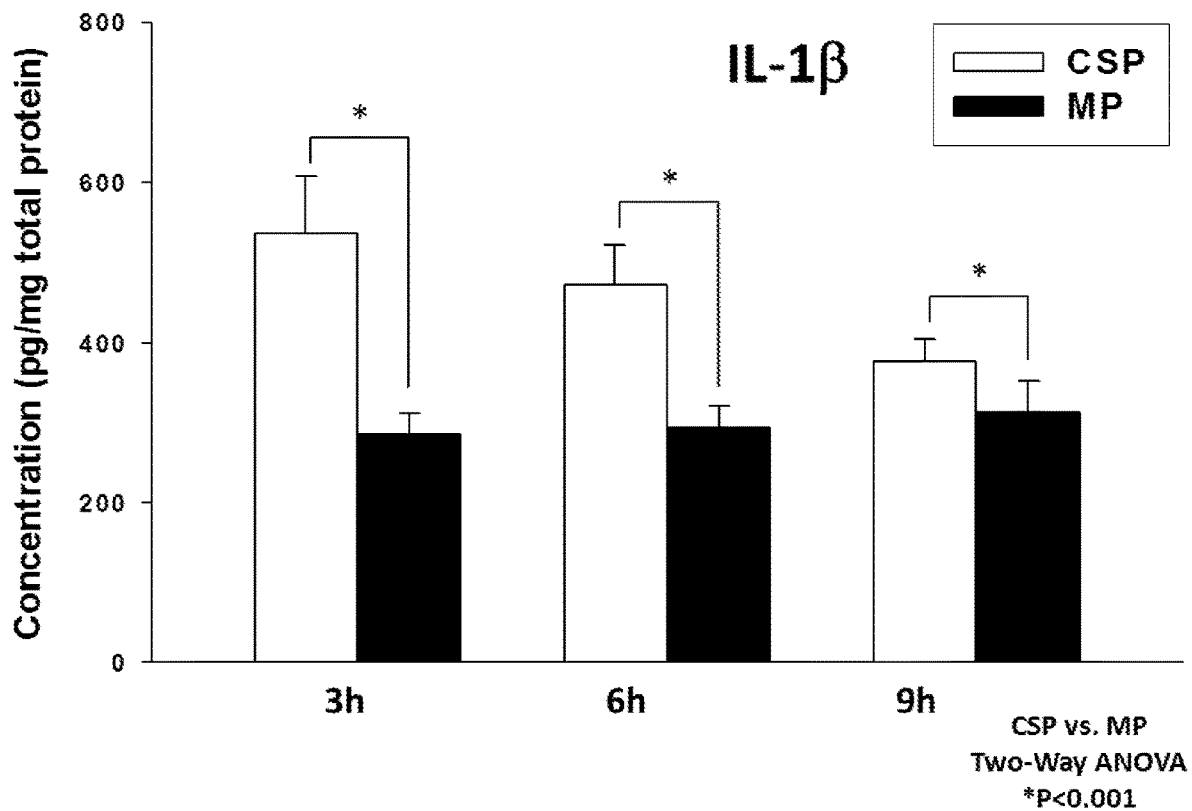
FIG. 15 is a graph showing interleukin-1β levels in control (cold ischemia) and experimental (machine perfusion) samples. Overall two-way ANOVA p=0.001.
Figure 16:
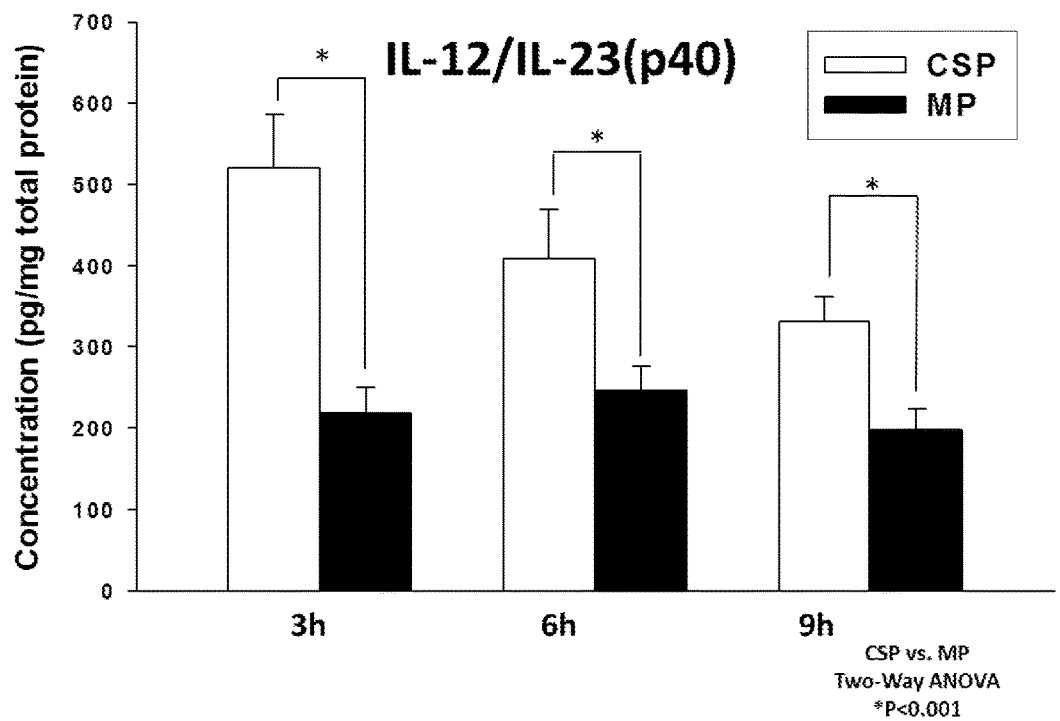
FIG. 16 is a graph showing interleukin-12/interleukin-23 (p40) levels in control (cold ischemia) and experimental (machine perfusion) samples. Overall two-way ANOVA p=0.001.

Enrichment by biological process networks following MP suggested a marked up-regulation of genes related to metabolic process (34%), cellular process (25%), cell communication (17%), as well as additional effects on system process (9%), cell cycle (7%), and cell adhesion (5%) (FIG. 8). Metabolic Network Analysis (Ingenuity Software©) showed significant up-regulation of genes related to drug, amino acid, vitamin, mineral, and carbohydrate metabolism, free radical scavenging, and energy production in the MP group (FIG. 9A). Additional Biological Process Network Analysis (Ingenuity Software©) showed a significant (p<0.05) difference in gene expression related to hepatic system development and function, cellular growth and proliferation, cellular development, and cell cycle when MP was compared to CSP (FIG. 9B). Metabolic Network Analysis (Ingenuity Software©) showed significant up-regulation of genes related to drug, amino acid, vitamin, mineral, and carbohydrate metabolism, free radical scavenging, and energy production in the MP group. Thus, MP with full oxygenation enhances signaling pathways for HGF, EGF, TGF-β, ErbB and PI3K/AKT among others, and triggers proliferative and regenerative transcriptional pathways when compared to CSP (FIG. 10).

Example 3

Cytokine Profiling

This example describes the cytokine profile of tissue samples from control and study group animals.

Additional tissue assays were performed with Affymetrix pig 9 plex Luminex analysis. Approximately 50 mg of the tissue was transferred to a 2.0 ml microcentrifuge tube containing 1 ml of 1×BioSource tissue extraction reagent (San Diego, Calif.) (Catalog Number FNN0071) supplemented with 10 ml of 100 mM phenylmethanesulfonyl fluoride in ethanol as a protease inhibitor. The tissue was homogenized for 15-30 sec until the sample was in a consistent solution. The sample was placed on ice, if processing multiple samples, and was then centrifuged at 4° C. for 10 min at 10,000×g. After centrifugation, the supernatant was collected and placed in a new microcentrifuge tube, placed on ice, and assayed for protein content using the bicinchoninic acid (BCA) protein assay (Pierce, Rockford, Ill.) using the manufacturer's protocol. Depending on tissue type, a 1:5 or 1:10 dilution was necessary before addition of samples to the BCA assay.

Pig cytokines (INF-α, IFN-γ, IL-10, IL-12/IL-23 (p40), IL-1β, IL-4, IL-6, IL-8 and TNF-α) were detected using a Luminex™ 100 IS apparatus using the BioSource International Pig 9 plex LUMINEX beadset. Cytokine levels are presented as mean±SEM. Differences between the levels of a given cytokine measured in flash-frozen tissue vs. RNALATER™-preserved tissue were assessed by Student's t-test analysis using SigmaStat™ software (SPSS, Chicago, Ill.).

Cytokine levels are shown in FIGS. 11-16. Multiple protein-level inflammatory mediators in both tissue and perfusate were significantly (p<0.05) different between groups. MP was associated with downregulation of both type I (IFN-α) and type II (IFN-γ) interferons, consistent with prior studies that showed elevated inflammation and apoptosis subsequent to IR due to the IRF-1 pathway in CSP. The suggestion of a protective mechanism provided by sustainable oxygenation ex vivo was further reinforced by the significant difference in IL-4 levels in the tissues of the MP group. MP was associated with downregulated TNF-α levels in liver tissue when compared to CSP. This detrimental TNF-α activation pathway seen in the CSP group was further corroborated by higher levels of additional Kupffer cells mediators IL-1β and IL-12/IL-23 p40 found on liver tissues. MP down-regulated IL-2 expression progressively during preservation when compared to CSP, which might contribute to lower T cell activation after organ implantation.

Example 4

Metabolomic Analysis

This example describes the metabolomics analysis of samples from control and study group animals.

Metabolomic analysis was performed on 27 perfusate and 31 bile samples (Tables 3 and 4, respectively) by Metabolon (Durham, N.C.). Following receipt, samples were inventoried, and immediately stored at −80° C. At the time of analysis, samples were extracted and prepared for analysis using Metabolon's standard solvent extraction method. The extracted samples were split into equal parts for analysis on the GC/MS and LC/MS/MS platforms. Also included were several technical replicate samples created from a homogeneous pool containing a small amount of all study samples.

TABLE 3

Liver Perfusate samples

| | Time Point | | |
|---|---|---|---|
| Treatment | 0 h | 6 h | 9 h |
| Cold static perfusion in UW buffer (UW/CSP) | n = 2 | n = 4 | n = 4 |
| Machine perfusion in HBOC buffer (HBOC/MP) | n = 6 | n = 6 | n = 5 |

TABLE 4

Bile samples

| | Time Point | | |
|---|---|---|---|
| Treatment | 0-4 h | 16-24 h | 64-72 h |
| Cold static perfusion in UW buffer (UW/CSP) | n = 4 | n = 5 | n = 4 |
| Machine perfusion in HBOC buffer (HBOC/MP) | n = 6 | n = 6 | n = 6 |

TABLE 5

Data Quality: Instrument and Process Variability

| QC Sample | Measurement | Liver Perfusate Median RSD | Bile Median RSD |
|---|---|---|---|
| Internal Standards | Instrument Variability | 6% | 8% |
| Endogenous Biochemicals | Total Process Variability | 10% | 11% |

Instrument variability was determined by calculating the median relative standard deviation (RSD) for the internal standards that were added to each sample prior to injection into the mass spectrometers. Overall process variability was determined by calculating the median RSD for all endogenous metabolites (non-instrument standards) present in 100% of the Client Matrix samples, which are technical replicates of pooled client samples. Values for instrument and process variability met Metabolon's acceptance criteria as shown in the Table 5, above. There were 223 compounds of known identity (named biochemicals) in liver perfusate and 377 named biochemicals in bile. Following log transformation and imputation of missing values, if any, with the minimum observed value for each compound, Welch's two-sample t-tests were used to identify biochemicals that differed significantly between experimental groups. A summary of the numbers of biochemicals that achieved statistical significance ($p \leq 0.05$), as well as those approaching significance ($0.05 < p < 0.10$), is shown below (Tables 6 and 7).

TABLE 6

Summary of biochemicals that differed in liver perfusate samples between groups
Statistical Comparisons (Perfusate)

| Welch's Two-Sample t-Test | Total biochemicals $p \leq 0.05$ | Bio-chemicals (↑↓) | Total biochemicals $0.05 < p < 0.10$ | Bio-chemicals (↑↓) |
|---|---|---|---|---|
| HBOC/MP 0 h UW/CSP 0 h | 49 | 24 \| 25 | 19 | 4 \| 15 |
| HBOC/MP 6 h UW/CSP 6 h | 140 | 89 \| 51 | 15 | 9 \| 6 |
| HBOC/MP 9 h UW/CSP 9 h | 121 | 81 \| 40 | 25 | 11 \| 14 |
| UW/CSP 6 h UW/CSP 0 h | 17 | 16 \| 1 | 18 | 17 \| 1 |
| UW/CSP 9 h UW/CSP 0 h | 22 | 22 \| 0 | 14 | 12 \| 2 |
| UW/CSP 9 h UW/CSP 6 h | 2 | 0 \| 2 | 4 | 1 \| 3 |
| HBOC/MP 6 h HBOC/MP 0 h | 171 | 153 \| 18 | 12 | 11 \| 1 |
| HBOC/MP 9 h HBOC/MP 0 h | 154 | 137 \| 17 | 14 | 14 \| 0 |
| HBOC/MP 9 h HBOC/MP 6 h | 17 | 9 \| 8 | 10 | 5 \| 5 |

TABLE 7

Summary of biochemicals that differed in bile samples between groups
Statistical Comparisons (Bile)

| Welch's Two-Sample t-Test | Total biochemicals $p \leq 0.05$ | Bio-chemicals (↑↓) | Total biochemicals $0.05 < p < 0.10$ | Bio-chemicals (↑↓) |
|---|---|---|---|---|
| HBOC/MP 0-4 UW/CSP 0-4 | 68 | 35 \| 33 | 26 | 10 \| 16 |
| HBOC/MP 16-24 UW/CSP 16-24 | 68 | 14 \| 54 | 37 | 15 \| 22 |
| HBOC/MP 64-72 UW/CSP 64-72 | 39 | 35 \| 4 | 31 | 18 \| 13 |
| UW/CSP 16-24 UW/CSP 0-4 | 88 | 58 \| 30 | 32 | 17 \| 15 |
| UW/CSP 64-72 UW/CSP 0-4 | 82 | 7 \| 75 | 33 | 7 \| 26 |
| UW/CSP 64-72 UW/CSP 16-24 | 63 | 2 \| 61 | 40 | 1 \| 39 |
| HBOC/MP 16-24 HBOC/MP 0-4 | 134 | 58 \| 76 | 26 | 10 \| 16 |
| HBOC/MP 64-72 HBOC/MP 0-4 | 176 | 35 \| 141 | 28 | 7 \| 21 |
| HBOC/MP 64-72 HBOC/MP 16-24 | 68 | 3 \| 65 | 32 | 4 \| 28 |

Figure 17A:
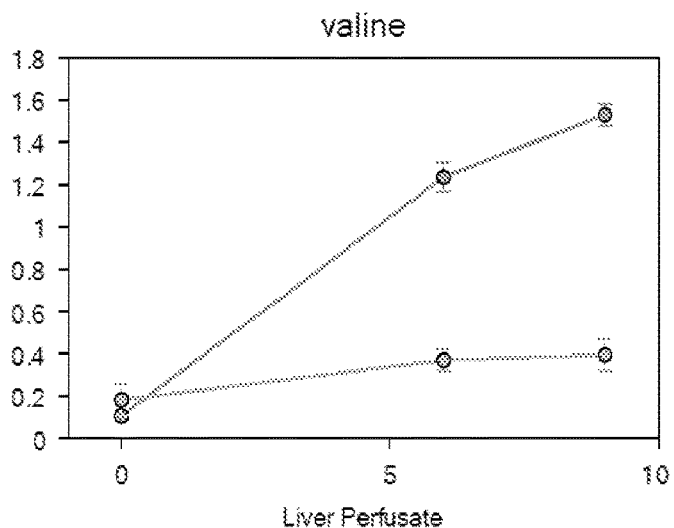
FIGS. 17A-17C are a series of graphs showing branched chain amino acids in machine perfused livers and cold ischemia livers over the course of the experiment (hours).
Figure 17B:
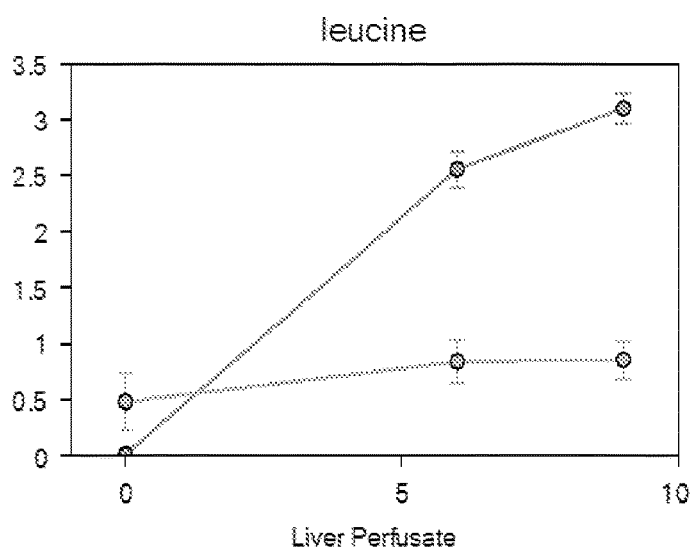
Figure 17C:
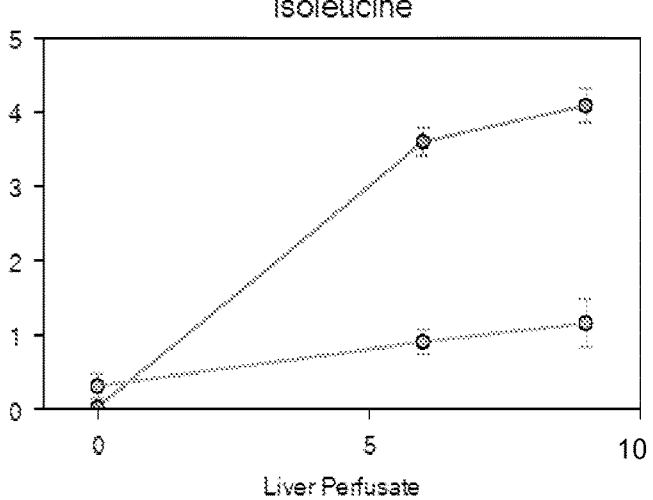
Figure 18A:
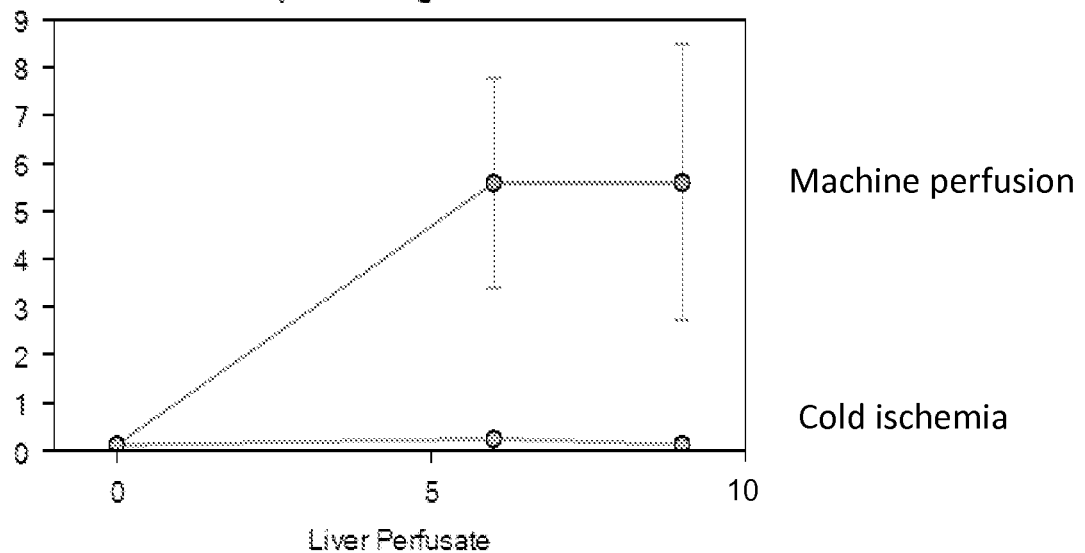
FIGS. 18A-18B are a series of graphs showing Krebs pathway byproducts in machine perfused livers and cold ischemia livers over the course of the experiment (hours).
Figure 18B:
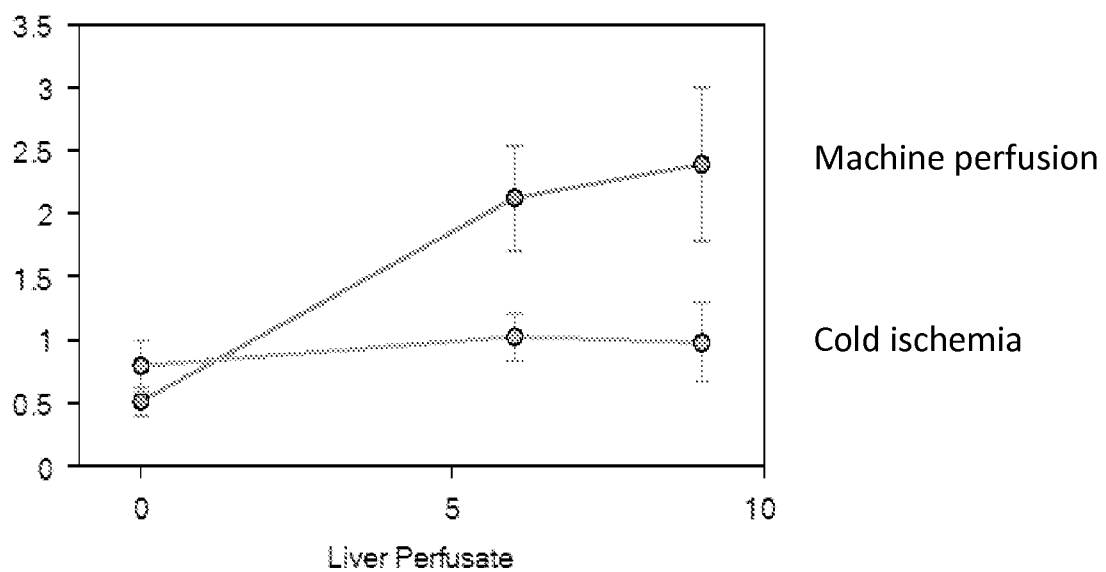

Perfusate Results MP with HBOC had a bigger impact on the metabolic profile over time than cold static perfusion (CSP). Perfusate profiling revealed differences in stress responses over time between the two preservation conditions. Biochemicals that provide insight into oxidative, inflammatory, and energy stress were among those showing a strong separation between perfusate profiles from the two preservation conditions. Possible signs of energy stress and purine nucleotide breakdown were noted in the UW/CSP-preserved livers as indicated by the significantly higher levels of AMP, nucleosides adenosine, guanosine, and inosine, as well as the inosine deamination product hypoxanthine. Evidence of lipoxygenase activity was observed and differed by preservation method. Altogether this suggested that inflammation was greater in the UW/CSP than HBOC/MP samples. The glucose-amino acid cycle and branched-chain amino acid mobilization were markedly elevated in HBOC/MP samples. Branched-chain amino acid (BCAA) oxidation showed a strong differential increase in HBOC/MP perfusates at the 6 and 9 h time points (FIG. 17A-17C). In addition, byproducts of the Krebs cycle showed significant differences between the groups (FIGS. 18A-18B). These could potentially be used as a marker for adequate aerobic metabolism in tissues experiencing previous ischemic insult.

Bile Results Bile acid release during perfusion was suppressed but sterol synthesis after transplant was increased in the HBOC/MP group. Five bile acid conjugates were detected in UW/CSP liver perfusates but were not detected or detected at very low levels in HBOC/MP perfusates, which reinforces the argument towards the inability to sustain effective bile acid conjugation during CSP. MP-treated livers made but did not release glycochenodeoxycholate during perfusion but resumed its secretion almost immediately following liver reperfusion. Although campesterol levels in both treatment groups started out similarly, they remained stable in bile samples collected from MP-preserved livers but rapidly tapered off in bile from UW/CSP-preserved livers. MP-preserved livers were able to adequately support bile-mediated nutrient extraction whereas UW/CSP-preserved livers appeared to be less capable of doing so.

After this initial analysis, biomarkers have been grouped by divergent biochemical pathways within known molecular groups (Tables 8 and 9). Analysis of additional markers in control and study group liver perfusate is shown in FIGS. 19A-19W.

TABLE 8

Biomarkers in perfusate, grouped by divergent pathways within known molecular groups/pathways

| Super Pathway | Sub Pathway | Biochemical Name | Platform | Comp ID |
|---|---|---|---|---|
| Amino acid | Glycine, serine and threonine metabolism | glycine | GC/MS | 11777 |
| | | N-acetylglycine | GC/MS | 27710 |
| | | beta-hydroxypyruvate | GC/MS | 15686 |
| | | serine | GC/MS | 1648 |
| | | threonine | GC/MS | 1284 |
| | | betaine | LC/MS pos | 3141 |
| | Alanine and aspartate metabolism | aspartate | GC/MS | 15996 |
| | | beta-alanine | GC/MS | 55 |
| | | alanine | GC/MS | 1126 |
| | Glutamate metabolism | glutamate | GC/MS | 57 |
| | | 4-hydroxyglutamate | GC/MS | 40499 |
| | | glutamine | GC/MS | 1647 |
| | | pyroglutamine* | LC/MS pos | 32672 |
| | | gamma-aminobutyrate (GABA) | GC/MS | 1416 |
| | Histidine metabolism | histidine | LC/MS neg | 59 |
| | Lysine metabolism | lysine | GC/MS | 1301 |
| | | 2-aminoadipate | GC/MS | 6146 |
| | Phenylalanine & tyrosine metabolism | phenylalanine | LC/MS pos | 64 |
| | | tyrosine | LC/MS pos | 1299 |
| | | phenylacetylglycine | LC/MS neg | 33945 |
| | | phenol sulfate | LC/MS neg | 32553 |
| | | 5-hydroxymethyl-2-furoic acid | GC/MS | 42040 |
| | Tryptophan metabolism | tryptophan | LC/MS pos | 54 |
| | | C-glycosyltryptophan* | LC/MS pos | 32675 |
| | | 3-indoxyl sulfate | LC/MS neg | 27672 |
| | Valine, leucine and isoleucine metabolism | 3-methyl-2-oxobutyrate | LC/MS neg | 21047 |
| | | 3-methyl-2-oxovalerate | LC/MS neg | 15676 |
| | | beta-hydroxyisovalerate | GC/MS | 12129 |
| | | isoleucine | LC/MS pos | 1125 |
| | | leucine | LC/MS pos | 60 |
| | | tigloylglycine | LC/MS pos | 1598 |
| | | valine | LC/MS pos | 1649 |
| | | 4-methyl-2-oxopentanoate | LC/MS neg | 22116 |
| | | isovalerylglycine | LC/MS neg | 35107 |
| | | 2-methylbutyrylglycine | LC/MS neg | 31928 |
| | | 3-methylglutarylcarnitine (C6) | LC/MS pos | 37060 |
| | Cysteine, methionine, SAM, taurine metabolism | cysteine | GC/MS | 31453 |
| | | N-acetylcysteine | LC/MS pos | 1586 |
| | | S-methylcysteine | GC/MS | 40262 |
| | | cystine | GC/MS | 39512 |
| | | hypotaurine | GC/MS | 590 |
| | | taurine | GC/MS | 2125 |
| | | S-adenosylhomocysteine (SAH) | LC/MS neg | 15948 |
| | | methionine | LC/MS pos | 1302 |
| | | 2-hydroxybutyrate (AHB) | GC/MS | 21044 |
| | | 4-methylthio-2-oxobutanoate | LC/MS neg | 40732 |
| | Urea cycle; arginine-, proline-, metabolism | ornithine | GC/MS | 1493 |
| | | urea | GC/MS | 1670 |
| | | proline | LC/MS pos | 1898 |
| | Creatine metabolism | creatine | LC/MS pos | 27718 |
| | | creatinine | LC/MS pos | 513 |
| | Butanoate metabolism | 2-aminobutyrate | GC/MS | 1577 |
| | Polyamine metabolism | 5-methylthioadenosine (MTA) | LC/MS pos | 1419 |
| | | putrescine | GC/MS | 1408 |
| | | spermidine | GC/MS | 485 |
| | | spermine | LC/MS pos | 603 |
| | Glutathione metabolism | glutathione, reduced (GSH) | LC/MS pos | 2127 |
| | | S-methylglutathione | LC/MS pos | 33944 |
| | | 5-oxoproline | LC/MS neg | 1494 |
| | | glutathione, oxidized (GSSG) | LC/MS pos | 38783 |
| | | cysteine-glutathione disulfide | LC/MS pos | 35159 |
| | | ophthalmate | LC/MS pos | 34592 |
| Peptide | Dipeptide | glycylglycine | GC/MS | 21030 |
| | | cysteinylglycine | GC/MS | 35637 |
| | Dipeptide derivative | carnosine | LC/MS neg | 1768 |
| | gamma-glutamyl | gamma-glutamylvaline | LC/MS pos | 32393 |
| | | gamma-glutamylleucine | LC/MS pos | 18369 |
| | | gamma-glutamylisoleucine* | LC/MS pos | 34456 |
| | | gamma-glutamylmethionine | LC/MS pos | 37539 |
| | | gamma-glutamylglutamate | LC/MS pos | 36738 |
| | | gamma-glutamylphenylalanine | LC/MS pos | 33422 |
| | | gamma-glutamyltyrosine | LC/MS pos | 2734 |

TABLE 8-continued

Biomarkers in perfusate, grouped by divergent pathways within known molecular groups/pathways

| Super Pathway | Sub Pathway | Biochemical Name | Platform | Comp ID |
|---|---|---|---|---|
| Carbohydrate | Aminosugars metabolism | erythronate* | GC/MS | 33477 |
| | Fructose, mannose, galactose, starch, and sucrose metabolism | fructose | GC/MS | 577 |
| | | galactitol (dulcitol) | GC/MS | 1117 |
| | | galactose | GC/MS | 12055 |
| | | maltose | GC/MS | 15806 |
| | | mannose | GC/MS | 584 |
| | | mannose-6-phosphate | GC/MS | 1469 |
| | | Isobar: sorbitol, mannitol | LC/MS pos | 33004 |
| | | sucrose | LC/MS neg | 1519 |
| | | maltotriose | LC/MS neg | 15913 |
| | | raffinose | LC/MS neg | 586 |
| | | verbascose | LC/MS neg | 37132 |
| | | palatinitol | GC/MS | 37469 |
| | Oligosaccharide | lactobionate | GC/MS | 20685 |
| | Glycolysis, gluconeogenesis, pyruvate metabolism | glycerate | GC/MS | 1572 |
| | | glucose-6-phosphate (G6P) | GC/MS | 31260 |
| | | glucose | GC/MS | 31263 |
| | | fructose-6-phosphate | GC/MS | 12021 |
| | | 3-phosphoglycerate | GC/MS | 1414 |
| | | dihydroxyacetone phosphate (DHAP) | GC/MS | 15522 |
| | | 1,3-dihydroxyacetone | GC/MS | 35963 |
| | | phosphoenolpyruvate (PEP) | GC/MS | 597 |
| | | pyruvate | GC/MS | 599 |
| | | lactate | GC/MS | 527 |
| | Glyoxylate and dicarboxylate metabolism | oxalate (ethanedioate) | GC/MS | 20694 |
| | Nucleotide sugars, pentose metabolism | 6-phosphogluconate | GC/MS | 15442 |
| | | arabitol | GC/MS | 38075 |
| | | ribitol | GC/MS | 15772 |
| | | threitol | GC/MS | 35854 |
| | | sedoheptulose-7-phosphate | GC/MS | 35649 |
| | | gluconate | GC/MS | 587 |
| | | ribose | GC/MS | 12080 |
| | | ribose 5-phosphate | GC/MS | 561 |
| | | ribose 1-phosphate | GC/MS | 1763 |
| | | ribulose | GC/MS | 35855 |
| | | Isobar: ribulose 5-phosphate, xylulose 5-phosphate | GC/MS | 37288 |
| | | xylitol | GC/MS | 4966 |
| | | xylose | GC/MS | 15835 |
| | | xylonate | GC/MS | 35638 |
| | | xylulose | GC/MS | 18344 |
| Secondary Metabolism | Advanced glycation end-product | erythrulose | GC/MS | 37427 |
| Energy | Krebs cycle | citrate | LC/MS neg | 1564 |
| | | alpha-ketoglutarate | GC/MS | 33453 |
| | | succinate | GC/MS | 1437 |
| | | fumarate | GC/MS | 1643 |
| | | malate | GC/MS | 1303 |
| | Oxidative phosphorylation | acetylphosphate | GC/MS | 15488 |
| | | phosphate | GC/MS | 11438 |
| | | pyrophosphate (PPi) | GC/MS | 2078 |
| Lipid | Essential fatty acid | linoleate (18:2n6) | LC/MS neg | 1105 |
| | | linolenate [alpha or gamma; (18:3n3 or 6)] | LC/MS neg | 34035 |
| | | dihomo-linolenate (20:3n3 or n6) | LC/MS neg | 35718 |
| | | eicosapentaenoate (EPA; 20:5n3) | LC/MS neg | 18467 |
| | | docosapentaenoate (n3 DPA; 22:5n3) | LC/MS neg | 32504 |
| | | docosahexaenoate (DHA; 22:6n3) | LC/MS neg | 19323 |
| | Medium chain fatty acid | caproate (6:0) | LC/MS neg | 32489 |
| | | caprylate (8:0) | LC/MS neg | 32492 |
| | | 2-aminoheptanoic acid | LC/MS pos | 43761 |
| | Long chain fatty acid | oleate (18:1n9) | GC/MS | 1359 |
| | | arachidate (20:0) | LC/MS neg | 44679 |
| | | eicosenoate (20:1n9 or 11) | LC/MS neg | 33587 |
| | | dihomo-linoleate (20:2n6) | LC/MS neg | 17805 |
| | | mead acid (20:3n9) | LC/MS neg | 35174 |
| | | arachidonate (20:4n6) | LC/MS neg | 1110 |
| | Fatty acid, monohydroxy | 3-hydroxypropanoate | GC/MS | 42103 |
| | | 4-hydroxybutyrate (GHB) | GC/MS | 34585 |
| | | 13-HODE + 9-HODE | LC/MS neg | 37752 |

TABLE 8-continued

Biomarkers in perfusate, grouped by divergent pathways within known molecular groups/pathways

| Super Pathway | Sub Pathway | Biochemical Name | Platform | Comp ID |
|---|---|---|---|---|
| | Fatty acid, dicarboxylate | 4-hydroxy-2-oxoglutaric acid | GC/MS | 40062 |
| | | hexadecanedioate | LC/MS neg | 35678 |
| | | octadecanedioate | LC/MS neg | 36754 |
| | Eicosanoid | 12-HETE | LC/MS neg | 37536 |
| | | 15-HETE | LC/MS neg | 37538 |
| | Fatty acid metabolism (also BCAA metabolism) | propionylcarnitine | LC/MS pos | 32452 |
| | | propionylglycine | LC/MS neg | 31932 |
| | | butyrylcarnitine | LC/MS pos | 32412 |
| | Carnitine metabolism | carnitine | LC/MS pos | 15500 |
| | | acetylcarnitine | LC/MS pos | 32198 |
| | Bile acid metabolism | glycocholate | LC/MS neg | 18476 |
| | | taurocholate | LC/MS neg | 18497 |
| | | glycochenodeoxycholate | LC/MS neg | 32346 |
| | | glycolithocholate | LC/MS neg | 31912 |
| | | taurolithocholate | LC/MS neg | 31889 |
| | | glycohyodeoxycholic acid | LC/MS pos | 43501 |
| | Glycerolipid metabolism | ethanolamine | GC/MS | 34285 |
| | | phosphoethanolamine | GC/MS | 12102 |
| | | choline | LC/MS pos | 15506 |
| | | glycerol 3-phosphate (G3P) | GC/MS | 15365 |
| | | glycerophosphorylcholine (GPC) | LC/MS pos | 15990 |
| | Inositol metabolism | myo-inositol | GC/MS | 19934 |
| | | scyllo-inositol | GC/MS | 32379 |
| | Ketone bodies | 3-hydroxybutyrate (BHBA) | GC/MS | 542 |
| | | acetoacetate | GC/MS | 33963 |
| | | 1,2-propanediol | GC/MS | 38002 |
| | Lysolipid | 1-arachidonoylglycerophosphoethanolamine* | LC/MS neg | 35186 |
| | | 1-palmitoylglycerophosphocholine (16:0) | LC/MS neg | 33955 |
| | | 1-oleoylglycerophosphocholine (18:1) | LC/MS neg | 33960 |
| | | 1-linoleoylglycerophosphocholine (18:2n6) | LC/MS neg | 34419 |
| | | 2-linoleoylglycerophosphocholine* | LC/MS neg | 38087 |
| | | 1-arachidonoylglycerophosphocholine (20:4n6)* | LC/MS neg | 34061 |
| | Monoacylglycerol | 1-palmitoylglycerol (1-monopalmitin) | GC/MS | 21127 |
| | Sphingolipid | palmitoyl sphingomyelin | GC/MS | 37506 |
| | Sterol/Steroid | pregnanediol-3-glucuronide | LC/MS neg | 40708 |
| Nucleotide | Purine metabolism, (hypo)xanthine/inosine containing | xanthine | LC/MS neg | 3147 |
| | | xanthosine | LC/MS neg | 15136 |
| | | hypoxanthine | LC/MS neg | 3127 |
| | | inosine | LC/MS neg | 1123 |
| | | 2'-deoxyinosine | LC/MS neg | 15076 |
| | Purine metabolism, adenine containing | adenine | LC/MS pos | 554 |
| | | adenosine | LC/MS pos | 555 |
| | | N6-methyladenosine | LC/MS pos | 37114 |
| | | adenosine 5'-monophosphate (AMP) | LC/MS pos | 32342 |
| | | adenosine-2',3'-cyclic monophosphate | LC/MS pos | 37467 |
| | | N6,N6-dimethyladenosine | LC/MS pos | 42081 |
| | Purine metabolism, guanine containing | guanine | LC/MS pos | 32352 |
| | | guanosine | LC/MS neg | 1573 |
| | | isoguanine | GC/MS | 42958 |
| | Purine metabolism, urate metabolism | urate | GC/MS | 1604 |
| | | allantoin | GC/MS | 1107 |
| | Pyrimidine metabolism, cytidine containing | cytidine | LC/MS neg | 514 |
| | Pyrimidine metabolism, thymine containing; Valine, leucine and isoleucine metabolism/ | 3-aminoisobutyrate | GC/MS | 1566 |
| | Pyrimidine metabolism, uracil containing | uracil | GC/MS | 605 |
| | | uridine | LC/MS neg | 606 |
| | Purine and pyrimidine metabolism | methylphosphate | GC/MS | 37070 |
| Cofactors and vitamins | Ascorbate and aldarate metabolism | ascorbate (Vitamin C) | GC/MS | 1640 |
| | | threonate | GC/MS | 27738 |
| | | arabonate | GC/MS | 37516 |
| | Hemoglobin and porphyrin metabolism | heme | LC/MS neg | 41754 |
| | | L-urobilin | LC/MS pos | 40173 |
| | Nicotinate and nicotinamide | nicotinamide | LC/MS pos | 594 |

TABLE 8-continued

Biomarkers in perfusate, grouped by divergent pathways within known molecular groups/pathways

| Super Pathway | Sub Pathway | Biochemical Name | Platform | Comp ID |
|---|---|---|---|---|
| | metabolism | N1-Methyl-2-pyridone-5-carboxamide | LC/MS pos | 40469 |
| | Pantothenate and CoA metabolism | pantothenate | LC/MS neg | 1508 |
| | Riboflavin metabolism | riboflavin (Vitamin B2) | LC/MS pos | 1827 |
| Xenobiotics | Benzoate metabolism | hippurate | LC/MS neg | 15753 |
| | | 2-hydroxyhippurate (salicylurate) | LC/MS neg | 18281 |
| | Chemical | glycolate (hydroxyacetate) | GC/MS | 15737 |
| | | 2-hydroxyisobutyrate | GC/MS | 22030 |
| | | glycerol 2-phosphate | GC/MS | 27728 |
| | | HEPES | LC/MS pos | 21248 |
| | | trizma acetate | GC/MS | 20710 |
| | | 2-ethylhexanoate (isobar with 2-propylpentanoate) | LC/MS neg | 35490 |
| | | ricinoleic acid | LC/MS neg | 37464 |
| | Drug | ketamine | LC/MS pos | 35128 |
| | | allopurinol riboside | GC/MS | 38321 |
| | | vecuronium | LC/MS pos | 42591 |
| | | oxypurinol | GC/MS | 41725 |
| | | allopurinol | GC/MS | 43534 |
| | Food component/Plant | 5-ketogluconate | GC/MS | 15687 |
| | | N-glycolylneuraminate | GC/MS | 37123 |
| | | stachydrine | LC/MS pos | 34384 |
| | | homostachydrine* | LC/MS pos | 33009 |
| | Sugar, sugar substitute, starch | erythritol | GC/MS | 20699 |

TABLE 9

Biomarkers in bile, grouped by divergent pathways within known molecular groups/pathways

| Super Pathway | Sub Pathway | Biochemical Name | Platform | Comp ID |
|---|---|---|---|---|
| Amino acid | Glycine, serine and threonine metabolism | glycine | GC/MS | 11777 |
| | | dimethylglycine | GC/MS | 5086 |
| | | N-acetylglycine | GC/MS | 27710 |
| | | beta-hydroxypyruvate | GC/MS | 15686 |
| | | serine | GC/MS | 1648 |
| | | threonine | LC/MS pos | 1284 |
| | | N-acetylthreonine | LC/MS neg | 33939 |
| | | betaine | LC/MS pos | 3141 |
| | Alanine and aspartate metabolism | asparagine | GC/MS | 34283 |
| | | beta-alanine | GC/MS | 55 |
| | | 3-ureidopropionate | LC/MS pos | 3155 |
| | | N-acetyl-beta-alanine | LC/MS pos | 37432 |
| | | alanine | GC/MS | 1126 |
| | | N-acetylalanine | LC/MS neg | 1585 |
| | Glutamate metabolism | glutamate | LC/MS pos | 57 |
| | | glutamine | LC/MS pos | 53 |
| | Histidine metabolism | histidine | LC/MS neg | 59 |
| | | trans-urocanate | LC/MS pos | 607 |
| | | 1-methylimidazoleacetate | LC/MS pos | 32350 |
| | Lysine metabolism | lysine | LC/MS pos | 1301 |
| | | 2-aminoadipate | LC/MS pos | 6146 |
| | | pipecolate | GC/MS | 1444 |
| | | N6-acetyllysine | LC/MS pos | 36752 |
| | Phenylalanine & tyrosine metabolism | phenyllactate (PLA) | LC/MS neg | 22130 |
| | | phenylalanine | LC/MS pos | 64 |
| | | phenylacetate | GC/MS | 15958 |
| | | p-cresol sulfate | LC/MS neg | 36103 |
| | | m-cresol sulfate | LC/MS neg | 36846 |
| | | tyrosine | LC/MS pos | 1299 |
| | | 3-(4-hydroxyphenyl)lactate | LC/MS neg | 32197 |
| | | vanillylmandelate (VMA) | LC/MS neg | 1567 |
| | | 4-hydroxyphenylpyruvate | LC/MS neg | 1669 |
| | | 4-hydroxyphenylacetate | GC/MS | 541 |
| | | 3,4-dihydroxyphenylacetate | LC/MS neg | 18296 |
| | | phenylacetylglycine | LC/MS neg | 33945 |
| | | phenol sulfate | LC/MS neg | 32553 |
| | | 4-hydroxyphenylacetyl glycine | LC/MS neg | 43525 |

TABLE 9-continued

Biomarkers in bile, grouped by divergent pathways within known molecular groups/pathways

| Super Pathway | Sub Pathway | Biochemical Name | Platform | Comp ID |
|---|---|---|---|---|
| | Tryptophan metabolism | kynurenate | LC/MS neg | 1417 |
| | | kynurenine | LC/MS pos | 15140 |
| | | tryptophan | LC/MS pos | 54 |
| | | indolelactate | GC/MS | 18349 |
| | | N-acetyltryptophan | LC/MS neg | 33959 |
| | | C-glycosyltryptophan* | LC/MS pos | 32675 |
| | | 3-indoxyl sulfate | LC/MS neg | 27672 |
| | Valine, leucine and isoleucine metabolism | 3-methyl-2-oxobutyrate | LC/MS neg | 21047 |
| | | 3-methyl-2-oxovalerate | LC/MS neg | 15676 |
| | | beta-hydroxyisovalerate | GC/MS | 12129 |
| | | alpha-hydroxyisocaproate | GC/MS | 22132 |
| | | isoleucine | LC/MS pos | 1125 |
| | | leucine | LC/MS pos | 60 |
| | | N-acetylleucine | LC/MS pos | 1587 |
| | | N-acetylisoleucine | LC/MS pos | 33967 |
| | | tigloylglycine | LC/MS pos | 1598 |
| | | valine | LC/MS pos | 1649 |
| | | 3-hydroxyisobutyrate | GC/MS | 1549 |
| | | 4-methyl-2-oxopentanoate | LC/MS neg | 22116 |
| | | 3-hydroxy-2-ethylpropionate | GC/MS | 32397 |
| | | alpha-hydroxyisovalerate | GC/MS | 33937 |
| | | isovalerylglycine | LC/MS neg | 35107 |
| | | isobutyrylcarnitine | LC/MS pos | 33441 |
| | | 2-methylbutyrylcarnitine (C5) | LC/MS pos | 35431 |
| | | 2-methylbutyrylglycine | LC/MS pos | 31928 |
| | | 3-methylcrotonylglycine | LC/MS pos | 31940 |
| | | isovalerylcarnitine | LC/MS pos | 34407 |
| | | tiglyl carnitine | LC/MS pos | 35428 |
| | | 3-methylglutarylcarnitine (C6) | LC/MS pos | 37060 |
| | Cysteine, methionine, SAM, taurine metabolism | cysteine | GC/MS | 31453 |
| | | S-methylcysteine | LC/MS pos | 39592 |
| | | cystine | GC/MS | 31454 |
| | | S-adenosylhomocysteine (SAH) | LC/MS neg | 15948 |
| | | methionine | LC/MS pos | 1302 |
| | | N-acetylmethionine | LC/MS neg | 1589 |
| | | 2-hydroxybutyrate (AHB) | GC/MS | 21044 |
| | | homocysteine | GC/MS | 40266 |
| | Urea cycle; arginine-, proline-, metabolism | dimethylarginine (SDMA + ADMA) | LC/MS pos | 36808 |
| | | arginine | LC/MS pos | 1638 |
| | | ornithine | GC/MS | 1493 |
| | | urea | GC/MS | 1670 |
| | | proline | LC/MS pos | 1898 |
| | | citrulline | LC/MS pos | 2132 |
| | | trans-4-hydroxyproline | LC/MS pos | 32306 |
| | | homocitrulline | LC/MS pos | 22138 |
| | | N-delta-acetylornithine* | LC/MS pos | 43249 |
| | | N2,N5-diacetylornithine | LC/MS neg | 43591 |
| | Creatine metabolism | creatine | LC/MS pos | 27718 |
| | | creatinine | LC/MS pos | 513 |
| | Butanoate metabolism | 2-aminobutyrate | LC/MS pos | 32348 |
| | Polyamine metabolism | 5-methylthioadenosine (MTA) | LC/MS pos | 1419 |
| | | acisoga | LC/MS pos | 43258 |
| | Glutathione metabolism | S-methylglutathione | LC/MS pos | 33944 |
| | | 5-oxoproline | LC/MS neg | 1494 |
| | | glutathione, oxidized (GSSG) | LC/MS pos | 27727 |
| | | cysteine-glutathione disulfide | LC/MS pos | 35159 |
| | | ophthalmate | LC/MS pos | 34592 |
| Peptide | Dipeptide | glycylproline | LC/MS pos | 22171 |
| | | leucylleucine | LC/MS pos | 36756 |
| | | pro-hydroxy-pro | LC/MS pos | 35127 |
| | | cysteinylglycine | GC/MS | 35637 |
| | | valylalanine | LC/MS pos | 41518 |
| | | aspartylleucine | LC/MS pos | 40068 |
| | | isoleucylalanine | LC/MS pos | 40046 |
| | | leucylalanine | LC/MS pos | 40010 |
| | | leucylglutamate | LC/MS pos | 40021 |
| | | leucylphenylalanine | LC/MS neg | 40026 |
| | | leucylserine | LC/MS neg | 40048 |
| | | serylleucine | LC/MS pos | 40066 |
| | | threonylleucine | LC/MS pos | 40051 |
| | | tyrosylleucine | LC/MS pos | 40031 |
| | Dipeptide derivative | carnosine | LC/MS neg | 1768 |
| | | anserine | LC/MS neg | 15747 |
| | | cys-gly, oxidized | LC/MS neg | 18368 |
| | | N-acetylcarnosine | LC/MS pos | 43488 |

TABLE 9-continued

Biomarkers in bile, grouped by divergent pathways within known molecular groups/pathways

| Super Pathway | Sub Pathway | Biochemical Name | Platform | Comp ID |
|---|---|---|---|---|
| | gamma-glutamyl | gamma-glutamylvaline | LC/MS pos | 32393 |
| | | gamma-glutamyl-2-aminobutyrate | LC/MS pos | 37092 |
| | | gamma-glutamylleucine | LC/MS pos | 18369 |
| | | gamma-glutamylisoleucine* | LC/MS pos | 34456 |
| | | gamma-glutamylglycine | LC/MS pos | 33949 |
| | | gamma-glutamylmethionine | LC/MS neg | 37539 |
| | | gamma-glutamylphenylalanine | LC/MS pos | 33422 |
| | | gamma-glutamyltyrosine | LC/MS pos | 2734 |
| | | gamma-glutamylthreonine* | LC/MS pos | 33364 |
| | | gamma-glutamyltryptophan | LC/MS pos | 33947 |
| | | gamma-glutamylalanine | LC/MS pos | 37063 |
| Carbohydrate | Aminosugars metabolism | erythronate* | GC/MS | 33477 |
| | | fucose | GC/MS | 15821 |
| | | glucuronate | GC/MS | 15443 |
| | Fructose, mannose, galactose, starch, and sucrose metabolism | fructose | GC/MS | 577 |
| | | galactose | GC/MS | 12055 |
| | | mannitol | GC/MS | 15335 |
| | | mannose | GC/MS | 584 |
| | | sorbitol | GC/MS | 15053 |
| | | sucrose | LC/MS neg | 1519 |
| | | raffinose | LC/MS neg | 586 |
| | Oligosaccharide | lactobionate | GC/MS | 20685 |
| | Glycolysis, gluconeogenesis, pyruvate metabolism | glycerate | GC/MS | 1572 |
| | | glucose 1-phosphate | GC/MS | 33755 |
| | | glucose | GC/MS | 20488 |
| | | 1,6-anhydroglucose | GC/MS | 21049 |
| | | pyruvate | GC/MS | 599 |
| | | lactate | GC/MS | 527 |
| | | Isobar: glucuronate, galacturonate, 5-keto-gluconate | LC/MS neg | 33001 |
| | Glyoxylate and dicarboxylate metabolism | oxalate (ethanedioate) | LC/MS neg | 20694 |
| | Nucleotide sugars, pentose metabolism | arabitol | GC/MS | 38075 |
| | | ribitol | GC/MS | 15772 |
| | | threitol | GC/MS | 35854 |
| | | gluconate | GC/MS | 587 |
| | | ribose | GC/MS | 12080 |
| | | ribonate | GC/MS | 38818 |
| | | ribulose | GC/MS | 35855 |
| | | xylitol | GC/MS | 41319 |
| | | arabinose | GC/MS | 575 |
| | | xylose | GC/MS | 15836 |
| | | xylonate | GC/MS | 35638 |
| | | xylulose | GC/MS | 18344 |
| Energy | Krebs cycle | citrate | GC/MS | 1564 |
| | | cis-aconitate | LC/MS neg | 12025 |
| | | alpha-ketoglutarate | GC/MS | 33453 |
| | | succinate | LC/MS neg | 1437 |
| | | fumarate | GC/MS | 1643 |
| | | malate | GC/MS | 1303 |
| | Oxidative phosphorylation | acetylphosphate | GC/MS | 15488 |
| | | phosphate | GC/MS | 11438 |
| Lipid | Essential fatty acid | linoleate (18:2n6) | LC/MS neg | 1105 |
| | | linolenate [alpha or gamma; (18:3n3 or 6)] | LC/MS neg | 34035 |
| | | dihomo-linolenate (20:3n3 or n6) | LC/MS neg | 35718 |
| | | eicosapentaenoate (EPA; 20:5n3) | LC/MS neg | 18467 |
| | | docosapentaenoate (n3 DPA; 22:5n3) | LC/MS neg | 32504 |
| | | docosapentaenoate (n6 DPA; 22:5n6) | LC/MS neg | 37478 |
| | | docosahexaenoate (DHA; 22:6n3) | LC/MS neg | 19323 |
| | Medium chain fatty acid | caproate (6:0) | LC/MS neg | 32489 |
| | | heptanoate (7:0) | LC/MS neg | 1644 |
| | | caprylate (8:0) | LC/MS neg | 32492 |
| | | pelargonate (9:0) | GC/MS | 12035 |
| | | laurate (12:0) | GC/MS | 1645 |
| | | 2-aminoheptanoic acid | LC/MS pos | 43761 |
| | Long chain fatty acid | myristate (14:0) | LC/MS neg | 1365 |
| | | pentadecanoate (15:0) | LC/MS neg | 1361 |
| | | palmitate (16:0) | LC/MS neg | 1336 |
| | | palmitoleate (16:1n7) | LC/MS neg | 33447 |
| | | margarate (17:0) | LC/MS neg | 1121 |
| | | 10-heptadecenoate (17:1n7) | LC/MS neg | 33971 |

TABLE 9-continued

Biomarkers in bile, grouped by divergent pathways within known molecular groups/pathways

| Super Pathway | Sub Pathway | Biochemical Name | Platform | Comp ID |
|---|---|---|---|---|
| | | stearate (18:0) | LC/MS neg | 1358 |
| | | oleate (18:1n9) | GC/MS | 1359 |
| | | cis-vaccenate (18:1n7) | GC/MS | 33970 |
| | | nonadecanoate (19:0) | LC/MS neg | 1356 |
| | | 10-nonadecenoate (19:1n9) | LC/MS neg | 33972 |
| | | arachidate (20:0) | LC/MS neg | 44679 |
| | | eicosenoate (20:1n9 or 11) | LC/MS neg | 33587 |
| | | dihomo-linoleate (20:2n6) | LC/MS neg | 17805 |
| | | mead acid (20:3n9) | LC/MS neg | 35174 |
| | | arachidonate (20:4n6) | LC/MS neg | 1110 |
| | | docosadienoate (22:2n6) | LC/MS neg | 32415 |
| | | adrenate (22:4n6) | LC/MS neg | 32980 |
| | Fatty acid, oxidized | 9,10-epoxystearate | LC/MS neg | 39627 |
| | Fatty acid, methyl ester | myristate, methyl ester | GC/MS | 12289 |
| | | pentadecanoate, methyl ester | GC/MS | 12288 |
| | | palmitate, methyl ester | GC/MS | 12091 |
| | | margarate, methyl ester | GC/MS | 11984 |
| | | stearate, methyl ester | GC/MS | 6097 |
| | | oleate, methyl ester | GC/MS | 36796 |
| | | linoleate, methyl ester | GC/MS | 36801 |
| | Fatty acid, monohydroxy | 3-hydroxypropanoate | GC/MS | 42103 |
| | | 2-hydroxystearate | LC/MS neg | 17945 |
| | | 2-hydroxypalmitate | LC/MS neg | 35675 |
| | Fatty acid, dicarboxylate | 2-hydroxyglutarate | GC/MS | 37253 |
| | | sebacate (decanedioate) | LC/MS neg | 32398 |
| | | azelate (nonanedioate) | LC/MS neg | 18362 |
| | Fatty acid, amide | stearamide | GC/MS | 37487 |
| | Fatty acid, beta-oxidation | suberylglycine | LC/MS neg | 35419 |
| | Fatty acid, branched | 13-methylmyristic acid | LC/MS neg | 38293 |
| | | 15-methylpalmitate (isobar with 2-methylpalmitate) | LC/MS neg | 38768 |
| | | 17-methylstearate | LC/MS neg | 38296 |
| | Fatty acid metabolism (also BCAA metabolism) | propionylcarnitine | LC/MS pos | 32452 |
| | | propionylglycine | LC/MS neg | 31932 |
| | | butyrylcarnitine | LC/MS pos | 32412 |
| | Fatty acid metabolism | isovalerate | LC/MS neg | 34732 |
| | | hexanoylglycine | LC/MS neg | 35436 |
| | Carnitine metabolism | deoxycarnitine | LC/MS pos | 36747 |
| | | carnitine | LC/MS pos | 15500 |
| | | 3-dehydrocarnitine* | LC/MS pos | 32654 |
| | | acetylcarnitine | LC/MS pos | 32198 |
| | | hexanoylcarnitine | LC/MS pos | 32328 |
| | | octanoylcarnitine | LC/MS pos | 33936 |
| | | laurylcarnitine | LC/MS pos | 34534 |
| | | palmitoylcarnitine | LC/MS pos | 22189 |
| | | stearoylcarnitine | LC/MS pos | 34409 |
| | | oleoylcarnitine | LC/MS pos | 35160 |
| | Bile acid metabolism | glycocholate | LC/MS pos | 18476 |
| | | glycohyocholate | LC/MS pos | 42574 |
| | | taurohyocholate | LC/MS neg | 42603 |
| | | taurochenodeoxycholate | LC/MS neg | 18494 |
| | | taurodeoxycholate | LC/MS neg | 12261 |
| | | glycodeoxycholate | LC/MS neg | 18477 |
| | | glycochenodeoxycholate | LC/MS neg | 32346 |
| | | glycolithocholate | LC/MS neg | 31912 |
| | | glycolithocholate sulfate* | LC/MS neg | 32620 |
| | | taurolithocholate | LC/MS neg | 31889 |
| | | glycocholenate sulfate* | LC/MS neg | 32599 |
| | | taurocholenate sulfate* | LC/MS neg | 32807 |
| | | glycohyodeoxycholic acid | LC/MS pos | 43501 |
| | Glycerolipid metabolism | ethanolamine | GC/MS | 1497 |
| | | glycerol | GC/MS | 15122 |
| | | choline | LC/MS pos | 15506 |
| | | glycerol 3-phosphate (G3P) | GC/MS | 15365 |
| | | glycerophosphorylcholine (GPC) | LC/MS pos | 15990 |
| | Inositol metabolism | myo-inositol | GC/MS | 19934 |
| | | chiro-inositol | GC/MS | 37112 |
| | | pinitol | GC/MS | 37086 |
| | | inositol 1-phosphate (I1P) | GC/MS | 1481 |
| | Ketone bodies | 3-hydroxybutyrate (BHBA) | GC/MS | 542 |
| | | 1,2-propanediol | GC/MS | 38002 |

TABLE 9-continued

Biomarkers in bile, grouped by divergent pathways within known molecular groups/pathways

| Super Pathway | Sub Pathway | Biochemical Name | Platform | Comp ID |
|---|---|---|---|---|
| | Lysolipid | 1-palmitoylglycerophosphoethanolamine | LC/MS neg | 35631 |
| | | 2-palmitoylglycerophosphoethanolamine* | LC/MS neg | 35688 |
| | | 1-stearoylglycerophosphoethanolamine | LC/MS neg | 34416 |
| | | 1-oleoylglycerophosphoethanolamine | LC/MS neg | 35628 |
| | | 1-linoleoylglycerophosphoethanolamine* | LC/MS neg | 32635 |
| | | 2-linoleoylglycerophosphoethanolamine* | LC/MS neg | 36593 |
| | | 1-arachidonoylglycerophosphoethanolamine* | LC/MS neg | 35186 |
| | | 2-arachidonoylglycerophosphoethanolamine* | LC/MS neg | 32815 |
| | | 1-stearoylglycerophosphoglycerol | LC/MS neg | 34437 |
| | | 2-myristoylglycerophosphocholine* | LC/MS pos | 35626 |
| | | 1-palmitoylglycerophosphocholine (16:0) | LC/MS neg | 33955 |
| | | 2-palmitoylglycerophosphocholine* | LC/MS neg | 35253 |
| | | 1-palmitoleoylglycerophosphocholine (16:1)* | LC/MS pos | 33230 |
| | | 1-margaroylglycerophosphocholine (17:0) | LC/MS neg | 33957 |
| | | 1-stearoylglycerophosphocholine (18:0) | LC/MS pos | 33961 |
| | | 2-stearoylglycerophosphocholine* | LC/MS pos | 35255 |
| | | 1-oleoylglycerophosphocholine (18:1) | LC/MS neg | 33960 |
| | | 2-oleoylglycerophosphocholine* | LC/MS neg | 35254 |
| | | 1-linoleoylglycerophosphocholine (18:2n6) | LC/MS neg | 34419 |
| | | 2-linoleoylglycerophosphocholine* | LC/MS neg | 38087 |
| | | 1-dihomo-linoleoylglycerophosphocholine (20:2n6)* | LC/MS pos | 33871 |
| | | 1-eicosatrienoylglycerophosphocholine (20:3)* | LC/MS pos | 33821 |
| | | 1-arachidonoylglycerophosphocholine (20:4n6)* | LC/MS pos | 33228 |
| | | 2-arachidonoylglycerophosphocholine* | LC/MS pos | 35256 |
| | | 1-docosapentaenoylglycerophosphocholine (22:5n3)* | LC/MS pos | 37231 |
| | | 1-docosahexaenoylglycerophosphocholine (22:6n3)* | LC/MS pos | 33822 |
| | | 2-docosahexaenoylglycerophosphocholine* | LC/MS neg | 35883 |
| | | 1-palmitoylplasmenylethanolamine* | LC/MS neg | 39270 |
| | | 1-stearoylplasmenylethanolamine* | LC/MS neg | 39271 |
| | | 1-docosahexaenoylglycerophosphoethanolamine* | LC/MS neg | 44633 |
| | | 1-linolenoylglycerophosphocholine (18:3n3)* | LC/MS pos | 44562 |
| | | 1-eicosapentaenoylglycerophosphocholine (20:5n3)* | LC/MS pos | 44563 |
| | Monoacylglycerol | 1-palmitoylglycerol (1-monopalmitin) | GC/MS | 21127 |
| | | 1-oleoylglycerol (1-monoolein) | LC/MS pos | 21184 |
| | | 1-linoleoylglycerol (1-monolinolein) | LC/MS pos | 27447 |
| | Sphingolipid | sphingosine | LC/MS pos | 17747 |
| | | palmitoyl sphingomyelin | GC/MS | 37506 |
| | | stearoyl sphingomyelin | GC/MS | 19503 |
| | Sterol/Steroid | lathosterol | GC/MS | 39864 |
| | | cholesterol | GC/MS | 63 |
| | | campesterol | GC/MS | 39511 |
| | | 4-androsten-3beta,17beta-diol disulfate 1* | LC/MS neg | 37202 |
| | | 4-androsten-3beta,17beta-diol disulfate 2* | LC/MS neg | 37203 |
| | | 5alpha-androstan-3beta,17beta-diol disulfate | LC/MS neg | 37190 |
| | | 5alpha-pregnan-3beta,20alpha-diol disulfate | LC/MS neg | 37198 |
| | | pregnen-diol disulfate* | LC/MS neg | 32562 |
| | | 21-hydroxypregnenolone disulfate | LC/MS neg | 37173 |
| Nucleotide | Purine metabolism, (hypo)xanthine/inosine containing | xanthine | GC/MS | 3147 |
| | | xanthosine | LC/MS neg | 15136 |
| | | hypoxanthine | LC/MS pos | 3127 |
| | | inosine | LC/MS neg | 1123 |
| | | 2'-deoxyinosine | LC/MS neg | 15076 |
| | Purine metabolism, adenine containing | adenine | LC/MS pos | 554 |
| | | adenosine | LC/MS pos | 555 |
| | | N1-methyladenosine | LC/MS pos | 15650 |
| | | adenosine-2',3'-cyclic monophosphate | LC/MS pos | 37467 |
| | Purine metabolism, guanine containing | guanine | GC/MS | 418 |
| | | 7-methylguanine | LC/MS pos | 35114 |
| | | guanosine | LC/MS neg | 1573 |
| | | 2'-deoxyguanosine | LC/MS neg | 1411 |
| | | N1-methylguanosine | LC/MS pos | 31609 |
| | | N2,N2-dimethylguanosine | LC/MS pos | 35137 |
| | | N6-carbamoylthreonyladenosine | LC/MS pos | 35157 |

TABLE 9-continued

Biomarkers in bile, grouped by divergent pathways within known molecular groups/pathways

| Super Pathway | Sub Pathway | Biochemical Name | Platform | Comp ID |
|---|---|---|---|---|
| | Purine metabolism, urate metabolism | urate | GC/MS | 1604 |
| | | allantoin | GC/MS | 1107 |
| | Pyrimidine metabolism, cytidine containing | cytidine | LC/MS neg | 514 |
| | | 2'-deoxycytidine | LC/MS pos | 15949 |
| | Pyrimidine metabolism, orotate containing | orotate | GC/MS | 1505 |
| | Pyrimidine metabolism, thymine containing | thymidine | LC/MS pos | 2183 |
| | Pyrimidine metabolism, uracil containing | uridine | LC/MS neg | 606 |
| | | pseudouridine | LC/MS pos | 33442 |
| | Purine and pyrimidine metabolism | methylphosphate | GC/MS | 37070 |
| Cofactors and vitamins | Ascorbate and aldarate metabolism | gulono-1,4-lactone | GC/MS | 33454 |
| | | threonate | GC/MS | 27738 |
| | | glucurono-6,3-lactone | GC/MS | 20680 |
| | | arabonate | GC/MS | 37516 |
| | Pterins | isoxanthopterin | LC/MS pos | 27732 |
| | Hemoglobin and porphyrin metabolism | heme | LC/MS pos | 41754 |
| | | L-urobilin | LC/MS neg | 40173 |
| | | Coproporphyrin I | LC/MS neg | 39318 |
| | | coproporphyrin III | LC/MS neg | 39317 |
| | | bilirubin (Z,Z) | LC/MS neg | 27716 |
| | | bilirubin (E,E)* | LC/MS neg | 32586 |
| | | biliverdin | LC/MS neg | 2137 |
| | | protoporphyrin IX | LC/MS neg | 39321 |
| | Nicotinate and nicotinamide metabolism | nicotinamide | LC/MS pos | 594 |
| | | quinolinate | GC/MS | 1899 |
| | | N1-Methyl-2-pyridone-5-carboxamide | LC/MS neg | 40469 |
| | Pantothenate and CoA metabolism | pantothenate | LC/MS neg | 1508 |
| | Pyridoxal metabolism | pyridoxate | LC/MS neg | 31555 |
| | Riboflavin metabolism | riboflavin (Vitamin B2) | LC/MS pos | 1827 |
| | Tocopherol metabolism | alpha-tocopherol | GC/MS | 1561 |
| Xenobiotics | Benzoate metabolism | hippurate | LC/MS neg | 15753 |
| | | 3-hydroxyhippurate | LC/MS neg | 39600 |
| | | 4-hydroxyhippurate | LC/MS neg | 35527 |
| | | 3-hydroxymandelate | GC/MS | 22112 |
| | | 4-hydroxymandelate | GC/MS | 1568 |
| | | benzoate | GC/MS | 15778 |
| | | p-hydroxybenzaldehyde | GC/MS | 17665 |
| | Chemical | glycolate (hydroxyacetate) | GC/MS | 15737 |
| | | 2-hydroxyisobutyrate | GC/MS | 22030 |
| | | glycerol 2-phosphate | GC/MS | 27728 |
| | | 3-hydroxypyridine | GC/MS | 21169 |
| | | HEPES | LC/MS neg | 21248 |
| | | 2-ethylhexanoate (isobar with 2-propylpentanoate) | LC/MS neg | 35490 |
| | | 2-mercaptoethanol* | GC/MS | 37225 |
| | | 2-piperidinone | LC/MS pos | 43400 |
| | | dimethyl sulfone | LC/MS pos | 43424 |
| | Drug | ketamine | LC/MS pos | 35128 |
| | | methylprednisolone | LC/MS pos | 42977 |
| | | pantoprazole | LC/MS pos | 38609 |
| | | vecuronium | LC/MS pos | 42591 |
| | | oxypurinol | GC/MS | 41725 |
| | Food component/Plant | 5-ketogluconate | GC/MS | 15687 |
| | | quinate | GC/MS | 18335 |
| | | benzyl alcohol | GC/MS | 22294 |
| | | ergothioneine | LC/MS pos | 37459 |
| | | N-(2-furoyl)glycine | LC/MS pos | 31536 |
| | | stachydrine | LC/MS pos | 34384 |
| | | homostachydrine* | LC/MS pos | 33009 |
| | | cinnamoylglycine | LC/MS neg | 38637 |
| | | 1,1-kestotetraose | LC/MS neg | 39796 |
| | | equol glucuronide | LC/MS neg | 41948 |
| | Sugar, sugar substitute, starch | erythritol | GC/MS | 20699 |
| | Bacterial | Isobar: tartronate, dihydroxyfumarate | GC/MS | 42356 |
| | Phthalate | bis(2-ethylhexyl)phthalate | GC/MS | 21069 |

Example 5

Biomarkers of Liver Function

This example describes the identification of biomarkers of liver function.

Figure 20D:
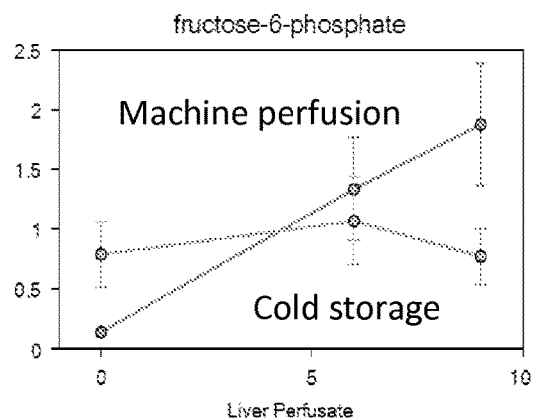
Figure 20E:
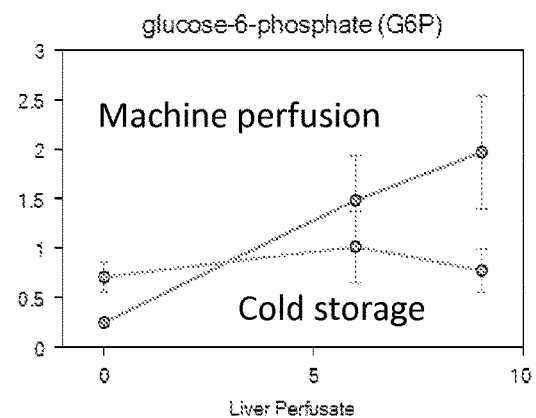

The glucose-amino acid cycle and branched-chain amino acid mobilization were markedly elevated in livers undergoing machine perfusion as described in Example 1. Glucose was elevated in MP relative to CSP liver perfusates throughout the study and may have been converted to lactate via the glycolysis pathway. In spite a small amount of glucose being initially present at the perfusate in the machine perfusion group, a constant rate of gluconeogenesis can be detected when additional metabolites are analyzed (FIG. 20A). Lactate is a predominant source of carbon atoms for glucose synthesis by gluconeogenesis. The livers had an intact aerobic metabolism and were able to convert lactate into pyruvate (FIGS. 20B and 20C). The same metabolic pathway can be illustrated by the progressive production of fructose-6-phosphate and glycose-6-phosphate in the livers under machine perfusion (FIGS. 20D and 20E).

Figure 21A:
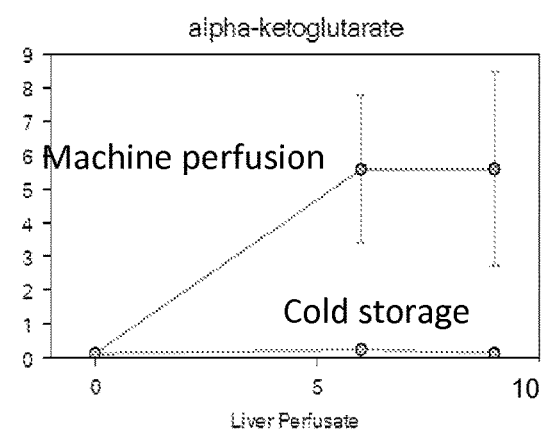
FIGS. 21A and 21B are a pair of graphs showing alpha-ketoglutarate (FIG. 21A) and glutamate production (FIG. 21B) in machine perfused and cold storage liver perfusate over the course of the experiment (hours). The X-axis shows concentration in I/U. The Y-axis shows 3 time points (0=3 hours, 5=6 hours and 10=9 hours) when samples were obtained.
Figure 21B:
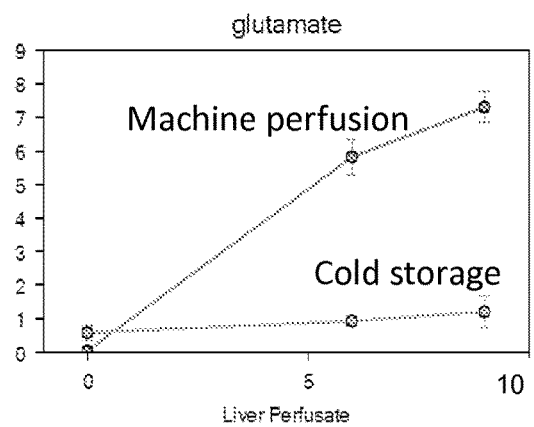

Branched-chain amino acid (BCAA) oxidation showed a strong differential increase in machine perfusion perfusates at the 6 and 9 hour time points as demonstrated by the BCAAs valine, isoleucine, and leucine (FIG. 17A-17C) and their respective deamination products 3-methyl-2-oxobutyrate, 3-methyl-2-oxovalerate, and 4-methyl-2-oxopentanoate. Several primary metabolites and side-products of the BCAA pathways were elevated in the machine perfusion group. Deamination by branched-chain aminotransferase (BCAT) is the first (and fully reversible) step in the oxidation of BCAAs and is followed by the irreversible mitochondrial reaction catalyzed by branched-chain ketoacid dehydrogenase. The tricarboxylic acid (TCA) cycle component alpha-ketoglutarate is a co-substrate for BCAT and leads to the co-formation of glutamate. Alpha-ketoglutarate and glutamate were both elevated in the machine perfusion group relative to the cold storage group at 6 and 9 hour as was glutamine, which can be derived from glutamate. It is possible that alpha-ketoglutarate, glutamate, and glutamine were elevated in response to demand for alpha-ketoglutarate that promoted its production by the TCA cycle and its subsequent conversion to glutamate via the action of BCAT (FIGS. 21A and 21B).

Figure 22:
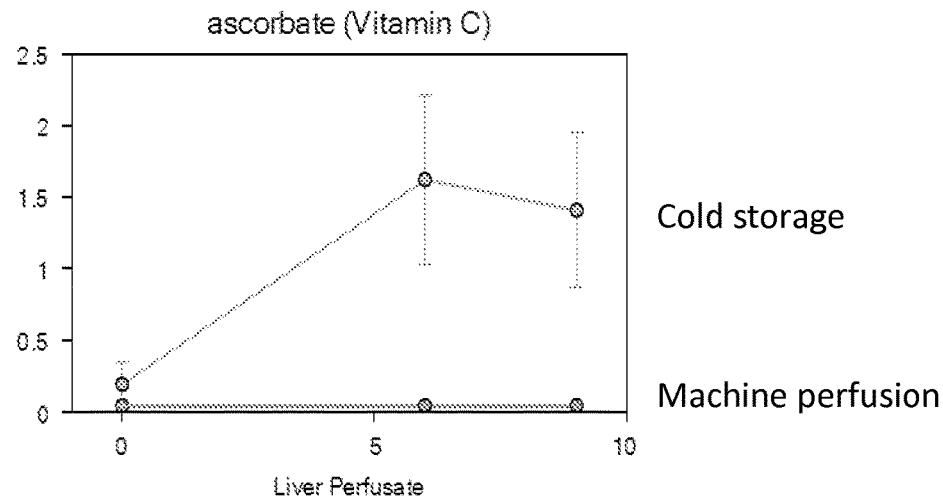
FIG. 22 is a graph showing ascorbate in in machine perfused and cold storage liver perfusate over the course of the experiment (hours). The X-axis shows concentration in I/U. The Y-axis shows 3 time points (0=3 hours, 5=6 hours and 10=9 hours) when samples were obtained.
Figure 23A:
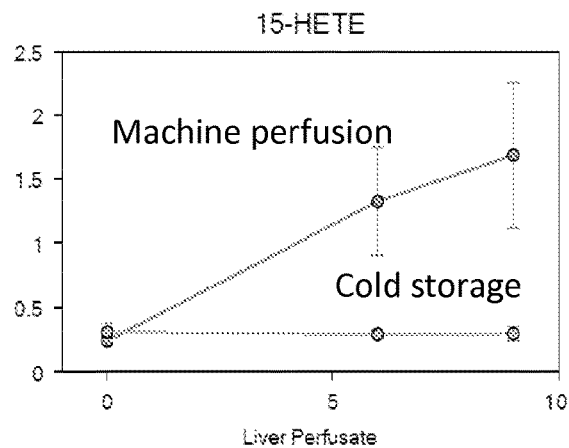
FIGS. 23A and 23B are a pair of graphs showing 15-HETE (FIG. 23A) and 12-HETE (FIG. 23B) in machine perfused and cold storage liver perfusate over the course of the experiment (hours). The X-axis shows concentration in I/U. The Y-axis shows 3 time points (0=3 hours, 5=6 hours and 10=9 hours) when samples were obtained.
Figure 23B:
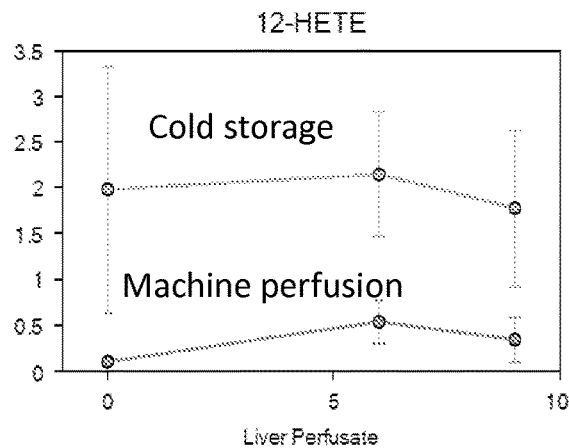

Perfusate profiling revealed differences in stress responses over time between the two preservation conditions. Biochemicals that provide insight into oxidative, inflammatory, and energy stress were among those showing a strong separation between perfusate profiles from the two preservation conditions. For instance, although there were only 2 samples in the perfusate CSP group at the baseline (0 hour) time point, ascorbate was detected in both whereas it was not detected in any of the MP baseline samples. It was detected in all samples from the 6 and 9 hour time points in the CSP samples but was not detected in any of the MP samples at these time points (FIG. 22). Pigs, unlike humans, are capable of synthesizing ascorbate but the expression of the key synthetic enzyme, L-gulono-gamma-lactone oxidase, varies with stress, so ascorbate's presence in the cold static preservation group samples but absence in the machine perfusion samples could be an indication of different levels of perceived oxidant stress by livers subjected to the different preservation conditions.

Evidence of lipoxygenase activity was observed and differed by preservation method. 15-HETE, the product of 15-lipoxygenase, was specifically elevated in machine perfusion perfusates whereas 12-HETE, the product of 12-lipoxygenase, was stably elevated in the cold storage preservation perfusate across all time points but was low in all MP perfusate samples (FIGS. 23A and 23B). 15-lipoxygenase is believed to play a role in the selective breakdown and recycling of peroxisomes whereas 12-HETE (and 15-HETE to a lesser extent) has a more traditional role in promoting inflammation. Altogether this suggests that inflammation was greater in the CSP group than MP samples.

Figure 24:
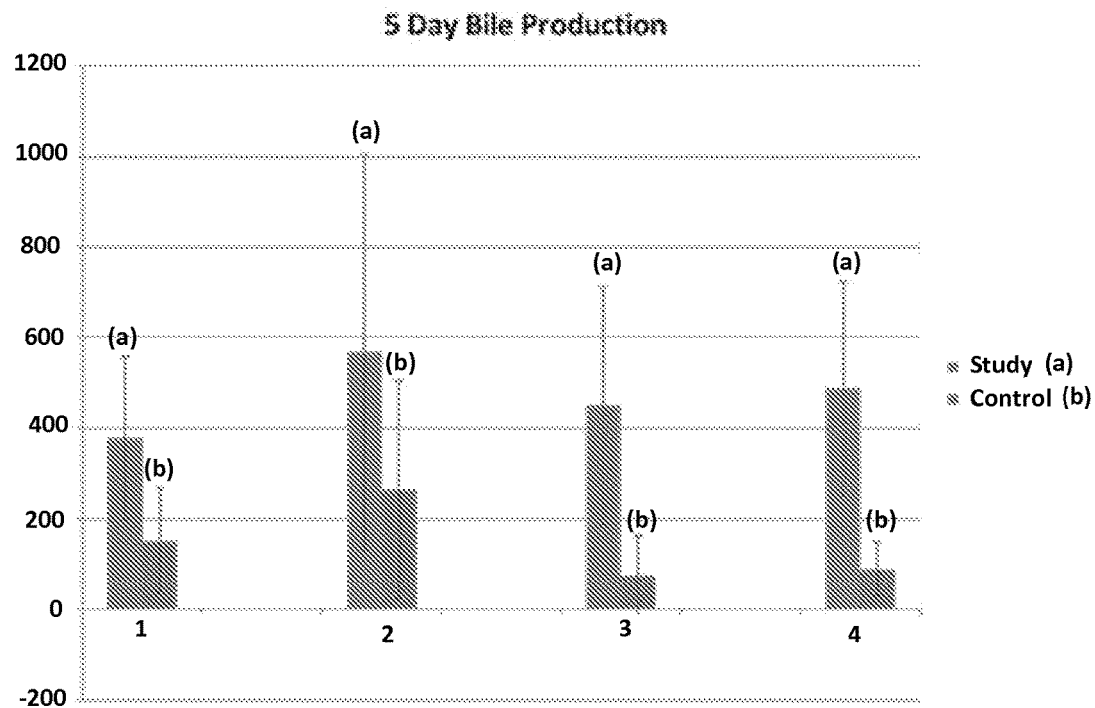
FIG. 24 is a graph showing bile production in the post-operative period by machine perfused (study) and cold storage (control) animals following allograft reperfusion.

Finally, bile production was increased within both 24 hours of liver allograft perfusion and over the 5-day postoperative period (FIG. 24). This indicates overall organ function. In addition, biomarkers from bile could be used as indicators of organ function or dysfunction.

Example 6

Principal Component Analysis of Liver Perfusate

This example describes principal component analysis (PCA) of perfusate from MP or CSP livers.

PCA is a tool for defining primary characteristics of a highly-dimensional dataset. The analysis achieves dimension reduction by extracting a few (but not all) principal components that describe most of the variation in the original multivariate dataset with the least loss of information. Based on linear transformation and decomposition of a number of correlated variables of a multi-dimensional dataset to a number of uncorrelated components, principal components are identified. The principal components are estimated as the projections of the data set on the eigenvectors of the covariance or correlation matrix of the data set. See, e.g., Janes et al., *Nat. Rev. Mol. Cell. Biol.* 7:820, 2006; Mi et al., *PLoS ONE* 6:19424, 2011.

Figure 25:
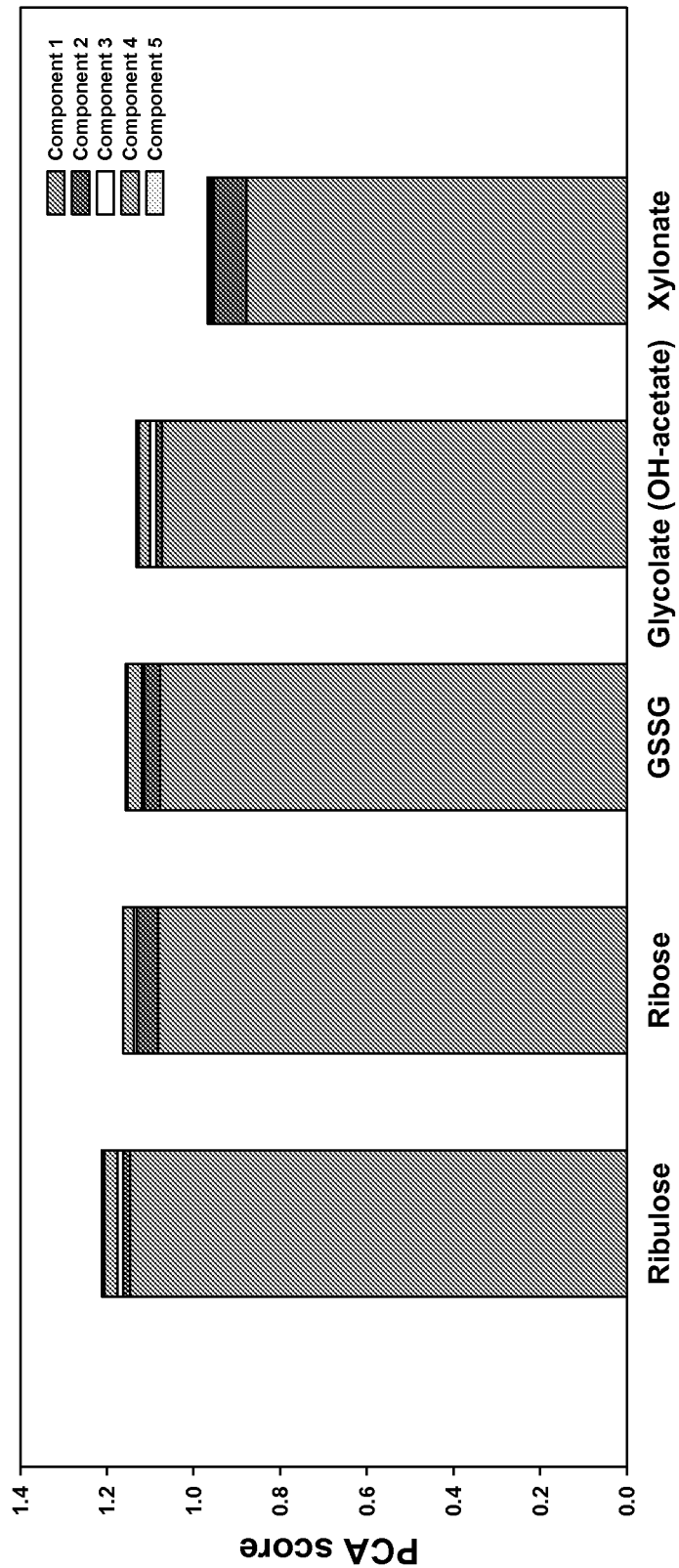
FIG. 25 is a graph showing principal component analysis (PCA) carried out on the metabolomic profile of perfusate at three time points (3, 6 and 9 hours). Variables are ordered by the sum of their contribution to all components, with contributions to individual components represented by different colored sections of the bars. In MP livers, variables representing carbohydrate metabolism (ribulose, ribose, glycolate) and antioxidant defenses (oxidized homo-glutathione-GSSG) were principal drivers of metabolic changes.
Figure 26:
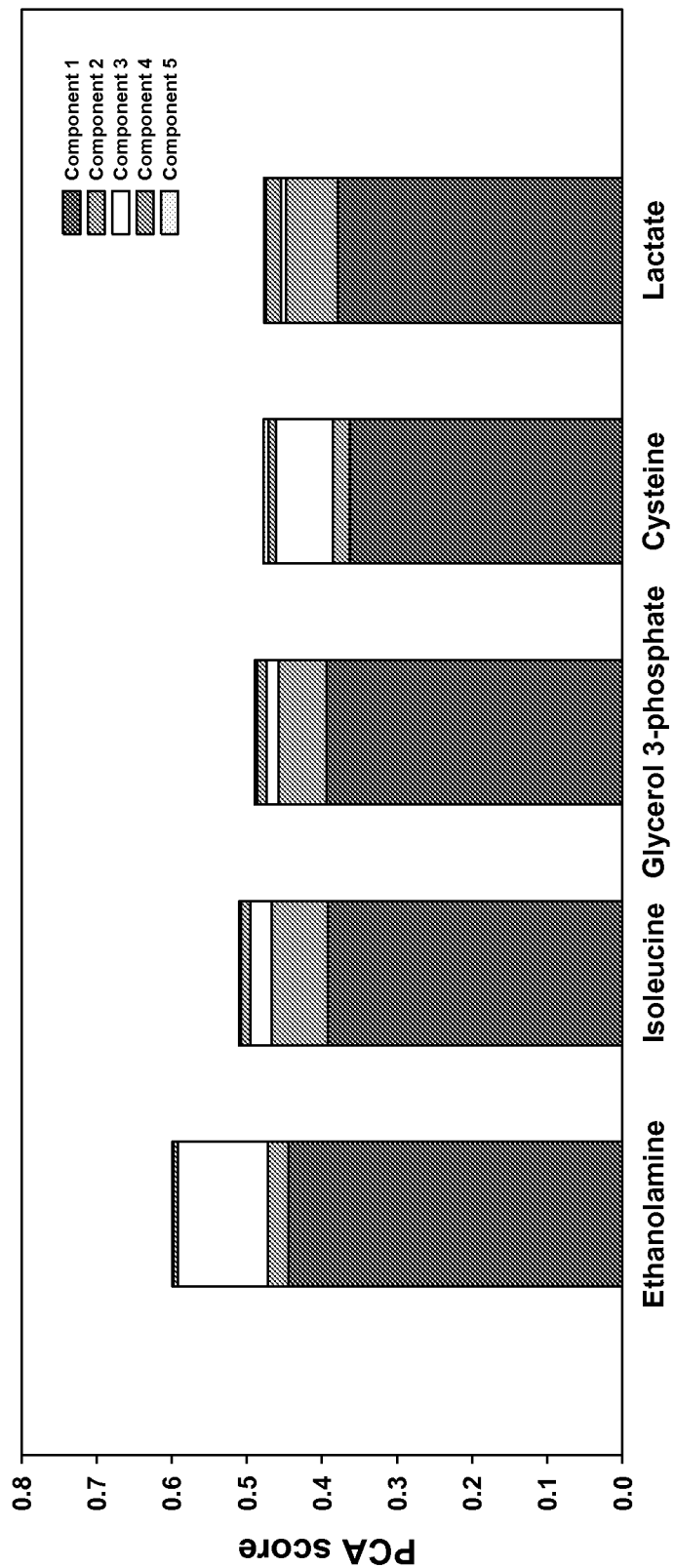
FIG. 26 is a graph showing PCA carried out on the metabolomic profile of perfusate at three time points (3, 6 and 9 hours). Variables are ordered by the sum of their contribution to all components, with contributions to individual components represented by different colored sections of the bars. In CSP livers, PCA showed ethanolamine to be the principal driver of metabolic changes, suggesting a role for fatty acid metabolism.

PCA was carried out on the metabolomics profile of liver perfusates from MP or CSP livers at 3, 6, and 9 hour time points. In the MP livers, variables representing carbohydrate metabolism (ribulose, ribose, glycolate) and antioxidant defenses (oxidized homo-glutathione (GSSG)) were principal drivers of metabolic changes (FIG. 25). In the CSP livers, PCA showed ethanolamine to be the principal driver of metabolic changes, suggesting a role for fatty acid metabolism (FIG. 26).

Example 7

Dynamic Bayesian Network Analysis of Liver Perfusate

The example describes dynamic Bayesian network (DBN) analysis of perfusate from MP or CSP livers.

Figure 27:
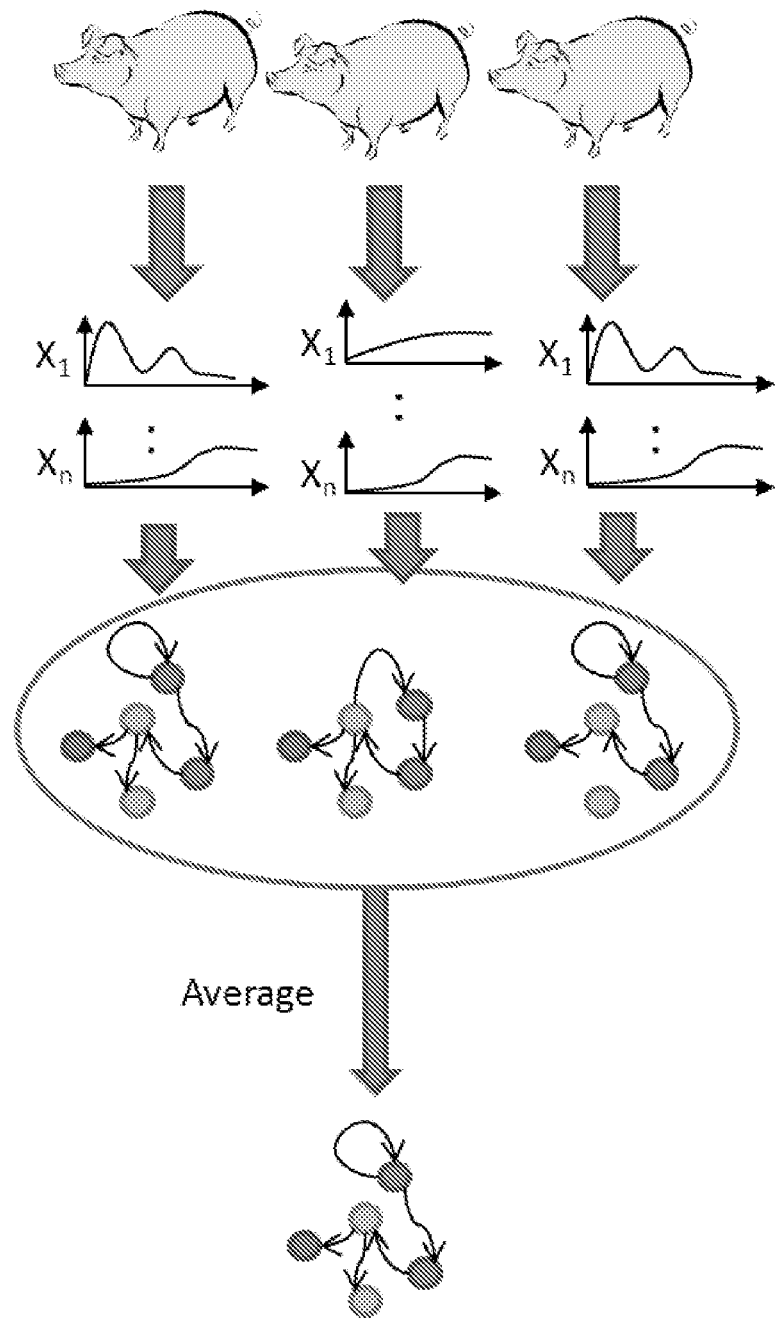
FIG. 27 is a representation of the method Dynamic Bayesian Networks (DBN) utilized to establish the role of different cytokines while interacting in response to an initial inflammatory event (e.g. ischemia-reperfusion acquired during liver preservation).

DBN analysis infers graphs for each component individually from each liver. If an arrow exists in >50% of the individual networks, it is included in the final consensus network. The thickness of the arrows indicate the percentage of individual networks in which it is present (FIG. 27).

Figure 28:
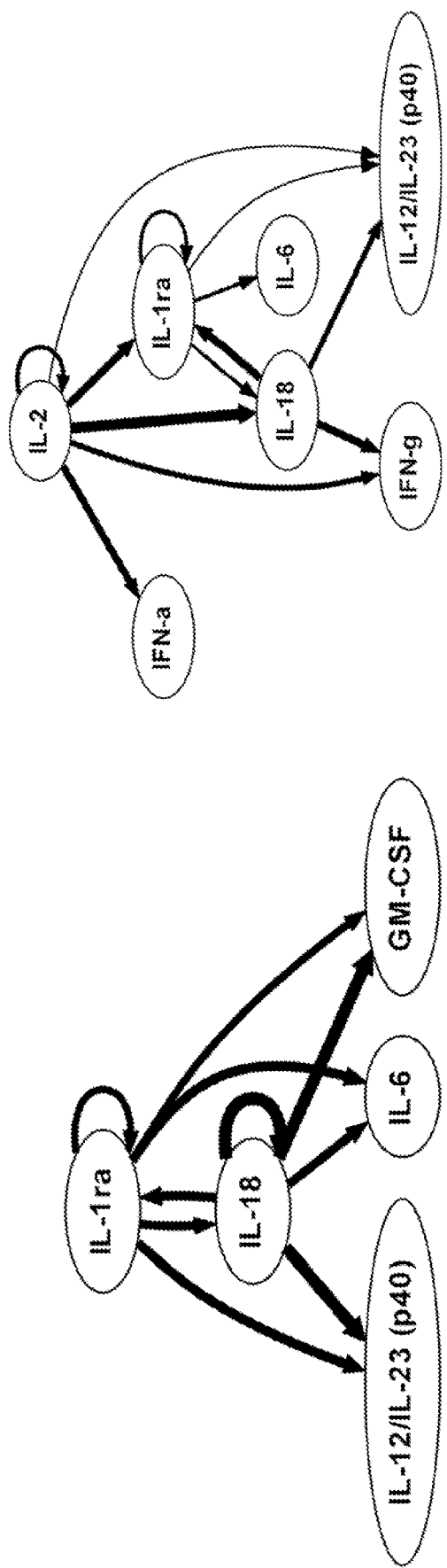
FIG. 28 shows DBN analysis suggesting two different pathways for cytokine regulation in livers being perfused by different techniques (Control with cold static preservation—CSP and Study with machine perfusion in combination with the hemoglobin-based-oxygen carrier solution—MP/HBOC).

DBN was used to determine the role of different cytokines while interacting in response to an initial inflammatory event (e.g., ischemia-reperfusion acquired during liver preservation). The analysis suggests two different pathways for cytokine regulation in livers being perfused by CSP or MP (FIG. 28).

In view of the many possible embodiments to which the principles of the disclosure may be applied, it should be recognized that the illustrated embodiments are only examples and should not be taken as limiting the scope of the invention. Rather, the scope of the invention is defined We therefore claim as our invention all that comes within the scope and spirit of these claims.

We claim:

1. A method for identifying organ dysfunction, comprising:
    obtaining a sample from an ex vivo organ undergoing machine perfusion with a perfusion solution comprising a hemoglobin-based oxygen carrier at subnormothermic temperatures, wherein the perfusion solution comprises 3-4 g/dL acellular cross-linked hemoglobin in a physiologically acceptable medium, has a pH of about 7.55-7.85 at room temperature, an osmolality of about 290-300 mOsm/kg, and a colloid osmotic pressure of about 35-65 mm Hg;
    measuring the amount of glucose, lactate, pyruvate, fructose 6-phosphate, glucose 6-phosphate, valine, leucine, isoleucine, alpha-ketoglutarate, glutamate, 15-HETE, and 12-HETE in the sample;
    comparing the amount of glucose, lactate, pyruvate, fructose 6-phosphate, glucose 6-phosphate, valine, leucine, isoleucine, alpha-ketoglutarate, glutamate, 15-HETE, and 12-HETE with the amount of glucose, lactate, pyruvate, fructose 6-phosphate, glucose 6-phosphate, valine, leucine, isoleucine, alpha-ketoglutarate, glutamate, 15-HETE, and 12-HETE in a reference or control from one or more organs that are known to have organ dysfunction;
    determining that glucose, lactate, pyruvate, fructose 6-phosphate, glucose 6-phosphate, valine, leucine, isoleucine, alpha-ketoglutarate, glutamate, 15-HETE, and 12-HETE are biomarkers of organ dysfunction when the amount of the glucose, lactate, pyruvate, fructose 6-phosphate, glucose 6-phosphate, valine, leucine, isoleucine, alpha-ketoglutarate, glutamate, and 15-HETE is decreased compared to the reference or control and the amount of the 12-HETE is increased compared to the reference or control;
    utilizing the amount of the glucose, lactate, pyruvate, fructose 6-phosphate, glucose 6-phosphate, valine, leucine, isoleucine, alpha-ketoglutarate, glutamate, 15-HETE, and 12-HETE to select the organ undergoing machine perfusion when the amount of the glucose, lactate, pyruvate, fructose 6-phosphate, glucose 6-phosphate, valine, leucine, isoleucine, alpha-ketoglutarate, glutamate, 15-HETE, and 12-HETE of is a predictor of organ function; and
    transplanting the selected organ into a transplant recipient.

2. The method of claim 1, wherein the perfusion solution comprises 3-4 g/dL cross-linked hemoglobin, 25-30 mM NaCl, 1-2 mM KCl, 17-19 mM KH$_2$PO$_4$, 55-65 mM sodium gluconate, 6-8 mM sodium lactate, 3-4 mM magnesium gluconate, 0.6-0.8 mM CaCl$_2$ dihydrate, 15-16 mM NaOH, 3-4 mM adenine, 6-8 mM dextrose, 2-3 mM glutathione, 6-8 mM HEPES, 3-4 mM ribose, 20-25 mM mannitol, 35-40 g/L hydroxyethyl starch, and 40-60 mg/dL N-acetyl-L-cysteine.

3. The method of claim 1, wherein the sample comprises perfusion or preservation solution from the organ, a biopsy from the organ, or a fluid produced by the organ.

4. The method of claim 1, wherein the organ is a liver, a kidney, a lung, a heart, a pancreas, a small intestine, a limb, an extremity, or a portion of any one thereof.

5. A method for identifying organ dysfunction, comprising:
    obtaining a sample from an ex vivo organ undergoing machine perfusion with a perfusion solution comprising a hemoglobin-based oxygen carrier at subnormothermic temperatures, wherein the perfusion solution comprises 3-4 g/dL acellular cross-linked hemoglobin in a physiologically acceptable medium, has a pH of about 7.55-7.85 at room temperature, an osmolality of about 290-300 mOsm/kg, and a colloid osmotic pressure of about 35-65 mm Hg;
    measuring the amount of glucose, lactate, pyruvate, fructose 6-phosphate, glucose 6-phosphate, valine, leucine, isoleucine, alpha-ketoglutarate, glutamate, 15-HETE, and 12-HETE in the sample;
    comparing the amount of the glucose, lactate, pyruvate, fructose 6-phosphate, glucose 6-phosphate, valine, leucine, isoleucine, alpha-ketoglutarate, glutamate, 15-HETE, and 12-HETE with the amount of glucose, lactate, pyruvate, fructose 6-phosphate, glucose 6-phosphate, valine, leucine, isoleucine, alpha-ketoglutarate, glutamate, 15-HETE, and 12-HETE in a reference or control from one or more organs that are known to have organ dysfunction; and
    wherein the amount of the glucose, lactate, pyruvate, fructose 6-phosphate, glucose 6-phosphate, valine, leucine, isoleucine, alpha-ketoglutarate, glutamate, and 15-HETE is decreased compared to the reference or control and the amount of the 12-HETE is increased compared to the reference or control.

6. The method of claim 5, wherein the perfusion solution comprises 3-4 g/dL cross-linked hemoglobin, 25-30 mM NaCl, 1-2 mM KCl, 17-19 mM KH$_2$PO$_4$, 55-65 mM sodium gluconate, 6-8 mM sodium lactate, 3-4 mM magnesium gluconate, 0.6-0.8 mM CaCl$_2$ dihydrate, 15-16 mM NaOH, 3-4 mM adenine, 6-8 mM dextrose, 2-3 mM glutathione, 6-8 mM HEPES, 3-4 mM ribose, 20-25 mM mannitol, 35-40 g/L hydroxyethyl starch, and 40-60 mg/dL N-acetyl-L-cysteine.

7. The method of claim 5, wherein the sample comprises perfusion or preservation solution from the organ, a biopsy from the organ, or a fluid produced by the organ.

8. The method of claim 5, wherein the organ is a liver, a kidney, a lung, a heart, a pancreas, a small intestine, a limb, an extremity, or a portion of any one thereof.

* * * * *